United States Patent
Blaise et al.

(10) Patent No.: US 10,959,930 B2
(45) Date of Patent: Mar. 30, 2021

(54) PROCESS FOR DYEING KERATIN FIBRES USING AT LEAST ONE PARTICULAR TRIARYLMETHANE DYE AND AT LEAST ONE FLUORESCENT DYE

(71) Applicant: L'Oreal, Paris (FR)

(72) Inventors: Christian Blaise, Aulnay-sous-Bois (FR); Hervé David, Aulnay-sous-Bois (FR); Aziz Fadli, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/472,804

(22) PCT Filed: Dec. 20, 2017

(86) PCT No.: PCT/EP2017/083878
§ 371 (c)(1),
(2) Date: Jun. 21, 2019

(87) PCT Pub. No.: WO2018/115156
PCT Pub. Date: Jun. 28, 2018

(65) Prior Publication Data
US 2020/0276097 A1    Sep. 3, 2020

(30) Foreign Application Priority Data

Dec. 22, 2016 (FR) ...................... 1663247

(51) Int. Cl.
| | |
|---|---|
| *A61Q 5/10* | (2006.01) |
| *A61K 8/41* | (2006.01) |
| *A61K 8/46* | (2006.01) |
| *A61K 8/49* | (2006.01) |
| *A61Q 5/06* | (2006.01) |
| *C09B 11/12* | (2006.01) |
| *C09B 23/06* | (2006.01) |

(52) U.S. Cl.
CPC .............. *A61K 8/411* (2013.01); *A61K 8/466* (2013.01); *A61K 8/4926* (2013.01); *A61Q 5/065* (2013.01); *C09B 11/12* (2013.01); *C09B 23/06* (2013.01); *A61K 2800/432* (2013.01); *A61K 2800/434* (2013.01)

(58) Field of Classification Search
CPC .................. A61Q 5/065; A61K 8/4926; A61K 2800/432; A61K 8/411; A61K 8/466; A61K 2800/84; A61K 2800/434; C09B 11/12; C09B 23/06
USPC .................................................... 8/405, 426
See application file for complete search history.

(56) References Cited

U.S. PATENT DOCUMENTS

| | | | |
|---|---|---|---|
| 2005/0011018 A1 | 1/2005 | Greaves | |
| 2005/0271595 A1 | 12/2005 | Brown | |
| 2015/0079008 A1 | 3/2015 | Floyd | |
| 2015/0224041 A1* | 8/2015 | Greaves | ................. A61Q 5/065 |
| | | | 132/208 |

FOREIGN PATENT DOCUMENTS

| | | |
|---|---|---|
| EP | 1133975 A2 | 9/2001 |
| EP | 2039724 A1 | 3/2009 |
| WO | 2010087983 A1 | 5/2010 |
| WO | 2018115156 A1 | 6/2018 |

OTHER PUBLICATIONS

STIC Search Report dated Jul. 13, 2020.*
International Search Report with Translation and Written Opinion dated Feb. 19, 2018, for International Application No. PCT/EP2017/083878, filed Feb. 5, 2018, 4 Pages.
Basic Violet 14, https://pubchem.ncbi.nlm.nih.gov/compound/Rosaniline, Apr. 28, 2017.
Brilliant Blue FCF, Wikipedia Article, https://en.wikipedia.org/wiki/Brilliant_Blue_FCF, Apr. 27, 2017.
Fast Green FCF, Wikipedia Article, https://en.wikipedia.org/wiki/Fast_Green_FCF, Apr. 27, 2017.
Methyl Green, Sigma-Aldrich Catalog, http://www.sigmaaldrich.com/catalog/product/sigma/m6776, Apr. 27, 2017.
Crystal Violet, Wikipedia Article, https://en.wikipedia.org/wiki/Crystal_violet, Apr. 27, 2019.
Dye, Dye intermediates, Fluorescent, Brightener, Pigment Dye, http://www.dyestuffintermediates.com/fluorescent-brightener, Apr. 27, 2017.
Basic Blue 7, U.S. National Library of Medicine, National Center for Biotechnology Information, PubChem, Open Chemistry Database, Aug. 8, 2005.
DASPEI (2-(4-(dimethylamino)styryl)-N-Ethylpyridinium Iodide, ThermoFisher Scientific, May 2, 2018.

* cited by examiner

*Primary Examiner* — Eisa B Elhilo
(74) *Attorney, Agent, or Firm* — Christensen O'Connor Johnson Kindness PLLC

(57) ABSTRACT

The present invention relates to a process for dyeing keratin fibres, in particular human keratin fibres such as the hair, using one or more particular triarylmethane dyes and one or more fluorescent dyes.
The present invention also relates to a cosmetic composition comprising the dyes defined above, and also to a multi-compartment device containing said dyes.
The present invention also relates to the use of said dyes for dyeing light keratin fibres, especially human keratin fibres such as the hair, in chestnut-brown, dark chestnut-brown, brown, brown with a glint, or even black, without using an additional dye other than those defined above.

21 Claims, No Drawings

PROCESS FOR DYEING KERATIN FIBRES USING AT LEAST ONE PARTICULAR TRIARYLMETHANE DYE AND AT LEAST ONE FLUORESCENT DYE

The present invention relates to a process for dyeing keratin fibres, in particular human keratin fibres such as the hair, using one or more particular triarylmethane dyes and one or more fluorescent dyes.

The present invention also relates to a cosmetic composition comprising the dyes defined above, and also to a multi-compartment device containing said dyes.

The present invention also relates to the use of said dyes for dyeing light keratin fibres, especially human keratin fibres such as the hair, in chestnut-brown, dark chestnut-brown, brown, brown with a glint, or even black, without using an additional dye other than those defined above.

Many people have sought for a long time to modify the colour of their hair and in particular to mask their grey hair.

It is especially known practice to dye keratin fibres, in particular human keratin fibres, with dye compositions containing oxidation dye precursors, which are generally known as oxidation bases. These oxidation bases are colourless or weakly coloured compounds, which, when combined with oxidizing products, may give rise to coloured compounds via a process of oxidative condensation.

The shades obtained with these oxidation bases may be modified by combining them with couplers or colour modifiers. The variety of molecules used as oxidation bases and couplers allows a wide range of colours to be obtained.

Another well-known method consists in obtaining semi-permanent dyeing by applying to the keratin fibres direct dyes, which are coloured and colouring molecules that have affinity for said fibres.

The direct dyes conventionally used are chosen from nitrobenzene, anthraquinone, nitropyridine, azo, xanthene, acridine, azine and triarylmethane direct dyes. The chemical species may be nonionic, anionic (acidic dyes) or cationic (basic dyes). The direct dyes may also be natural dyes.

Conventional direct dyeing processes consist in applying to keratin fibres dye compositions comprising direct dyes. After application, a leave-on time is observed so as to allow the dye molecules to penetrate by diffusion into the fibres. On conclusion of the process, the fibres are rinsed.

In contrast with oxidation dyeing, these direct dyeing processes have a tendency to better protect the integrity of the fibres. The resulting colourings are generally chromatic, but, however, are only semi-temporary. The nature of the interactions that bind the direct dyes to the keratin fibres and their desorption from the surface and/or the core of the fibre are responsible for their weak dyeing power.

Although a wide range of colours is currently accessible, it generally proves necessary to combine three dyes of complementary colours—trichromatic principle—in order to obtain a natural shade (see, for example, WO 95/15144 and WO 95/01772). This tripartite combination does not, however, show good persistence with respect to repeated shampooing. It generally, or even systematically, induces an unaesthetic changing of the colour, which the consumer finds dissuasive.

These colourings are furthermore not sufficiently fast in the face of external agents such as light or perspiration.

Thus, there is a real need to implement processes for the direct dyeing of keratin fibres, in particular of human keratin fibres such as the hair, which do not have the drawbacks mentioned above, i.e. which make it possible especially to lead to natural colourings that have good properties, especially in terms of chromaticity, power, intensity, sheen and selectivity, and which are persistent with respect to shampooing.

Another aim of the present invention is thus to be able to dye light keratin fibres efficiently in chestnut-brown, dark chestnut-brown, brown or brown with a glint or even black, by mixing direct dyes, and preferably only two types of direct dye.

The Applicant has found, surprisingly, that a process for dyeing keratin fibres using one or more particular triarylmethane dyes and one or more specific fluorescent dyes makes it possible to achieve the objectives mentioned above; especially to lead to natural chestnut-brown, dark chestnut-brown, brown, brown with a glint or even black colourings, which are not only powerful and shiny, but also shampoo-resistant.

One subject of the present invention is especially a process for dyeing keratin fibres, in particular human keratin fibres such as the hair, comprising the application to said keratin fibres of the following ingredients:

(a) one or more triarylmethane dyes chosen from the compounds of formula (I) below, the optical isomers thereof, the geometrical isomers thereof, the tautomers thereof, the organic or mineral, acid or base salts thereof, the solvates thereof such as hydrates, and mixtures thereof,

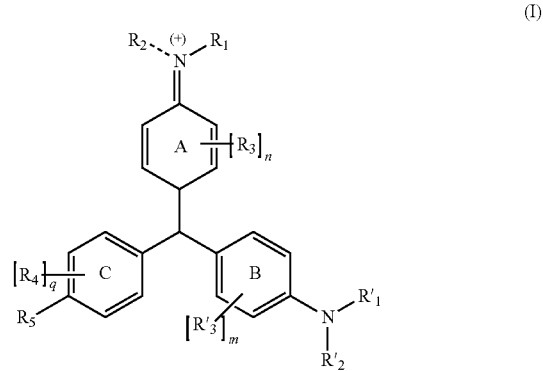

(I)

in which formula (I):
$R_1$, $R_2$, $R'_1$ and $R_2$, which may be identical or different, represent:
  a hydrogen atom,
  a linear or branched $C_1$ to $C_{20}$ alkyl radical;
    that is optionally substituted and/or
    optionally interrupted with one or more heteroatoms, preferably oxygen or sulfur, and/or with one or more groups comprising at least one heteroatom, preferably chosen from oxygen, sulfur, C(O), SO, $SO_2$ and $SO_3^-$, or combinations thereof, or
  a benzyl radical optionally substituted with one or more $SO_3^-$ or $SO_3H$ groups;
$R_3$ and $R'_3$, which may be identical or different, represent, independently of each other:
  a linear or branched $C_1$ to $C_6$ alkyl radical;
  a sulfonate group $SO_3^-$, or
  a sulfonic group $SO_3H$;
n and m, which may be identical or different, represent two integers ranging from 0 to 4;
the radicals $R_4$, which may be identical or different, represent, independently of each other:
  a linear or branched $C_1$ to $C_6$ alkyl radical;
  a hydroxyl radical, a group $SO_3^-$,
a group $SO_3H$,
a halogen atom, preferably a chlorine atom,
or alternatively two adjacent radicals $R_4$ together form an unsaturated 6-membered ring, preferably an aromatic ring such as benzo, optionally substituted with one or more $SO_3^-$ or $SO_3H$ groups;
q is an integer ranging from 0 to 4;
$R_5$ represents:
  a hydrogen atom,
  a halogen atom, preferably a chlorine atom,
  an amino radical,
  a hydroxyl radical,
  a group which is electron-withdrawing via the mesomeric effect, such as $SO_3^-$ or $SO_3H$, or
  a radical —$NR_6R_7$, in which $R_6$ and $R_7$, which may be identical or different, represent, independently of each other:
    a hydrogen atom,
    a linear or branched $C_1$ to $C_6$ alkyl radical;
it being understood that:
  the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and
  the compound of formula (I) optionally comprises one or more anions $An^-$ and optionally one or more cations $M^+$ to ensure the electrical neutrality of the molecule;
with:
  $An^-$ representing an anion, preferably chosen from bromide, chloride, methylsulfate and toluenesulfonate ions or a mixture of these ions; and
  $M^+$ representing a cation, preferably chosen from sodium, potassium, magnesium, calcium, zinc and ammonium ions or a mixture of these ions; and
(b) one or more fluorescent dyes; said fluorescent dyes being direct dyes chosen from cyanin dyes, styryl/hemicyanin dyes, naphthalimide dyes, and mixtures thereof; it being understood that the triarylmethane dye(s) (a) and the fluorescent dye(s) (b) are applied to said keratin fibres together or sequentially.

Another subject of the invention is a cosmetic composition comprising:
(a) one or more triarylmethane dyes chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof; and
(b) one or more fluorescent dyes, as defined previously.

The combination of particular triarylmethane dye(s) and of fluorescent dye(s) makes it possible especially to obtain natural colourings that have good dyeing properties, especially in terms of chromaticity, power, intensity, sheen and selectivity.

Furthermore, the process and the composition according to the invention make it possible to dye light keratin materials efficiently in chestnut-brown, dark chestnut-brown, brown, brown with a glint or even black, by mixing direct dyes, and in particular only the dyes (a) and (b) as defined previously, without the need to use an additional (or complementary) dye other than (a) or (b).

Moreover, the colourings obtained by means of the process and the composition according to the invention show good resistance to the various attacking factors to which the hair may be subjected, such as light, bad weather, washing and perspiration. They are in particular persistent with respect to shampooing, especially after at least three shampoo washes.

A subject of the present invention is also a multi-compartment device comprising a first compartment containing one or more triarylmethane dyes (a) chosen from the compounds of formula (I) as defined previously, and also the optical isomers thereof, the geometrical isomers thereof, the tautomers thereof, the organic or mineral acid or base salts thereof, the solvates thereof such as hydrates, and mixtures thereof, and a second compartment containing one or more fluorescent dyes (b) as defined previously.

Another subject of the invention is the use of fluorescent dye(s), as defined previously, combined with triarylmethane dye(s) chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof, for the dyeing of light keratin fibres, especially human keratin fibres such as the hair, in chestnut-brown, dark chestnut-brown, brown, brown with a glint or even black, without using an additional dye other than (a) or (b).

Other subjects, characteristics, aspects and advantages of the invention will emerge even more clearly on reading the description and the examples that follow.

For the purposes of the present invention and unless otherwise indicated:
  the "dyes" according to the invention absorb light in the visible range, i.e. at a wavelength $\lambda_{abs}$ particularly between 400 and 700 nm inclusive;
  for the purposes of the present invention, the term "direct dye" means natural and/or synthetic dyes, which are soluble in the cosmetic medium, other than oxidation dyes; they are dyes which will diffuse superficially on the keratin fibres;
  for the purposes of the present invention, the term "fluorescent dye" means a dye which is a coloured molecule (which absorbs visible light) and which itself imparts colour, and which, in contrast with a conventional dye, transforms the absorbed energy into light of a longer wavelength emitted in the visible part of the spectrum; in particular, the "fluorescent" dyes of the invention are capable of absorbing light in the visible range at a wavelength $\lambda_{abs}$ of between 350 and 800 nm and of re-emitting in the visible range at a longer wavelength $\lambda_{em}$ than that absorbed, of between 400 and 800 nm; the difference between the absorption and emission wavelengths, also known as the Stoke's shift, is between 1 nm and 100 nm. More preferentially, the fluorescent dyes of the invention are dyes that are capable of absorbing at a wavelength $\lambda_{abs}$ of between 420 nm and 550 nm and of re-emitting in the visible range at a wavelength $\lambda_{em}$ of between 470 and 600 nm;
  the "fluorescent dyes" according to the present invention are to be differentiated from optical brighteners. Optical brighteners, also generally known as "brighteners" or "fluorescent brighteners" or "fluorescent brightening agents" or "fluorescent whitening agents or FWA" or "whiteners" or "fluorescent whiteners", are colourless compounds, which do not impart a colour and are consequently not dyes since they do not absorb in the visible light range, but only absorb in the ultraviolet range (wavelength ranging from 200 to 400 nm) and transform the absorbed energy into fluorescent light of a longer wavelength emitted in the visible part of the spectrum in the blue range. The colour impression is then generated only by the purely fluorescent light that is predominantly blue (wavelength ranging from 400 to 500 nm).

the "blue-violet" dyes according to the invention are dyes which absorb light in the visible spectrum and which appear blue visually, i.e. which absorb light at an absorption wavelength $\lambda_{max}$ greater than 550 nm and less than or equal to 700 nm, in particular $\lambda_{max}$ between 560 nm and 700 nm, preferably in the blue range, i.e. $\lambda_{max}$ between 580 and 650 nm the term "(hetero)aryl" means aryl and heteroaryl groups;

the "aryl" or "heteroaryl" radicals or the aryl or heteroaryl part of a radical may be substituted with at least one substituent borne by a carbon atom, chosen from:
- a $C_1$-$C_6$ and preferably $C_1$-$C_4$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
- a halogen atom such as chlorine;
- a hydroxyl or thiol group;
- a $C_1$-$C_6$ alkoxy or $C_1$-$C_6$ alkylthio radical;
- a (poly)hydroxy($C_2$-$C_6$)alkoxy radical;
- an amino radical;
- a 5- or 6-membered heterocycloalkyl radical, preferentially morpholino, piperazino, piperidino or pyrolidino, which is optionally substituted with a ($C_1$-$C_4$) alkyl radical, preferentially methyl;
- a 5- or 6-membered heteroaryl radical, preferentially imidazolyl, optionally substituted with a ($C_1$-$C_4$) alkyl radical, preferentially methyl;
- an amino radical substituted with one or two identical or different $C_1$-$C_6$ alkyl radicals, optionally bearing at least:
  i) a hydroxyl group,
  ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
  iii) a quaternary ammonium group —N$^+$R'R''R''', M$^-$ for which R', R'' and R''', which may be identical or different, represent a $C_1$-$C_4$ alkyl group and M$^-$ represents an anionic counterion,
  iv) or an optionally cationic 5- or 6-membered heteroaryl radical, preferentially imidazolium, optionally substituted with a ($C_1$-$C_4$)alkyl radical, preferentially methyl;
- an acylamino radical (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;
- a carbamoyl radical ((R)$_2$N—C(O)—) in which the R radicals, which may be identical or different, represent a hydrogen atom or a $C_1$-$C_4$ alkyl radical optionally bearing at least one hydroxyl group;
- an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;
- an aminosulfonyl radical ((R)$_2$N—S(O)$_2$—) in which the R radicals, which may be identical or different, represent a hydrogen atom or a $C_1$-$C_4$ alkyl radical optionally bearing at least one hydroxyl group;
- a carboxyl radical in the acid or salified form (preferably salified with an alkali metal or a substituted or unsubstituted ammonium);
- a cyano group;
- a nitro or nitroso group;
- a polyhaloalkyl group, preferably trifluoromethyl;

the cyclic or heterocyclic part of a non-aromatic radical may be substituted with at least one substituent chosen from the following groups:
- hydroxyl;
- $C_1$-$C_4$ alkoxy, $C_2$-$C_4$ (poly)hydroxyalkoxy;
- $C_1$-$C_4$ alkyl;
- alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;
- alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;
- alkoxycarbonyl (R—X—C(O)—) in which the radical R is a $C_1$-$C_4$ alkoxy radical, X is an oxygen atom or an amino group optionally substituted with a $C_1$-$C_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;
- a cyclic or heterocyclic radical, or a non-aromatic part of an aryl or heteroaryl radical, which may also be substituted with one or more oxo groups;
- an "aryl" radical represents a monocyclic or fused or non-fused polycyclic carbon-based group comprising from 6 to 22 carbon atoms, at least one ring of which is aromatic; preferentially, the aryl radical is a phenyl, biphenyl, naphthyl, indenyl, anthracenyl or tetrahydronaphthyl;
- a "cationic heteroaryl radical" is a heteroaryl group as defined previously, which comprises an endocyclic or exocyclic cationic group, when the charge is endocyclic, it is included in the electron delocalization via the mesomeric effect; for example, it is a pyridinium, imidazolium or indolinium group:

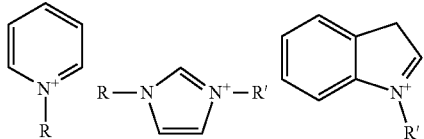

with R and R' being a heteroaryl substituent as defined previously and particularly a (hydroxy)($C_1$-$C_8$)alkyl group, such as methyl;

when the charge is exocyclic, it is not included in the electron delocalization via the mesomeric effect; for example, it is an ammonium or phosphonium substituent R+, such as trimethylammonium, which is outside the heteroaryl, such as pyridyl, indolyl, imidazolyl or naphthalimidyl, in question:

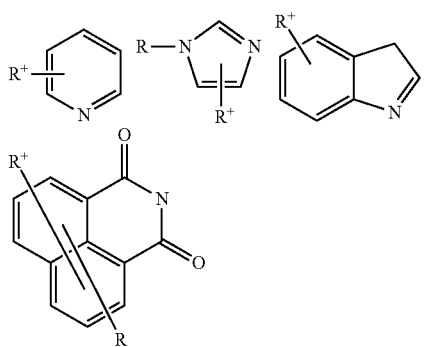

with R being a heteroaryl substituent as defined below and $R^+$ an ammonium $R_aR_bR_cN^+$—, phosphonium $R_aR_bR_cP^+$— or ammonium $R_aR_bR_cN^+$—($C_1$-$C_6$)alkylamino, $R_aR_bR_cN^+$—($C_1$-$C_6$)alkyl or $R_aR_bR_cN^+$—($C_1$-$C_6$)alkoxy group with $R_a$, $R_b$ and $R_c$, which may be identical or different, representing a ($C_1$-$C_8$)alkyl group such as methyl;

a "heteroaryl radical" represents a 5- to 22-membered, monocyclic or fused or non-fused polycyclic group, comprising from 1 to 6 heteroatoms chosen from nitrogen, oxygen and sulfur, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and the ammonium salt thereof;

a "heterocyclic radical" is a radical which may contain one or two unsaturations, but is a monocyclic or fused or non-fused polycyclic, 5- to 22-membered non-aromatic radical comprising from 1 to 6 heteroatoms chosen from nitrogen, oxygen and sulfur;

a "heterocycloalkyl radical" is a heterocyclic radical comprising at least one saturated ring;

an "alkyl radical" is a linear or branched $C_1$ to $C_{20}$, preferably $C_1$ to $C_{10}$, more preferentially $C_1$ to $C_8$, better still $C_1$ to $C_6$ and even better still $C_1$ to $C_4$ hydrocarbon-based radical;

the expression "optionally substituted" applied to the alkyl radical implies that said alkyl radical may be substituted with one or more radicals chosen from the following radicals: i) hydroxyl, ii) $C_1$-$C_4$ alkoxy, iii) R—Z—C(X)—Y— with X, Y and Z representing an oxygen or sulfur atom or N(R'), or alternatively X and/or Z represent a bond, R and R', which may be identical or different, represent a hydrogen atom or a ($C_1$-$C_6$)alkyl group, preferably, X represents an oxygen atom, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom; v) or a quaternary ammonium group $N^+R'R''R'''$, $M^-$ for which R', R'' and R''', which may be identical or different, represent a $C_1$-$C_4$ alkyl group, or alternatively —$N^+R'R''R'''$ forms a heteroaryl such as imidazolium optionally substituted with a $C_1$-$C_4$ alkyl group and $M^-$ represents the anionic counterion, vi) carboxyl C(O)OH, vii) carboxylate $C(O)O^-$, $M^+$ with $M^+$ representing a cationic counterion such as alkali metal or alkaline-earth metal, viii) sulfonic —$SO_3H$, ix) sulfonate —$SO_3^-$, $M^+$ with $M^+$ as defined previously, and x) cyano;

an "alkoxy radical" is an alkyl-oxy radical for which the alkyl radical is a linear or branched $C_1$-$C_8$ and preferentially $C_1$-$C_6$ hydrocarbon-based radical;

when the alkoxy group is optionally substituted, this implies that the alkyl group is optionally substituted as defined above;

the term "organic or mineral acid salt" more particularly means the salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion" means an anion or an anionic group derived from an organic or mineral acid which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O$^-$ such as methylsulfonate or mesylate and ethylsulfonate; iv) arylsulfonates: Ar—S(O)$_2$O$^-$ such as benzenesulfonate and toluenesulfonate or tosylate; v) carboxylates Alk-C(O)—OH with Alk representing a ($C_1$-$C_6$)alkyl group optionally substituted with one or more hydroxyl or carboxylate groups such as citrate; vi) succinate; vii) tartrate; viii) lactate; ix) alkyl sulfates: Alk-O—S(O)O$^-$ such as methyl sulfate and ethyl sulfate; x) aryl sulfates: Ar—O—S(O)O$^-$ such as benzene sulfate and toluene sulfate; xi) alkoxy sulfates:

Alk—O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$. O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, and xvii) sulfate (O=)$_2$S(O$^-$)$_2$ or SO$_4^{2-}$ and hydrogen sulfate HSO$_4^-$;

the anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a dye which contains two cationic groups may contain either two "singly charged" anionic counterions or a "doubly charged" anionic counterion such as (O=)$_2$S(O$^-$)$_2$ or O=P(O$^-$)$_2$—OH;

in particular, the anionic counterions are chosen from halides such as chloride, bromide, fluoride or iodide; a hydroxide; a sulfate; a hydrogen sulfate; a linear or branched C$_1$-C$_6$ alkyl sulfate, such as the methylsulfate or ethylsulfate ion; carbonates and hydrogen carbonates; carboxylic acid salts such as formate, acetate, citrate, tartrate and oxalate; linear or branched C$_1$-C$_6$ alkylsulfonates, such as the methylsulfonate ion; arylsulfonates for which the aryl part, preferably phenyl, is optionally substituted with one or more C$_1$-C$_4$ alkyl radicals, for instance 4-tolylsulfonate; and alkylsulfonyls such as mesylate;

the term "chemical oxidizing agent" means any oxidizing agent other than atmospheric oxygen conventionally used in the field. Thus, mention may be made of hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. Preferably, the chemical oxidizing agent is hydrogen peroxide.

Moreover, the addition salts that may be used in the context of the invention are especially chosen from salts of addition with a cosmetically acceptable base such as the basifying agents as defined below, for instance alkali metal hydroxides, such as sodium hydroxide or potassium hydroxide, aqueous ammonia, amines or alkanolamines;

the expression "at least one" is equivalent to "one or more";

the limits of a range of values are included in that range, in particular in the expressions "between" and "ranging from . . . to . . . "; and the expression "inclusive" for a range of values means that the limits of that range are included in the defined range.

(a) Triarylmethane Dyes

The process for dyeing keratin fibres and the cosmetic composition according to the present invention use, or comprise, (a) one or more triarylmethane dyes chosen from the compounds of formula (I), as defined previously, the optical isomers thereof, the geometrical isomers thereof, the tautomers thereof, the organic or mineral acid or base salts thereof, the solvates thereof such as hydrates, and mixtures thereof.

In particular, the dyes of formula (I) are blue, violet or green, and dull or chromatic.

Preferably, R$_1$, R$_2$, R'$_1$ and R'$_2$, which may be identical or different, represent, independently of each other:
a hydrogen atom,
a linear or branched C$_1$ to C$_6$ alkyl radical, which is optionally substituted, and/or optionally interrupted with one or more heteroatoms chosen from oxygen and sulfur, and/or with one or more groups comprising at least one heteroatom, preferably chosen from oxygen, sulfur, C(O), SO, SO$_2$ and SO$_3^-$, or combinations thereof, preferably an unsubstituted linear or branched C$_1$ to C$_6$ alkyl radical, and more preferentially an unsubstituted linear or branched C$_1$ to C$_4$ alkyl radical, or
a benzyl radical substituted with an SO$_3^-$ group.

Preferably, n and m, which may be identical or different, represent two integers ranging from 0 to 2. According to a particular embodiment, n and m are identical and are equal to 0.

Preferably, R$_5$ represents:
a hydrogen atom,
an SO$_3^-$ group, or
a radical —NR$_6$R$_7$, with R$_6$ and R$_7$, which may be identical or different, representing, independently of each other, a hydrogen atom or a linear or branched C$_1$ to C$_6$ alkyl radical, and preferably a C$_1$ to C$_4$ alkyl radical, such as a methyl or ethyl radical.

The triarylmethane dye(s) chosen from the compounds of formula (I) of the invention, as defined previously, the optical isomers thereof, the geometrical isomers thereof, the tautomers thereof, the organic or mineral acid or base salts thereof, the solvates thereof such as hydrates, and mixtures thereof, may be cationic, anionic or nonionic.

According to a particular embodiment of the invention, the triarylmethane dye(s) are cationic (i.e. they comprise an ammonium group on the phenyl group A) and are chosen from the compounds of formula (I-cat), they may comprise an anion An$^-$ as defined previously to counterbalance the cationic charge.

Another variant is that the dye(s) of formula (I-cat) comprise a radical comprising a sulfate radical SO$^{3-}$ on one of the rings A, B or C, in which case the dyes of formula (I) may not comprise an anion An$^-$ or cation M$^+$, the sulfonate group electro-compensating for the cationic charge of the ammonium (zwitterionic dye).

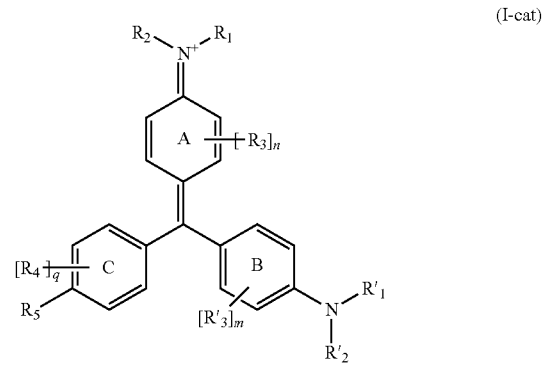
(I-cat)

in which formula (I-cat):
R$_1$ to R$_5$, and R'$_1$ to R'$_3$, m, n and q are as defined previously;
it being understood that (I-cat) does not comprise more than one sulfonate group.

According to another particular embodiment of the invention, the triarylmethane dye(s) are anionic (i.e. either they comprise an ammonium group attached to phenyl A and at least two sulfonate groups $SO^{3-}$ on ring A, B or C; or they do not comprise an ammonium group on A and comprise at least one sulfonate group $SO^{3-}$ on one of the rings A, B or C) and are chosen from the compounds of formula (I-an') or (I-an"), the dyes then comprise one or more cations $M^+$ as defined previously to counterbalance the anionic charge(s):

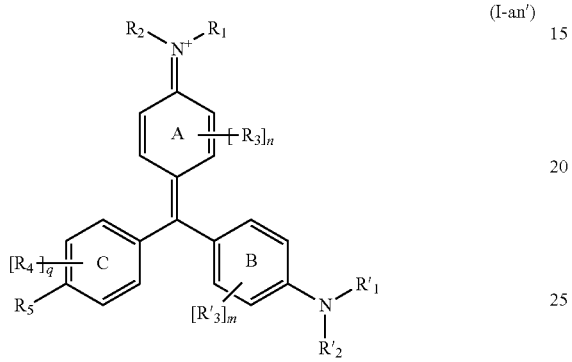

(I-an')

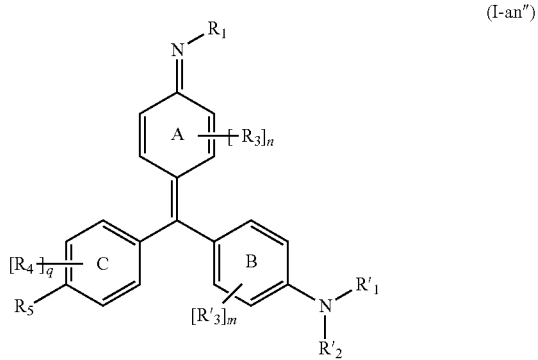

(I-an")

in which formula (I-an') or (I-an"):

$R_1$ to $R_5$, and $R'_1$ to $R'_3$, m, n and q are as defined previously;

it being understood that:

(I-an') comprises at least two sulfonate groups on ring A, B or C, (I-an") comprises at least one sulfonate group on ring A, B or C, and one or more cation(s) $M^+$ as defined previously are present to compensate for the anionic charge(s) of the sulfonate group(s).

According to yet another particular embodiment of the invention, the triarylmethane dye(s) are nonionic (i.e. they do not comprise an ammonium group attached to phenyl A or a sulfonate group $SO^{3-}$) and are chosen from the compounds of formula (I-nion):

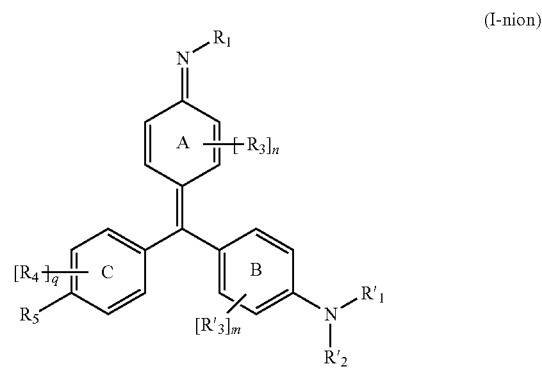

(I-nion)

in which formula (I-nion):

$R_1$ to $R_5$, and $R'_1$ to $R'_3$, m, n and q are as defined previously, it being understood that (I-nion) does not comprise any sulfonate groups on ring A, B or C.

According to a particular embodiment of the invention, $An^-$ denotes an anion, chosen from halide ions such as bromide or chloride, methylsulfate, toluenesulfonate or a mixture of these ions, and more preferentially $An^-$ denotes a chloride.

According to a particular embodiment of the invention, $M^+$ is chosen from sodium, potassium, magnesium and calcium, preferably potassium.

According to a third particular embodiment of the invention, the dye(s) of formula (I) comprise one or more solvates and are preferably chosen from hydrochloride and phosphonate.

Preferably, the triarylmethane dye(s) are chosen from the following compounds, the optical isomers thereof, the geometrical isomers thereof, the tautomers thereof, the organic or mineral acid or base salts thereof, the solvates thereof such as hydrates, and mixtures thereof:

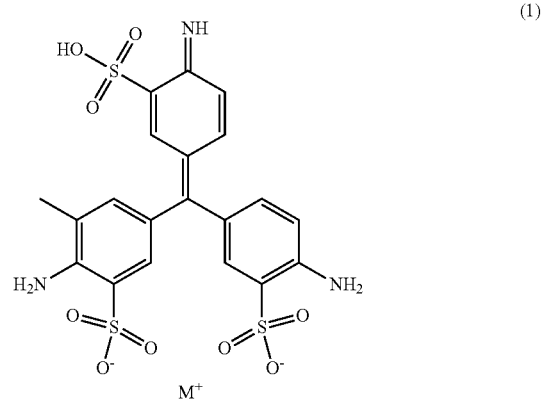

(1)

-continued
(2)
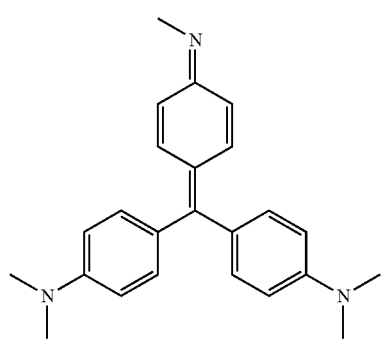
(1')
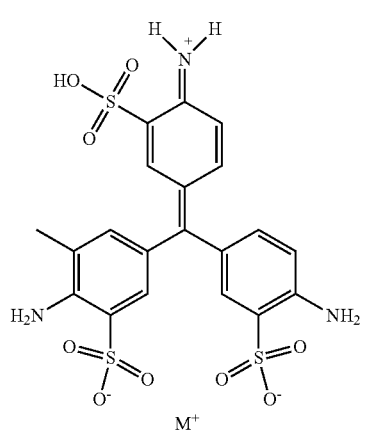
(2')
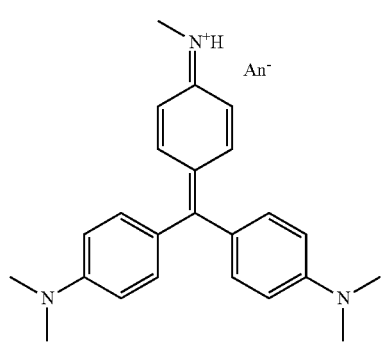
(3)
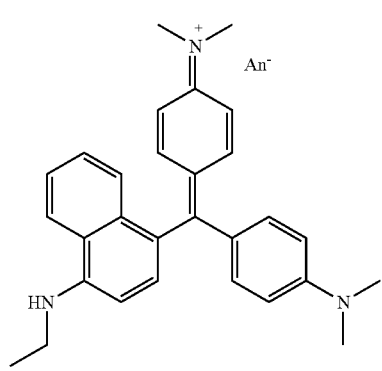
-continued
(4)
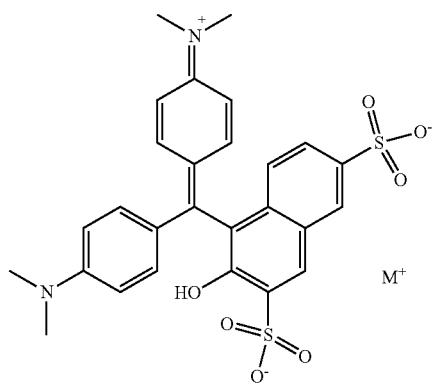
(5)
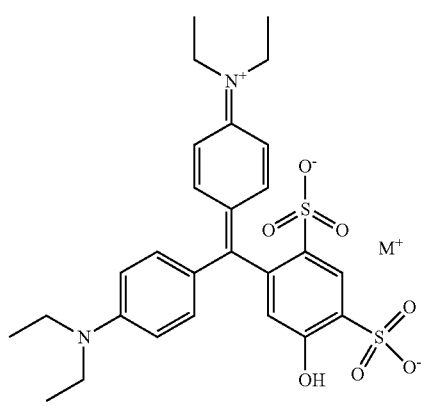
(6)
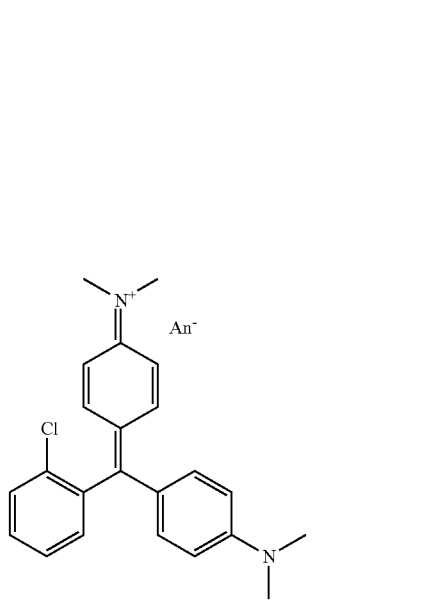

(7) 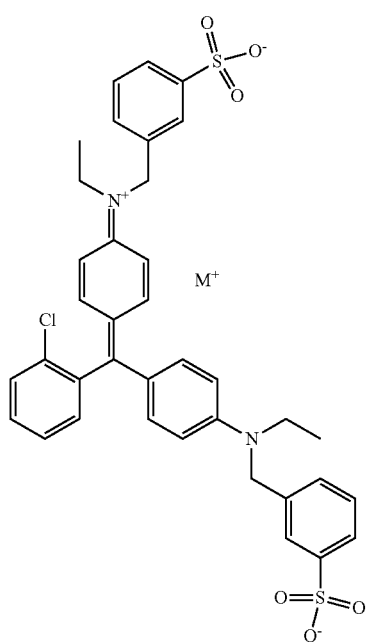
(8) 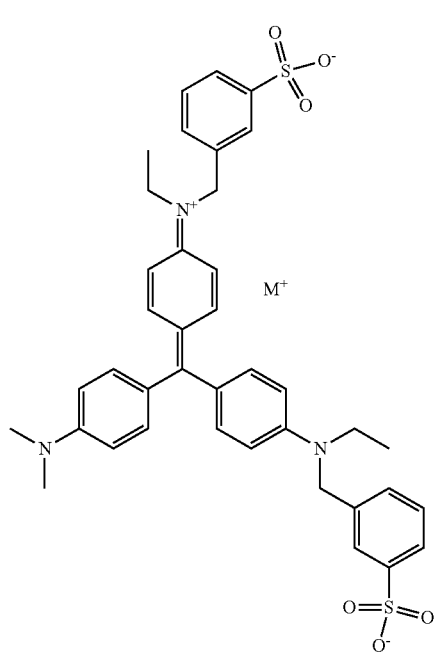
(9) 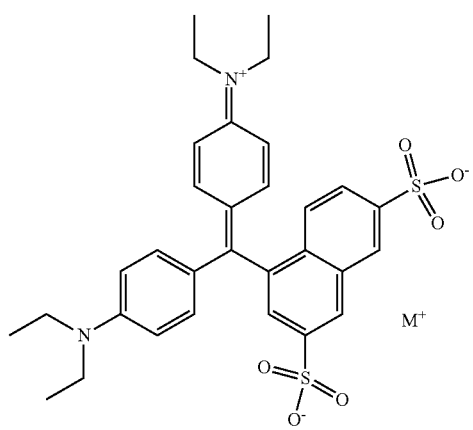
(10) 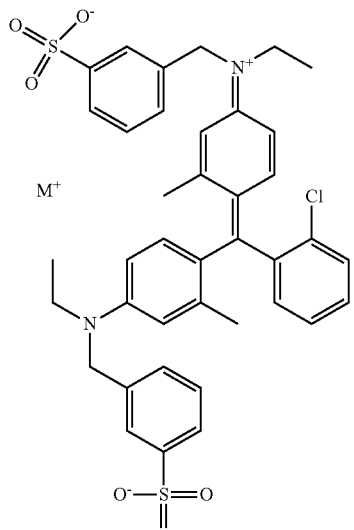
(11) 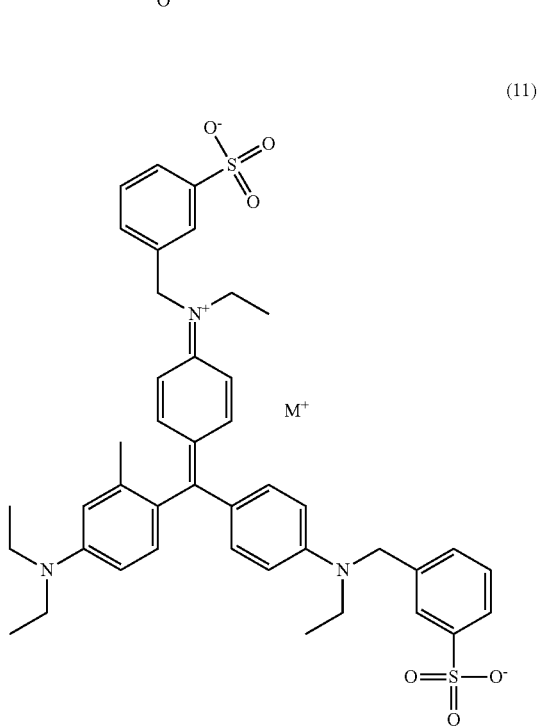

(12)

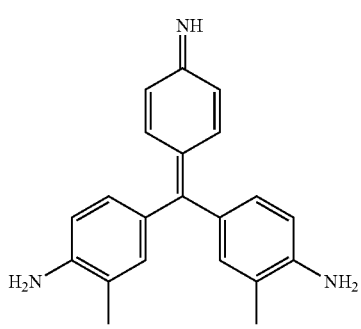

(13)

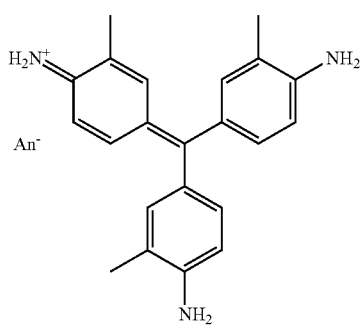

(14)

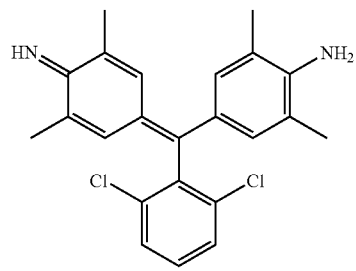

(15)

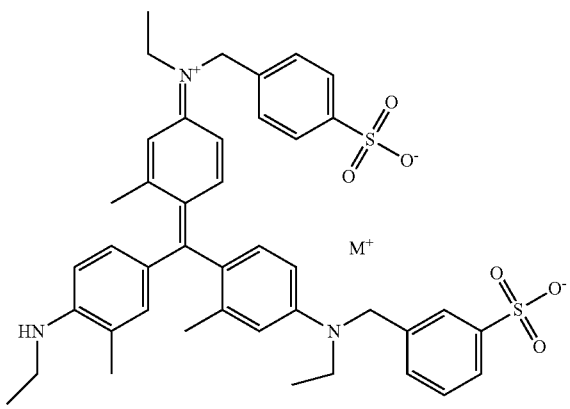

Y being as defined previously.

More preferentially, the triarylmethane dye(s) are chosen from compounds 1a to 14a below, the optical isomers thereof, the geometrical isomers thereof, the tautomers thereof, the organic or mineral acid or base salts thereof, the solvates thereof such as hydrates, and mixtures thereof:

| Commercial name | Compound |
|---|---|
| Acid Magenta Calcium Salt | (structure shown) |

1a

-continued
| Commercial name | Compound |
|---|---|
| Solvent Violet 8 | 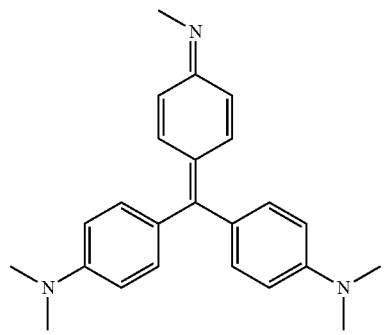<br>2a |
| CI Basic Blue 11 | 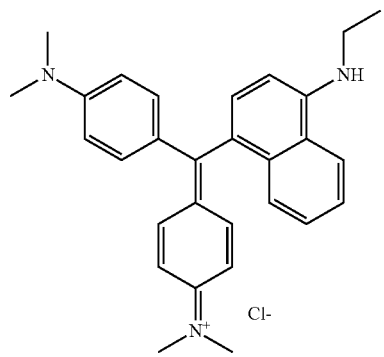<br>3a |
| Wool Green S CI 44090 | 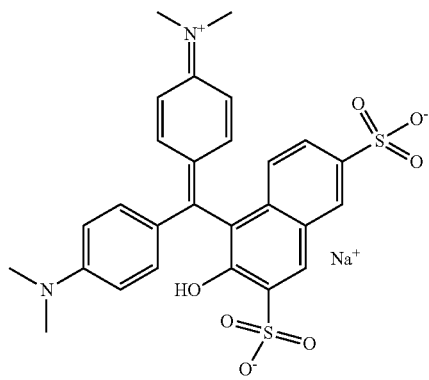<br>4a |

| Commercial name | Compound |
|---|---|
| Disulfine Blue | 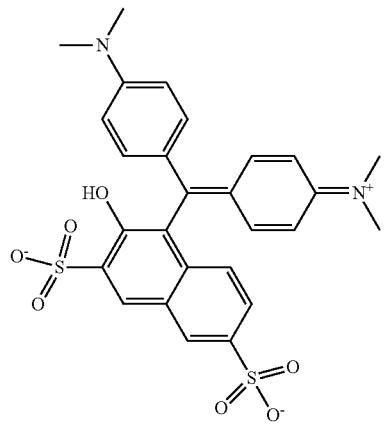 Ca²⁺ |
| | 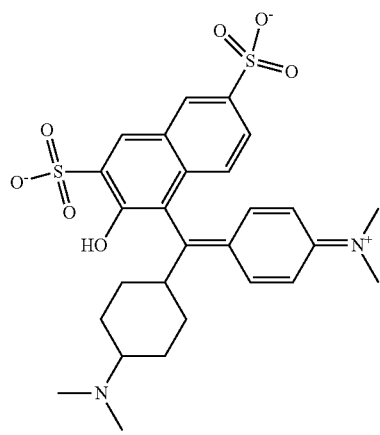 5a |
| Primocyanine 6GX | 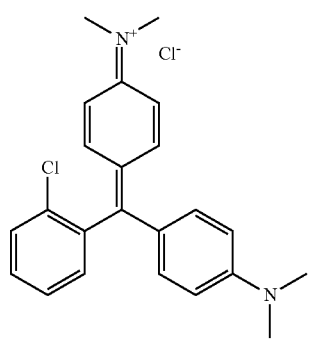 6a |

| Commercial name | Compound |
|---|---|
| Brilliant Acid Green | 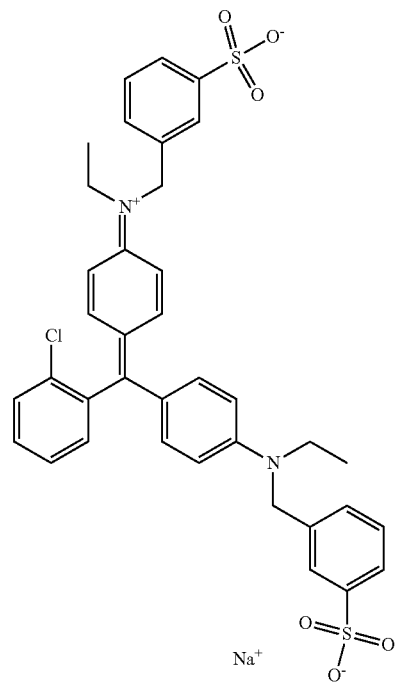<br>7a |
| Coomassie Violet | 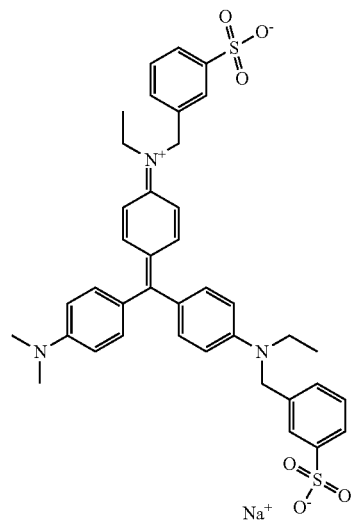<br>8a |

| Commercial name | Compound |
|---|---|
| Lissamine Green V | 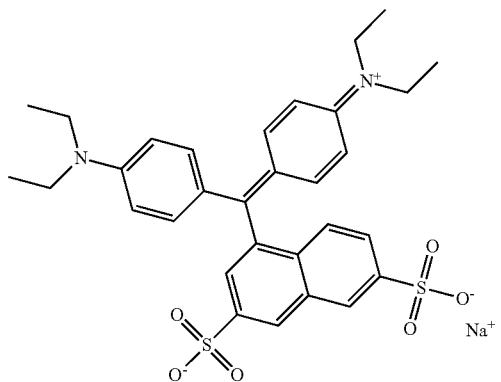<br>9a |
| Alkali Fast Green 10GA 1293 | 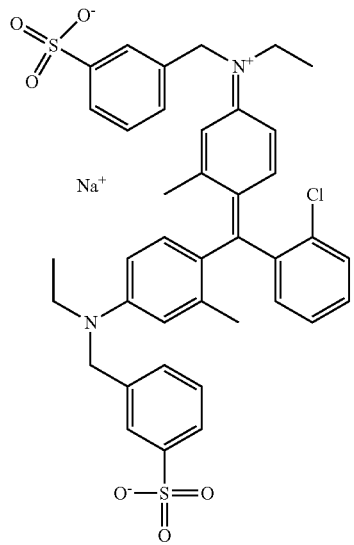<br>10a |

| Commercial name | Compound |
|---|---|
| Coomassie Brilliant Blue FF | 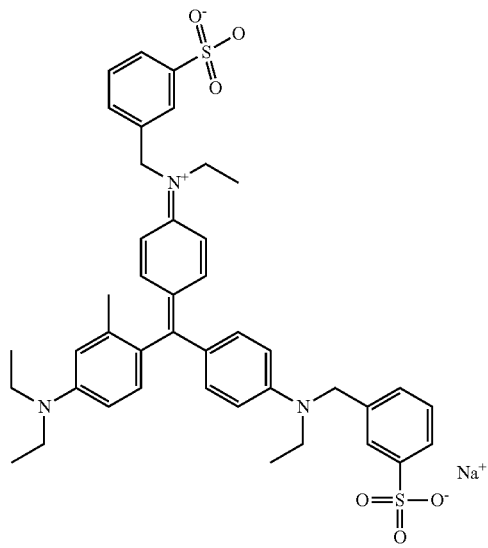<br>11a |
| Carbolfuchsin | 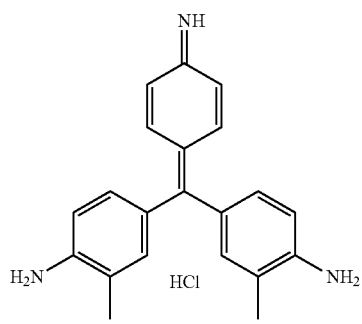<br>11a |
| Brilliant Blue G | 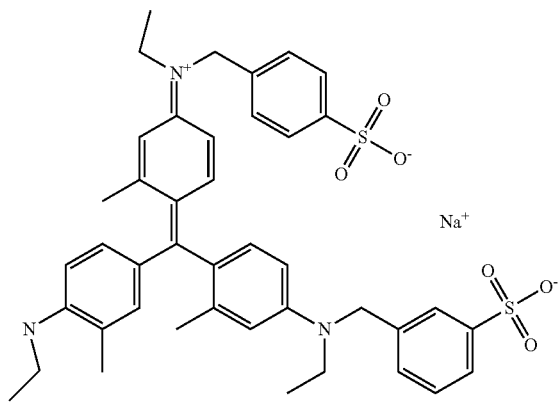<br>12a |

| Commercial name | Compound |
|---|---|
| HCBlue 15 | 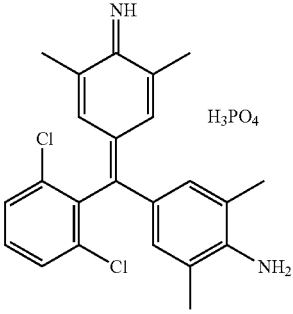<br>13a |
| Basic Violet 2 | 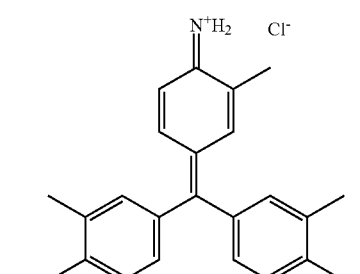<br>14a |

According to a first particular embodiment:
$R_1$, $R_2$, $R'_1$ and $R'_2$, which may be identical or different, represent, independently of each other:
 a hydrogen atom,
 an unsubstituted, linear or branched $C_1$ to $C_6$ alkyl radical, and more preferentially an unsubstituted, linear or branched $C_1$ to $C_4$ alkyl radical, such as a methyl or ethyl radical,
 a benzyl radical substituted with an $SO_3^-$ group;
n and m are identical and equal to 0;
the radicals $R_4$, which may be identical or different, represent, independently of each other:
 a linear or branched $C_1$ to $C_6$ alkyl radical, preferably a linear or branched $C_1$ to $C_4$ alkyl radical, such as a methyl radical,
 a hydroxyl radical,
 an $SO_3^-$ group,
 a halogen atom, preferably a chlorine atom,
 or alternatively two adjacent radicals $R_4$ together form a benzo ring, optionally substituted with an $SO_3^-$ group;
q is an integer ranging from 0 to 4; and
$R_5$ represents:
 a hydrogen atom,
 an $SO_3^-$ group,
 a radical —$NR_6R_7$, with $R_6$ and $R_7$, which may be identical or different, representing, independently of each other, a linear or branched $C_1$ to $C_6$ alkyl radical, and preferably a $C_1$ to $C_4$ alkyl radical, such as a methyl or ethyl radical.

According to a second particular embodiment:
$R_1$, $R_2$, $R'_1$ and $R'_2$, which may be identical or different, represent, independently of each other:
 a hydrogen atom,
 an unsubstituted, linear or branched $C_1$ to $C_6$ alkyl radical, and more preferentially an unsubstituted, linear or branched $C_1$ to $C_4$ alkyl radical, such as a methyl or ethyl radical,
 a benzyl radical substituted with an $SO_3^-$ group;
n and m, which may be identical or different, are equal to 1 or 2;
$R_3$ and $R'_3$, which may be identical or different, represent, independently of each other:
 a linear or branched $C_1$ to $C_4$ alkyl radical, preferably a methyl radical,
 an $SO_3^-$ group,
the radicals $R_4$, which may be identical or different, represent, independently of each other:
 a linear or branched $C_1$ to $C_6$, preferably linear or branched $C_1$ to $C_4$, alkyl radical, such as a methyl radical,
 an $SO_3^-$ group,
 a halogen atom, preferably a chlorine atom,
q is an integer equal to 1 or 2; and
$R_5$ represents:
 a hydrogen atom,
 an $SO_3^-$ group,
 a radical —$NR_6R_7$, with $R_6$ and $R_7$, which may be identical or different, representing, independently of each other, a hydrogen atom or a linear or branched $C_1$ to $C_6$ alkyl radical, and preferably a $C_1$ to $C_4$ alkyl radical, such as a methyl or ethyl radical.

Preferably, the triarylmethane dye(s) are chosen from compounds 1 to 15, as defined previously, the optical isomers thereof, the geometrical isomers thereof, the tautomers thereof, the organic or mineral acid or base salts thereof, the solvates thereof such as hydrates, and mixtures thereof; and more preferentially from compounds 1a to 14a, as defined previously, the optical isomers thereof, the geometrical isomers thereof, the tautomers thereof, the organic or mineral acid or base salts thereof, the solvates thereof such as hydrates, and mixtures thereof.

(b) Fluorescent Dyes

The process for dyeing keratin fibres and the composition according to the present invention also use, or comprise, (b) one or more fluorescent dyes; said fluorescent dyes being direct dyes chosen from cyanin dyes, styryl/hemicyanin dyes, naphthalimide dyes, and mixtures thereof.

More particularly, the fluorescent dye(s) of the invention are other than fluorescent dyes comprising a disulfide bond. More preferentially, the fluorescent dye(s) of the invention are direct dyes and do not comprise a bond containing contiguous identical heteroatoms.

Mention may also be made of the fluorescent dyes described in EP 1 133 975, WO 03/029 359, EP 860 636, WO 95/01772, WO 95/15144, EP 714 954 and those listed in the encyclopaedia *The chemistry of synthetic dyes* by K. Venkataraman, 1952, Academic Press, vol. 1 to 7, in *Kirk Othmer's encyclopaedia Chemical Technology*, in the chapter "Dyes and Dye Intermediates", 1993, Wiley and Sons, and in various chapters of *Ullmann's Encyclopedia of Industrial Chemistry* 7th edition, Wiley and Sons, especially in *Ullmann's Encyclopedia of Industrial Chemistry* in the chapter "Fluorescent Dyes", 2005, Wiley-VCH Verlag GmbH & Co. KGaA, Weinheim 10.1002/143560007.a11_279; in *The Handbook —A Guide to Fluorescent Probes and Labeling Technologies*, 10th Ed Molecular Probes/Invitrogen—Oregon 2005 circulated by Internet or in the preceding printed editions.

Preferably, the fluorescent dye(s) of the invention are cationic.

More preferentially, the fluorescent dyes are direct and cationic; and better still, the fluorescent dye(s) (b) are chosen from styryl or hemicyanin cationic dyes.

Better still, the fluorescent dyes of the invention absorb light in the yellow, orange and red range, preferably in the absorption wavelength $\lambda_{abs}$ between 400 nm and 500 nm inclusive.

According to one variant, the fluorescent dyes of the invention contain at least one cationic radical borne by, or included in, at least one of the fluorescent chromophores.

Preferably, the cationic radical is a quaternary ammonium; better still, the cationic charge is endocyclic.

These cationic radicals are, for example, a cationic radical:

bearing an exocyclic (di/tri)($C_1$-$C_8$)alkylammonium charge, or bearing an endocyclic charge, such as the following cationic heteroaryl groups: acridinium, benzimidazolium, benzobistriazolium, benzopyrazolium, benzopyridazinium, benzoquinolium, benzothiazolium, benzotriazolium, benzoxazolium, bipyridinium, bistetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

According to a preferred variant of the invention, the fluorescent dyes of the invention bear at least one cationic chromophore and comprise at least one quaternary ammonium radical such as polymethine chromophores chosen from formulae (III) and (IV) below:

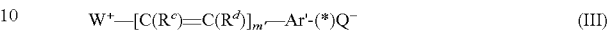

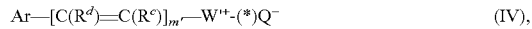

in which formulae (III) and (IV):

W⁺ represents a cationic heteroaryl group, in particular comprising a quaternary ammonium optionally substituted with one or more ($C_1$-$C_8$)alkyl groups optionally substituted in particular with one or more hydroxyl groups;

W'⁺ represents a divalent heteroaryl radical as defined for W⁺;

Ar represents an aryl group such as phenyl or naphthyl, optionally substituted preferably with i) one or more halogen atoms such as chlorine or fluorine; ii) one or more ($C_1$-$C_8$)alkyl and preferably $C_1$-$C_4$ alkyl groups such as methyl; iii) one or more hydroxyl groups; iv) one or more ($C_1$-$C_8$)alkoxy groups such as methoxy; v) one or more hydroxy($C_1$-$C_8$)alkyl groups such as hydroxyethyl, vi) one or more amino or (di)($C_1$-$C_8$) alkylamino groups, preferably with the $C_1$-$C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

Ar' is a divalent aryl radical as defined for Ar;

m' represents an integer between 1 and 4 inclusive, in particular, m' is 1 or 2; better still 1;

$R^c$ and $R^d$, which may be identical or different, represent a hydrogen atom or optionally a substituted ($C_1$-$C_8$) alkyl and preferably $C_1$-$C_4$ alkyl group, or alternatively $R^c$ is contiguous with W or W' and/or $R^d$ is contiguous with Ar or Ar' and form, with the atoms that bear them, a (hetero)cycloalkyl; in particular, $R^c$ is contiguous with W⁺ or W'⁺ and forms a (hetero)cycloalkyl such as cyclohexyl;

Q⁻ is an organic or mineral anionic counterion;

(*) represents the part of the fluorescent chromophore that is bonded to the rest of the dye.

Preferably, W⁺ or W'⁺ is an imidazolium, pyridinium, benzimidazolium, pyrazolium, benzothiazolium or quinolinium radical optionally substituted with one or more identical or different $C_1$-$C_4$ alkyl radicals.

According to a particularly preferred embodiment of the invention, the fluorescent chromophore(s) of the dyes (III) or (IV) are those defined previously with m'=1, Ar representing a phenyl group substituted para to the styryl group —C($R^d$)=C($R^c$)— with a (di)(hydroxy)($C_1$-$C_6$)(alkyl)amino group such as dihydroxy($C_1$-$C_4$)alkylamino, and W'⁺ representing an imidazolium or pyridinium group, preferentially ortho- or para-pyridinium.

According to another preferred variant of the invention, the fluorescent chromophore(s) of the dyes are cationic and comprise at least one quaternary ammonium radical such as a naphthimidyl bearing a cationic exocyclic charge of formula (IIIa) or (IVa):

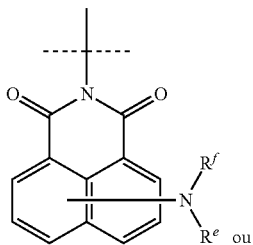

(IIIa)

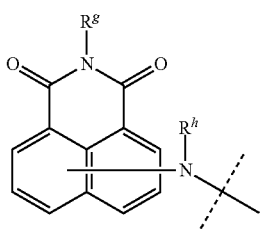

(IVa)

where ⊢ represents the bond with the dye in which formulae (IIIa) and (IVa) $R^e$, $R^f$, $R^g$ and $R^h$, which may be identical or different, represent a hydrogen atom or a ($C_1$-$C_6$)alkyl group which is optionally substituted, preferentially with a di($C_1$-$C_6$)alkylamino or tri($C_1$-$C_6$)alkylammonium group such as trimethylammonium.

According to a particular embodiment, the fluorescent dye(s) (b) of the invention are chosen from those of formula (V), (VI) or (VII) below, and also the organic or mineral acid or base salts thereof, the optical isomers, geometrical isomers and tautomers thereof, and the solvates thereof such as hydrates:

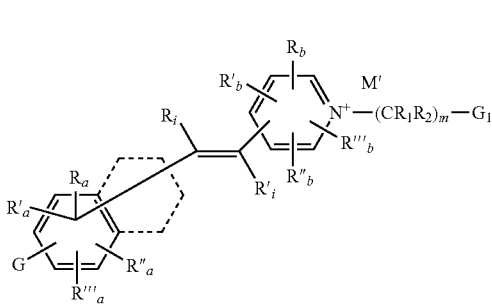

(V)

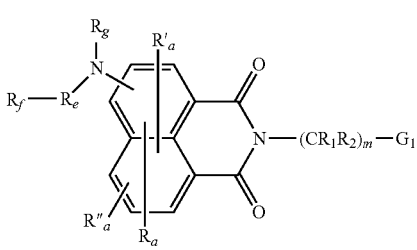

(VI)

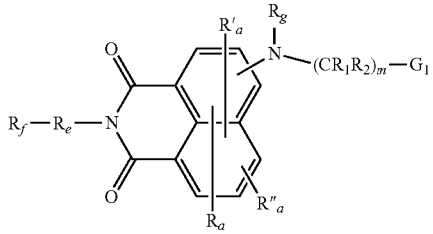

(VII)

in which formulae (V), (VI) and (VII):

$R_1$ and $R_2$, which may be identical or different, represent a hydrogen atom or a $C_1$-$C_6$ alkyl group; preferentially a hydrogen atom;

$G_1$ represents a hydrogen atom or a group chosen from $NH_2$ and OH;

$R_a$, $R'_a$, $R''_a$, $R'''_a$, $R_b$, $R'_b$, $R''_b$ and $R'''_b$, which may be identical or different, represent a) a hydrogen atom, b) a halogen atom, a group from among: c) amino, d) ($C_1$-$C_4$)alkylamino, e) ($C_1$-$C_4$)dialkylamino, f) cyano, g) carboxyl —C(O)OH or carboxylate —C(O)O$^-$, Q$^+$, h) hydroxyl —OH or alkoxide —O$^-$Q$^+$, i) (poly)halo ($C_1$-$C_6$)alkyl such as trifluoromethyl, j) acylamino, k) ($C_1$-$C_6$)alkoxy, l) ($C_1$-$C_6$)alkylthio, m) (poly)hydroxy ($C_2$-$C_4$)alkoxy, n) ($C_1$-$C_6$)alkylcarbonyloxy, o) ($C_1$-$C_6$) alkoxycarbonyl, p) ($C_1$-$C_6$)alkylcarbonylamino, q) acylamino, r) carbamoyl, s) ($C_1$-$C_6$)alkylsulfonylamino, t) aminosulfonyl, u) —$SO_3H$ or sulfonate —$SO_3^-$, Q$^+$ or v) ($C_1$-$C_6$)alkyl optionally substituted with a group chosen from ($C_1$-$C_6$)alkoxy, hydroxyl, cyano, carboxyl, amino, (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom; in particular, $R_a$, $R'_a$, $R''_a$, $R'''_a$, $R_b$, $R'_b$, $R''_b$ and $R'''_b$ represent a hydrogen or halogen atom or a ($C_1$-$C_4$)alkyl group, preferably a hydrogen atom;

or alternatively two groups $R_a$ and $R'_a$; $R_b$ and $R'_b$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, ($C_1$-$C_4$)alkylamino, ($C_1$-$C_4$) dialkylamino, nitro, cyano, carboxyl, hydroxyl or trifluoromethyl group, an acylamino, ($C_1$-$C_4$)alkoxy (poly)hydroxy($C_1$-$C_4$)alkoxy, ($C_1$-$C_4$)alkylcarbonyloxy, ($C_1$-$C_4$)alkoxycarbonyl or ($C_1$-$C_4$)alkylcarbonylamino radical, an acylamino, carbamoyl or alkoxyalkylsulfonylamino radical, an aminosulfonyl radical, or a ($C_1$-$C_6$)alkyl radical optionally substituted with: a group chosen from ($C_1$-$C_6$)alkoxy, hydroxyl, cyano, carboxyl, amino, ($C_1$-$C_4$)alkylamino and ($C_1$-$C_4$)dialkylamino, or alternatively the two alkyl radicals borne by the nitrogen atom of the amino group form a 5- to 7-membered heterocycle optionally comprising another nitrogen or non-nitrogen heteroatom; preferentially, $R_a$ and $R'_a$ together form a benzo group;

or alternatively, two groups $R_i$ and $R_a$; and/or a group $R'_i$ and $R'_a$ together form a fused (hetero)cycloalkyl, preferentially cycloalkyl such as cyclohexyl;

$R_g$ represents a hydrogen atom, a (hetero)aryl($C_1$-$C_4$) alkyl group or a ($C_1$-$C_6$)alkyl group that is optionally substituted; preferentially, $R_b$ represents a hydrogen atom or a $(C_1-C_3)$alkyl or benzyl group;

$R_e$ represents a covalent bond, a linear or branched, optionally substituted $(C_1-C_8)$alkylene or $(C_2-C_8)$alkenylene hydrocarbon-based chain, preferably $R_e$ represents an unsubstituted $(C_1-C_6)$alkylene;

$R_f$ represents a hydrogen atom, a $(C_1-C_4)$alkoxy group, an amino group $R_3R_4N$—, a quaternary ammonium group M', $R_3R_4R_5N^+$— in which $R_3$, $R_4$ and $R_5$, which may be identical or different, represent a $(C_1-C_4)$alkyl group or $R_3R_4N$-represents an optionally substituted heteroaryl group, preferentially an optionally substituted imidazolyl group, or alternatively M', $R_3R_4R_5N^+$— represents an optionally substituted cationic heteroaryl group, preferentially an imidazolinium group optionally substituted with a $(C_1-C_3)$alkyl group;

G represents i) a group —$NR_cR_d$, ii) —OR with R representing a) a hydrogen atom, b) an optionally substituted, preferentially unsubstituted $(C_1-C_6)$alkyl group, c) an optionally substituted (hetero)aryl group, d) an optionally substituted (hetero)aryl$(C_1-C_6)$alkyl group such as benzyl, e) optionally substituted (hetero)cycloalkyl, f) optionally substituted (hetero)cycloalkyl$(C_1-C_6)$alkyl; according to a particular embodiment, G represents a group —$NR_cR_d$, according to another particular embodiment, G represents a $(C_1-C_6)$alkoxy group;

or alternatively when G represents —$NR_cR_d$, two groups $R_c$ and $R'_a$ and/or $R_d$ and $R_a$ together form a saturated heteroaryl or heterocycle, optionally substituted with one or more $(C_1-C_6)$alkyl groups, preferentially a 5- to 7-membered heterocycle containing one or two heteroatoms chosen from nitrogen and oxygen; more preferentially, the heterocycle is chosen from morpholinyl, piperazinyl, piperidyl and pyrrolidinyl groups;

$R_c$ and $R_d$, which may be identical or different, represent a hydrogen atom or a group from among: a) optionally substituted (hetero)aryl such as phenyl, b) optionally substituted (hetero)aryl$(C_1-C_4)$alkyl, c) optionally substituted (hetero)cycloalkyl, d) optionally substituted (hetero)cycloalkyl$(C_1-C_4)$alkyl, f) $(C_2-C_5)$alkyl or g) $(C_1-C_8)$alkyl which is optionally substituted, preferably optionally substituted with a hydroxyl, carboxyl, carboxylate, sulfate or sulfonate group;

or alternatively two adjacent radicals $R_c$ and $R_d$ borne by the same nitrogen atom together form an optionally substituted heterocyclic or optionally substituted heteroaryl group;

$R_i$ and $R'_i$, which may be identical or different, represent a hydrogen atom or a $(C_1-C_4)$alkyl group;

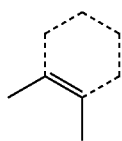

represents a (hetero)aryl group fused to the phenyl ring; or alternatively is absent from the phenyl; preferentially, when the ring is present, the ring is a benzo;

m represents an integer between 1 and 18 inclusive, particularly an integer between 1 and 14 inclusive; preferentially an integer between 2 and 10 inclusive; more preferably an integer between 3 and 8; more particularly an integer between 4 and 6;

M' represents an anionic counterion, derived from a salt of an organic or mineral acid, or from an organic or mineral base that ensures the electrical neutrality of the dye;

$Q^+$ represents a cationic counterion, derived from a salt of an organic or mineral acid, or from an organic or mineral base that ensures the electrical neutrality of the dye such as alkali metal, alkaline-earth metal or ammonium;

it being understood that when the dye comprises a carboxylate, sulfonate or alkoxide group, then M' and $Q^+$ may be absent to ensure the electrical neutrality of said dye.

According to one embodiment, the fluorescent dyes of the invention are of formula (V) as defined previously.

According to a preferred embodiment, the fluorescent dye(s) of the invention are chosen from the styryl dyes of formula (VIII) below, and also the organic or mineral acid or base salts thereof, the optical isomers, geometrical isomers and tautomers thereof, and the solvates thereof such as hydrates:

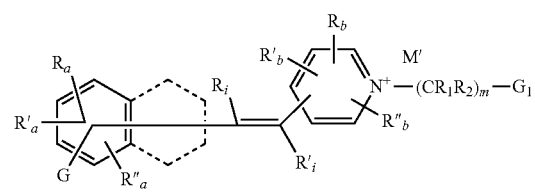

(VIII)

in which formula (VIII) G, $G_1$, $R_a$, $R'_a$, $R''_a$, $R_b$, $R'_b$, $R''_b$, $R_i$, $R'_i$, $R_1$, $R_2$ and m are as defined previously for (V).

In particular, the dye(s) of the invention are chosen from those of formula (VIII) for which:

$R_1$ and $R_2$, which may be identical or different, represent a hydrogen atom;

$R_i$ and $R'_i$, which may be identical or different, represent a hydrogen atom or a $(C_1-C_4)$alkyl group, preferably hydrogen;

$R_a$, $R'_a$ and $R''_a$, which may be identical or different, represent a hydrogen atom, a halogen atom such as fluorine, or an —OH, —$O^-Q^+$, $(C_1-C_6)$alkoxy, nitro, or cyano group, with $Q^+$ as defined previously;

$R_b$, $R'_b$ and $R''_b$, which may be identical or different, represent a hydrogen atom or a $(C_1-C_6)$alkyl group;

or alternatively two contiguous radicals $R_b$ and $R'_b$ form, together with the carbon atoms that bear them, a benzo group that is condensed or fused to the pyridinium group, said benzo group possibly being substituted; preferably, said benzo group is unsubstituted;

G represents a group —$NR_cR_d$ or $(C_1-C_6)$alkoxy group which is optionally substituted, preferentially unsubstituted; according to a particular embodiment, G represents a group —$NR_cR_d$, according to another particular embodiment, G represents a $(C_1-C_6)$alkoxy group;

$R_i$ and $R'_i$, which may be identical or different, represent a hydrogen atom or a $(C_1-C_4)$alkyl group;

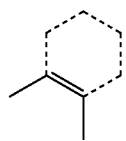

represents an aryl or heteroaryl group fused to the phenyl ring; or alternatively is absent from the phenyl ring; preferentially, when the ring is present, the ring is a benzo;

m represents an integer between 1 and 18 inclusive; particularly an integer between 2 and 16 inclusive; preferentially an integer between 3 and 10; more preferentially an integer between 4 and 6;

$R_c$ and $R_d$, which may be identical or different, represent a hydrogen atom, a $(C_2-C_4)$alkyl group or a substituted $(C_1-C_8)$alkyl group, preferably $(C_2-C_4)$alkyl substituted in particular with one or more groups chosen from i) cyano, ii) $(C_1-C_3)$alkoxy, iii) hydroxyl and iv) $(C_1-C_3)$alkylcarbonyl, preferably with one or more hydroxyl groups; and M' representing an anionic counterion, derived from a salt of an organic or mineral acid, or from an organic or mineral base that ensures the electrical neutrality of the dye;

it being understood that when the dye comprises an alkoxide group, then M' and $Q^+$ may be absent to ensure the electrical neutrality of said dye.

Preferably, the fluorescent dye(s) (b) of the invention are chosen from the styryl dyes of formula (IX) below, and also the organic or mineral acid or base salts thereof, the optical isomers, geometrical isomers and tautomers thereof, and the solvates thereof such as hydrates:

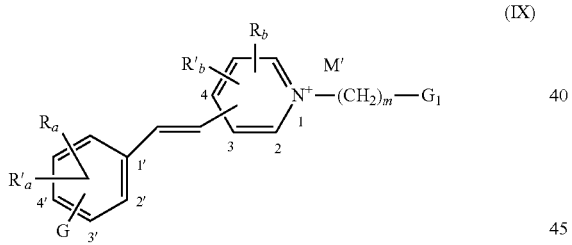

in which formula (IX) G, $G_1$, $R_a$, $R'_a$, $R_b$, $R'_b$ and m are as defined previously.

According to a particular embodiment, the group G is in the para position relative to the —CH═CH— group, i.e. in position 4' of the phenyl group. According to another particular embodiment of the invention, the group G is in the ortho position relative to the —CH═CH— group, i.e. in position 2' of the phenyl group. According to one embodiment, the —CH═CH— group is in the para position of the pyridinium group, i.e. in position 4.

According to another advantageous variant, the —CH═CH— group is in the ortho position of the pyridinium group, i.e. in position 2.

According to a preferred mode of the invention, the fluorescent dye(s) (b) of the invention are chosen from the compounds of formulae (X) and (XI) below, and also the organic or mineral acid or base salts thereof, the optical isomers, geometrical isomers and tautomers thereof, and the solvates thereof such as hydrates:

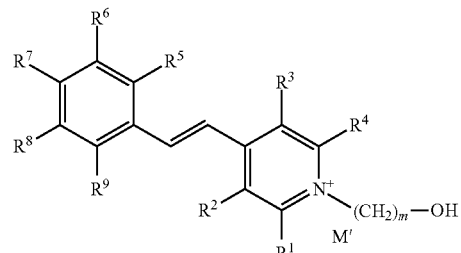

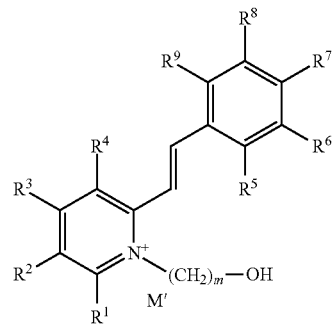

in which formulae (X) and (XI):

$R^1$, $R^2$, $R^3$ and $R^4$, which may be identical or different, represent a hydrogen atom or a $(C_1-C_6)$alkyl group; preferably, $R^2$ and $R^3$ represent a hydrogen atom and $R^1$ and $R^4$, which may be identical or different, represent a hydrogen atom or a $(C_1-C_4)$alkyl group;

$R^5$, $R^6$, $R^7$, $R^8$ and $R^9$, which may be identical or different, represent i) a hydrogen atom or ii) a halogen atom such as Cl, Br or F, iii) a group OR in which R represents a hydrogen atom or $Q^+$ as described previously, or a $(C_1-C_3)$alkyl group, a group from among iv) aryl such as benzene, v) aryl$(C_1-C_3)$alkyl such as benzyl, vi) cyano, vii) nitro, viii) $(C_1-C_3)$alkylthio, ix) amino $NR^{10}R^{11}$ with $R^{10}$ and $R^{11}$, which may be identical or different, representing a) a hydrogen atom, b) a $(C_2-C_4)$alkyl group or c) a substituted $(C_1-C_8)$alkyl group, preferably $(C_2-C_4)$alkyl optionally substituted with one or more groups chosen from:

cyano, $(C_1-C_3)$alkoxy, hydroxyl, and $(C_1-C_3)$alkylcarbonyl;

in particular, $R^{10}$ and $R^{11}$, which may be identical or different, represent a hydrogen atom or a $(C_1-C_6)$ alkyl group substituted with one or more hydroxyl, cyano or $(C_1-C_3)$alkylcarbonyl groups such as hydroxyethyl;

m represents an integer between 1 and 18 inclusive; particularly an integer between 2 and 16 inclusive; preferentially an integer between 3 and 10; more preferentially an integer between 4 and 6;

M' represents an anionic counterion as defined previously;

it being understood that when the dye comprises an alkoxide group, then M' and $Q^+$ may be absent to ensure the electrical neutrality of said dye.

According to a first embodiment of the invention, the fluorescent dye(s) (b) are of formula (X) with:

| R$^1$ | R$^2$ | R$^3$ | R$^4$ | R$^5$ | R$^6$ | R$^7$ | R$^8$ | R$^9$ | m |
|---|---|---|---|---|---|---|---|---|---|
| H | H | H | H | H | H | H | H | H | 1 |
| H | H | H | H | H | t-Bu | OH | t-Bu | H | 5 |
| H | H | H | H | H | t-Bu | OH | t-Bu | H | 5 |
| H | H | H | H | H | H | NH$_2$ | H | H | 1 |
| H | H | H | H | H | H | NH$_2$ | H | OCH$_3$ | 1 |
| H | H | H | H | H | H | OH | Br | H | 5 |
| H | H | H | H | H | OCH$_3$ | OH | OCH$_3$ | H | 5 |
| H | H | H | H | Cl | H | OH | H | Cl | 5 |
| H | H | H | H | H | H | OH | H | H | 10 |
| H | H | H | H | H | OCH$_3$ | OH | OCH$_3$ | H | 10 |
| H | H | H | H | H | t-Bu | OH | t-Bu | H | 10 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | t-Bu | OH | t-Bu | H | 10 |
| H | H | H | H | H | H | N(CH$_2$CH$_3$)CH$_2$CH$_2$OH | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | N(CH$_2$CH$_3$)$_2$ | H | H | 1 |
| H | H | H | H | H | H | n-C$_6$H$_{13}$ | H | H | 1 |
| H | H | H | H | H | H | N(CH$_2$CH$_2$OH)$_2$ | H | H | 2 |
| H | H | H | H | H | H | N(n-Bu)$_2$ | H | H | 2 |
| H | H | H | H | H | OCH$_3$ | OH | H | H | 10 |
| H | H | H | H | H | H | OC$_2$H$_5$OH | H | H | 1 |
| H | H | H | H | H | H | OH | H | H | 1 |
| H | H | benzo | H | H | H | H | H | 1 |
| H | H | benzo | H | H | N(CH$_2$CH$_2$OH)$_2$ | H | H | 1 |
| H | H | benzo | H | H | N(CH$_2$CH$_2$OH)$_2$ | H | H | 1 | and also the organic or mineral acid or base salts thereof, the optical isomers, geometrical isomers and tautomers thereof, and the solvates thereof such as hydrates.

According to a second embodiment, the fluorescent dye(s) (b) are of formula (XI) with:

| R$^1$ | R$^2$ | R$^3$ | R$^4$ | R$^5$ | R$^6$ | R$^7$ | R$^8$ | R$^9$ | m |
|---|---|---|---|---|---|---|---|---|---|
| CH$_3$ | H | H | H | OH | H | OCH$_3$ | H | H | 2 |
| CH$_3$ | H | H | H | H | H | OCH$_3$ | OCH$_2$-Ph | H | 2 |
| CH$_3$ | H | H | H | H | H | H | H | OCH$_3$ | 2 |
| CH$_3$ | H | H | H | F | H | H | H | H | 2 |
| CH$_3$ | H | H | H | H | H | H | OPh | H | 2 |
| CH$_3$ | H | H | H | H | H | N(CH$_2$CH$_2$OAc)$_2$ | H | H | 2 |
| CH$_3$ | H | H | H | OCH$_3$ | H | OCH$_3$ | OCH$_3$ | H | 2 |
| CH$_3$ | H | H | H | H | H | H | CH$_3$ | H | 2 |
| CH$_3$ | H | H | H | H | H | OH | H | H | 2 |
| CH$_3$ | H | H | H | H | OCH$_3$ | OCH$_3$ | OCH$_3$ | H | 2 |
| CH$_3$ | H | H | H | H | OCH$_3$ | OH | OH | H | 2 |
| CH$_3$ | H | H | H | H | H | OCH$_3$ | OCH$_3$ | OCH$_3$ | 2 |
| CH$_3$ | H | H | H | H | H | H | OCH$_3$ | OH | 2 |
| CH$_3$ | H | H | H | H | H | N(n-butyl)$_2$ | H | H | 2 |
| CH$_3$ | H | H | H | H | OCH$_3$ | OCH$_3$ | H | H | 2 |
| CH$_3$ | H | H | H | H | H | H | H | H | 2 |
| CH$_3$ | H | H | H | H | H | i-propyl | H | H | 2 |
| H | H | H | H | H | H | OH | H | H | 6 |
| H | H | H | H | H | OCH$_3$ | OCH$_3$ | OCH$_3$ | H | 6 |
| H | H | H | H | OH | H | OCH$_3$ | H | H | 2 |
| H | H | H | H | OCH$_3$ | H | H | OCH$_3$ | OCH$_3$ | 2 |
| H | H | H | H | H | H | H | H | Br | 2 |
| H | H | H | H | H | H | OH | H | H | 2 |
| H | H | H | H | OCH$_3$ | OCH$_3$ | OCH$_3$ | H | H | 6 |
| H | H | H | H | OH | OCH$_3$ | H | H | H | 6 |
| H | H | H | H | H | OCH$_3$ | OCH$_3$ | H | H | 6 |
| H | H | H | H | H | OCH$_3$ | OCH$_3$ | H | H | 2 |
| H | H | H | H | H | H | C(O)—OH | H | H | 6 |
| H | H | H | H | H | H | C(O)—OH | H | H | 2 |
| H | H | H | H | H | H | i-propyl | H | H | 2 |
| H | H | H | H | H | H | N(CH$_3$)CH$_2$CH$_2$CN | H | H | 2 |
| H | H | H | H | H | H | OCH$_3$ | OCH$_2$Ph | H | 2 |
| H | H | H | H | H | H | H | OPh | H | 2 |
| H | H | H | H | H | H | N(CH$_2$CH$_2$C(O)CH$_3$)$_2$ | H | H | 2 |
| H | H | H | H | OH | H | OCH$_3$ | H | H | 6 |
| H | H | H | H | H | OCH$_3$ | OCH$_3$ | OCH$_3$ | H | 2 |
| H | H | H | H | OCH$_3$ | H | OCH$_3$ | OCH$_3$ | H | 6 |
| H | H | H | H | H | H | H | CH$_3$ | H | 2 |
| H | H | H | H | H | H | N(CH$_3$)CH$_2$CH$_2$OH | H | H | 2 | and also the organic or mineral acid or base salts thereof, the geometrical isomers and tautomers thereof, and the solvates thereof such as hydrates.

Preferably, the fluorescent dye(s) (b) are chosen from those of formulae (X') and (XI') below:

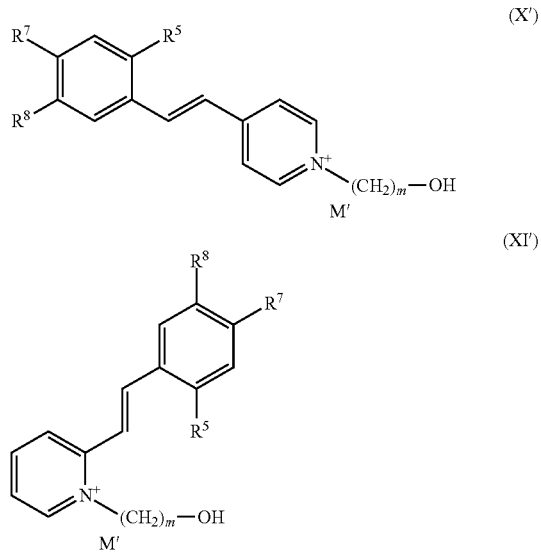

in which formulae (X') and (XI') $R^5$, $R^7$, $R^8$ and m are as defined previously for (X) and (XI), in particular:
- $R^5$ and $R^8$, which may be identical or different, represent a hydrogen atom or a ($C_1$-$C_4$)alkoxy group such as methoxy;
- $R^7$ represents a ($C_1$-$C_4$)alkoxy group or $NR^{10}R^{11}$ with $R^{10}$ representing a) a hydrogen atom, or b) a ($C_1$-$C_6$)alkyl group optionally substituted with one or more groups chosen from i) cyano, ii) ($C_1$-$C_3$)alkoxy, iii) hydroxyl and iv) ($C_1$-$C_3$)alkylcarbonyl and $R^{11}$ representing a) a ($C_2$-$C_5$)alkyl group substituted with one or more groups chosen from i) cyano, ii) ($C_1$-$C_3$)alkoxy, iii) hydroxyl and iv) ($C_1$-$C_3$)alkylcarbonyl;
in particular, $NR^{10}R^{11}$ represents a ($C_2$-$C_4$)alkyl group, a (di)hydroxy($C_2$-$C_4$)alkylamino or hydroxy($C_2$-$C_4$)alkyl(($C_1$-$C_4$)alkyl)amino group;
- m represents an integer between 1 and 18 inclusive; particularly an integer between 2 and 16 inclusive; preferentially an integer between 3 and 10; more preferentially an integer between 4 and 6; and
- M' represents an anionic counterion, derived from a salt of an organic or mineral acid, or from an organic or mineral base that ensures the electrical neutrality of the dye.

According to this embodiment, the fluorescent dye(s) (b) are preferably chosen from those of formula (X') or (XI') with:

| $R^5$ | $R^7$ | $R_8$ | m |
|---|---|---|---|
| $OCH_3$ | $OCH_3$ | $OCH_3$ | 2 |
| $OCH_3$ | $OCH_3$ | $OCH_3$ | 3 |
| $OCH_3$ | $OCH_3$ | $OCH_3$ | 3 |
| $OCH_3$ | $OCH_3$ | $OCH_3$ | 4 |
| $OCH_3$ | $OCH_3$ | $OCH_3$ | 5 |
| $OCH_3$ | $OCH_3$ | $OCH_3$ | 8 |
| $OCH_3$ | $OCH_3$ | $OCH_3$ | 10 |

-continued

| $R^5$ | $R^7$ | $R_8$ | m |
|---|---|---|---|
| $OCH_3$ | $OCH_3$ | $OCH_3$ | 12 |
| $OCH_3$ | $OCH_3$ | $OCH_3$ | 14 |
| $OCH_3$ | $OCH_3$ | $OCH_3$ | 16 |

| $R^5$ | $R^7$ | $R^8$ | m |
|---|---|---|---|
| H | $N(CH_2CH_2OH)_2$ | H | 2 |
| H | $N(CH_2CH_2OH)_2$ | H | 3 |
| H | $N(CH_2CH_2OH)_2$ | H | 4 |
| H | $N(CH_2CH_2OH)_2$ | H | 5 |
| H | $N(CH_2CH_2OH)_2$ | H | 6 |
| H | $N(CH_2CH_2OH)_2$ | H | 8 |
| H | $N(CH_2CH_2OH)_2$ | H | 10 |
| H | $N(CH_2CH_2OH)_2$ | H | 12 |
| H | $N(CH_2CH_2OH)_2$ | H | 14 |
| H | $N(CH_2CH_2OH)_2$ | H | 16 |
| H | $CH_3CH_2N(CH_2CH_2OH)$ | H | 2 |
| H | $CH_3CH_2N(CH_2CH_2OH)$ | H | 4 | and
and also the organic or mineral acid or base salts thereof, the geometrical isomers and tautomers thereof, and the solvates thereof such as hydrates.

According to yet another preferred mode of the invention, the fluorescent dye(s) (b) of the invention are chosen from the compounds of formulae (XII) and (XIII) below, and also the organic or mineral acid or base salts thereof, the optical isomers, geometrical isomers and tautomers thereof, and the solvates thereof such as hydrates:

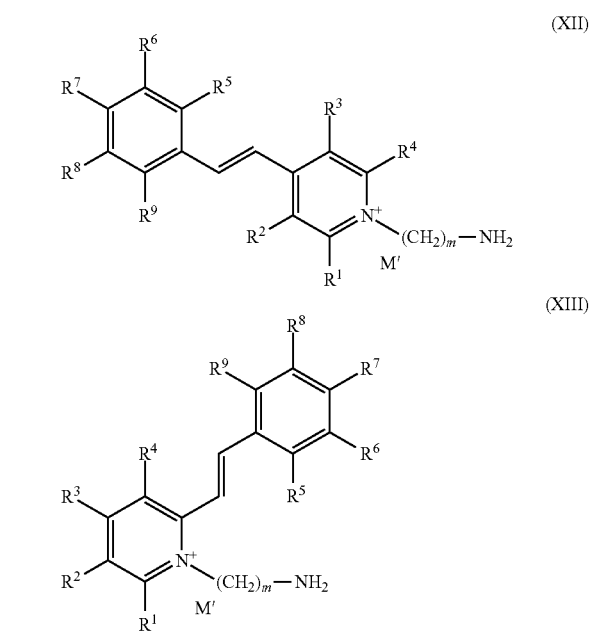

in which formulae (XII) and (XIII):
- $R^1$, $R^2$, $R^3$ and $R^4$, which may be identical or different, represent a hydrogen atom or a ($C_1$-$C_6$)alkyl group; preferably, $R^2$ and $R^3$ represent a hydrogen atom and $R^1$ and $R^4$, which may be identical or different, represent a hydrogen atom or a ($C_1$-$C_4$)alkyl group;
- $R^5$, $R^6$, $R^7$, $R^8$ and $R^9$, which may be identical or different, represent i) a hydrogen atom or ii) a halogen atom such as Cl, Br or F, iii) a group OR in which R represents a hydrogen atom or Q⁺ as described previously, or a ($C_1$-$C_3$)alkyl group, a group from among iv) aryl such as benzene, v) aryl($C_1$-$C_3$)alkyl such as benzyl, vi) cyano, vii) nitro, viii) ($C_1$-$C_3$)alkylthio, ix) amino $NR^{10}R^{11}$ with $R^{10}$ and $R^{11}$, which may be identical or different, representing a) a hydrogen atom or b) a ($C_1$-$C_8$)alkyl group optionally substituted with one or more groups chosen from:

cyano, ($C_1$-$C_3$)alkoxy, hydroxyl, and ($C_1$-$C_3$)alkylcarbonyl;

in particular, $R^{10}$ and $R^{11}$, which may be identical or different, represent a hydrogen atom or a ($C_1$-$C_6$) alkyl group optionally substituted with one or more hydroxyl, cyano or ($C_1$-$C_3$)alkylcarbonyl groups such as methyl, ethyl, butyl, isobutyl, cyanoethyl, methylcarbonylethyl, or hydroxyethyl;

m represents an integer between 1 and 18 inclusive; particularly an integer between 2 and 16 inclusive; preferentially an integer between 3 and 10; more preferentially an integer between 4 and 6;

M' represents an anionic counterion derived from salts of organic or mineral acids preferably originating from Y;

it being understood that when the dye comprises an alkoxide group, then M' and Q⁺ may be absent to ensure the electrical neutrality of said dye.

According to one embodiment of the invention, the fluorescent dye(s) (b) are of formula (XII) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| H | H | H | H | H | H | $OCH_3$ | $OCH_3$ | $OCH_3$ | 2 |
| H | H | H | H | OH | $OCH_3$ | H | H | H | 2 |
| H | H | H | H | H | H | H | H | H | 2 |
| H | H | H | H | H | $OCH_3$ | $OCH_3$ | H | H | 2 |
| H | H | H | H | OH | H | OH | H | H | 6 |
| H | H | H | H | $OCH_3$ | H | $OCH_3$ | $OCH_3$ | H | 6 |
| H | H | H | H | H | H | OH | H | H | 6 |
| H | H | H | H | $OCH_3$ | H | H | H | F | 2 |
| H | H | H | H | H | H | C(O)—OH | H | H | 2 |
| H | H | H | H | H | H | Isopropyl | H | H | 2 |
| H | H | H | H | H | H | $N(CH_2CH_2C(O)CH_3)_2$ | H | H | 2 |
| H | H | H | H | OH | H | $OCH_3$ | H | H | 2 |
| H | H | H | H | H | H | OH | H | H | 2 |
| H | H | H | H | H | $OCH_3$ | OH | OH | H | 2 |
| H | H | H | H | H | $CH_3$ | $OCH_2Ph$ | $CH_3$ | H | 2 |
| H | H | H | H | H | $OCH_3$ | $OCH_3$ | $OCH_3$ | H | 2 |
| H | H | H | H | H | $OCH_3$ | $OCH_3$ | $OCH_3$ | H | 6 |
| H | H | H | H | H | H | $N(CH_3)_2$ | H | H | 6 |
| H | H | H | H | H | H | $OCH_3$ | $OCH_3$ | $OCH_3$ | 6 |
| H | H | H | H | H | H | Phenyl | H | H | 6 |
| H | H | H | H | H | $OCH_3$ | $OCH_3$ | H | H | 6 |
| H | H | H | H | H | H | C(O)—OH | H | H | 6 |
| H | H | H | H | H | H | $N(n\text{-Butyl})_2$ | H | H | 2 |
| H | H | H | H | H | H | $OCH_3$ | $OCH_3$ | H | 3 |
| H | H | H | H | H | H | $OCH_3$ | $OCH_3$ | H | 2 |
| H | H | H | H | H | H | $OCH_3$ | $OCH_3$ | H | 5 |
| H | H | H | H | H | H | $OCH_3$ | H | H | 3 |
| H | H | H | H | H | H | $N(CH_3)_2$ | H | H | 3 |
| H | H | H | H | H | H | H | H | H | 3 | and also the organic or mineral acid or base salts thereof, the optical isomers, geometrical isomers and tautomers thereof, and the solvates thereof such as hydrates.

According to another embodiment, the fluorescent dye(s) (b) are of formula (XIII) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| $CH_3$ | H | H | H | OH | H | $OCH_3$ | H | H | 2 |
| $CH_3$ | H | H | H | H | H | $OCH_3$ | $OCH_2$-Ph | H | 2 |
| $CH_3$ | H | H | H | H | H | H | H | $OCH_3$ | 2 |
| $CH_3$ | H | H | H | F | H | H | H | H | 2 |
| $CH_3$ | H | H | H | H | H | H | OPh | H | 2 |
| $CH_3$ | H | H | H | H | H | $N(CH_2CH_2OAc)_2$ | H | H | 2 |
| $CH_3$ | H | H | H | $OCH_3$ | H | $OCH_3$ | $OCH_3$ | H | 2 |
| $CH_3$ | H | H | H | H | H | H | $CH_3$ | H | 2 |
| $CH_3$ | H | H | H | H | OH | H | H | H | 2 |
| $CH_3$ | H | H | H | H | $OCH_3$ | $OCH_3$ | $OCH_3$ | H | 2 |
| $CH_3$ | H | H | H | H | $OCH_3$ | OH | OH | H | 2 |
| $CH_3$ | H | H | H | H | H | $OCH_3$ | $OCH_3$ | $OCH_3$ | 2 |
| $CH_3$ | H | H | H | H | H | H | $OCH_3$ | OH | 2 |
| $CH_3$ | H | H | H | H | H | $N(n\text{-butyl})_2$ | H | H | 2 |
| $CH_3$ | H | H | H | H | $OCH_3$ | $OCH_3$ | H | H | 2 |
| $CH_3$ | H | H | H | H | H | H | H | H | 2 |
| $CH_3$ | H | H | H | H | H | i-propyl | H | H | 2 |
| H | H | H | H | H | H | OH | H | H | 6 |
| H | H | H | H | H | $OCH_3$ | $OCH_3$ | $OCH_3$ | H | 6 |
| H | H | H | H | OH | H | $OCH_3$ | H | H | 2 |
| H | H | H | H | $OCH_3$ | H | H | $OCH_3$ | $OCH_3$ | 2 |
| H | H | H | H | H | H | H | H | Br | 2 |
| H | H | H | H | H | H | OH | H | H | 6 |
| H | H | H | H | H | H | $N(CH_3)_2$ | H | H | 6 |
| H | H | H | H | $OCH_3$ | $OCH_3$ | $OCH_3$ | H | H | 6 |
| H | H | H | H | OH | $OCH_3$ | H | H | H | 6 |
| H | H | H | H | H | $OCH_3$ | $OCH_3$ | H | H | 6 |
| H | H | H | H | H | $OCH_3$ | $OCH_3$ | H | H | 2 |
| H | H | H | H | H | H | C(O)—OH | H | H | 6 |
| H | H | H | H | H | H | C(O)—OH | H | H | 2 |
| H | H | H | H | H | H | i-propyl | H | H | 2 |
| H | H | H | H | H | H | $N(CH_3)CH_2CH_2CN$ | H | H | 2 |
| H | H | H | H | H | H | $OCH_3$ | $OCH_2Ph$ | H | 2 |
| H | H | H | H | H | H | H | OPh | H | 2 |
| H | H | H | H | H | H | $N(CH_2CH_2C(O)CH_3)_2$ | H | H | 2 |
| H | H | H | H | OH | H | $OCH_3$ | H | H | 6 |

-continued

| R¹ | R² | R³ | R⁴ | R⁵ | R⁶ | R⁷ | R⁸ | R⁹ | m |
|---|---|---|---|---|---|---|---|---|---|
| H | H | H | H | H | OCH₃ | OCH₃ | OCH₃ | H | 2 |
| H | H | H | H | OCH₃ | H | OCH₃ | OCH₃ | H | 6 |
| H | H | H | H | H | H | H | CH₃ | H | 2 |
| H | H | H | H | H | H | N(CH₃)CH₂CH₂OH | H | H | 2 |
| CH₃ | H | H | H | H | H | N(CH₃)₂ | H | H | 2 | and also the organic or mineral acid or base salts thereof, the geometrical isomers and tautomers thereof, and the solvates thereof such as hydrates.

More particularly, the fluorescent dye(s) (b) of the invention are chosen from those of formulae (XII') and (XIII') below:

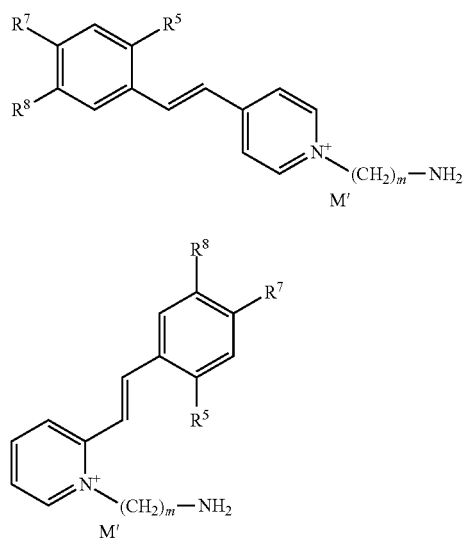

(XII')

(XIII')

in which formulae (XII') and (XIII') $R^5$, $R^7$, $R^8$ and m are as defined previously for (X) and (XI), in particular:

$R^5$ and $R^8$, which may be identical or different, represent a hydrogen atom or a $(C_1-C_4)$alkoxy group such as methoxy;

$R^7$ represents a $(C_1-C_4)$alkoxy group or $NR^{10}R^{11}$ with $R^{10}$ and $R^{11}$, which may be identical or different, representing a) a hydrogen atom, or b) a $(C_1-C_8)$alkyl group optionally substituted with one or more groups chosen from i) cyano, ii) $(C_1-C_3)$alkoxy, iii) hydroxyl, and iv) $(C_1-C_3)$alkylcarbonyl; in particular, $R^{10}$ and $R^{11}$, which may be identical or different, represent a hydrogen atom or a $(C_1-C_6)$alkyl group optionally substituted with one or more groups from the following: hydroxyl, cyano or $(C_1-C_3)$alkylcarbonyl such as methyl, ethyl, butyl, isobutyl, cyanoethyl, methylcarbonylethyl or hydroxyethyl; preferably, $R^{10}$ and $R^{11}$, which may be identical or different, represent a $(C_1-C_6)$alkyl group optionally substituted with one or more hydroxyl groups such as hydroxyethyl;

m represents an integer between 1 and 18 inclusive; particularly an integer between 2 and 16 inclusive; preferentially an integer between 3 and 10; more preferentially an integer between 4 and 6; and M' represents an anionic counterion, derived from a salt of an organic or mineral acid, or from an organic or mineral base that ensures the electrical neutrality of the dye.

According to one embodiment, the fluorescent dye(s) (b) of the invention are of formula (XII') or (XIII') with:

| R⁵ | R⁷ | R₈ | m |
|---|---|---|---|
| H | N(CH₂CH₂OH)₂ | H | 2 |
| H | N(CH₂CH₂OH)₂ | H | 3 |
| H | N(CH₂CH₂OH)₂ | H | 4 |
| H | N(CH₂CH₂OH)₂ | H | 5 |
| H | N(CH₂CH₂OH)₂ | H | 6 |
| H | N(CH₂CH₂OH)₂ | H | 8 |
| H | N(CH₂CH₂OH)₂ | H | 10 |
| H | N(CH₂CH₂OH)₂ | H | 12 |
| H | N(CH₂CH₂OH)₂ | H | 14 |
| H | N(CH₂CH₂OH)₂ | H | 16 | and

| R⁵ | R⁷ | R⁸ | m |
|---|---|---|---|
| OCH₃ | OCH₃ | OCH₃ | 2 |
| OCH₃ | OCH₃ | OCH₃ | 3 |
| OCH₃ | OCH₃ | OCH₃ | 3 |
| OCH₃ | OCH₃ | OCH₃ | 4 |
| OCH₃ | OCH₃ | OCH₃ | 5 |
| OCH₃ | OCH₃ | OCH₃ | 8 |
| OCH₃ | OCH₃ | OCH₃ | 10 |
| OCH₃ | OCH₃ | OCH₃ | 12 |
| OCH₃ | OCH₃ | OCH₃ | 14 |
| OCH₃ | OCH₃ | OCH₃ | 16 | and also the organic or mineral acid or base salts thereof, the geometrical isomers and tautomers thereof, and the solvates thereof such as hydrates.

More particularly, the fluorescent dye(s) (b) of the invention are chosen from those of formula (V), (VIII) or (IX) as defined previously in which G represents a hydrogen atom.

More particularly, the fluorescent dye(s) (b) of the invention are chosen from those of formulae (XIV) and (XV) below:

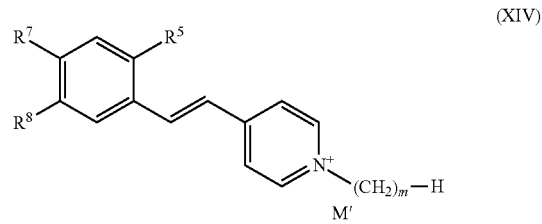

(XIV)

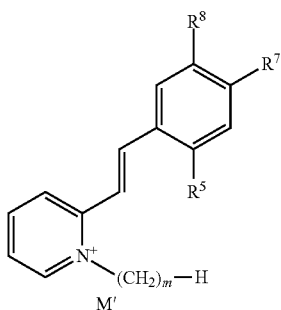

(XV)

in which formulae (XIV) and (XV) $R^5$, $R^7$, $R^8$ and m are as defined previously for (X) and (XI), in particular:

- $R^5$ and $R^8$, which may be identical or different, represent a hydrogen atom or a ($C_1$-$C_4$)alkoxy group such as methoxy, preferably, $R^5$ and $R^8$ represent a hydrogen atom;
- $R^7$ represents a ($C_1$-$C_4$)alkoxy group or $NR^{10}R^{11}$ with $R^{10}$ and $R^{11}$, which may be identical or different, representing a) a hydrogen atom, or b) a ($C_1$-$C_8$)alkyl group optionally substituted with one or more groups chosen from i) hydroxyl, ii) R—Z—C(X)—Y— with X, Y and Z representing an oxygen or sulfur atom or N(R'), or alternatively X and/or Z represent a bond, R and R', which may be identical or different, represent a hydrogen atom or a ($C_1$-$C_6$)alkyl group, preferably, X represents an oxygen atom, iii) sulfonic $SO_3H$, iv) sulfonate $SO_3^-$, $Q^+$, v) carboxylate $C(O)O^-$, $Q^+$ with $Q^+$ representing a cationic counterion such as an alkali metal or alkaline-earth metal; in particular, $R^7$ represents a group $NR^{10}R^{11}$ with $R^{10}$ and $R^{11}$, which may be identical or different, representing a) a hydrogen atom, or b) a ($C_1$-$C_6$)alkyl group optionally substituted with one or more groups chosen from i) hydroxyl, ii) carboxyl, iii) carboxylate, iv) sulfonic, and v) sulfonate, more particularly chosen from identical or different groups representing a) a hydrogen atom, or b) a ($C_1$-$C_6$)alkyl group optionally substituted with one or more groups chosen from i) hydroxyl, ii) carboxyl, and iii) carboxylate;
- m represents an integer between 1 and 18 inclusive; particularly an integer between 1 and 6 inclusive; preferentially an integer between 1 and 4; more preferentially an integer between 1 and 2; and
- M' represents an anionic counterion, derived from a salt of an organic or mineral acid, or from an organic or mineral base that ensures the electrical neutrality of the dye;

it being understood that when the dye comprises a sulfonate or carboxylate group, then M' and $Q^+$ may be absent to ensure the electrical neutrality of said dye.

More preferentially, the fluorescent dye(s) (b) of the invention are chosen from the following compounds, and also the geometrical isomers thereof, the tautomers thereof, the solvates thereof and mixtures thereof:

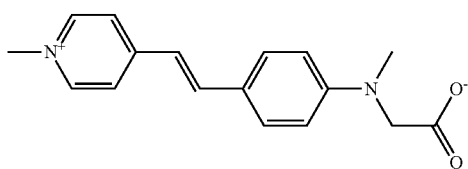
(d)

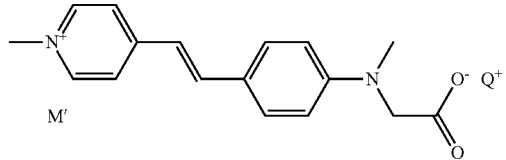
(d')

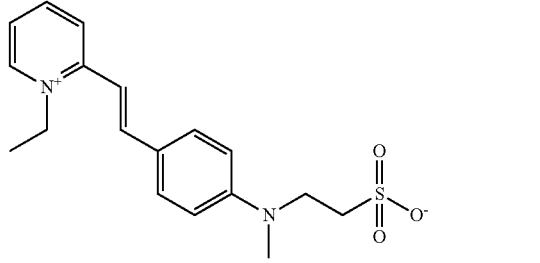
(e)

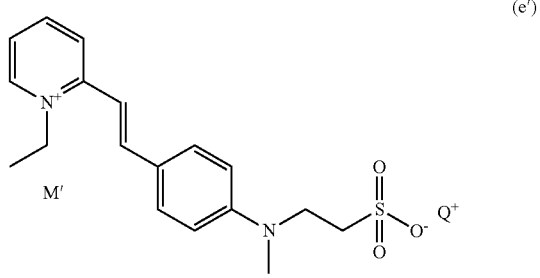
(e')

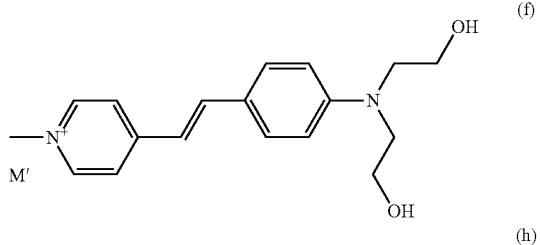
(f)

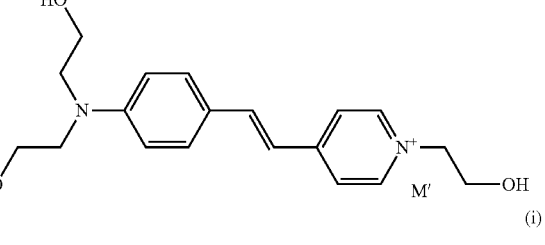
(h)

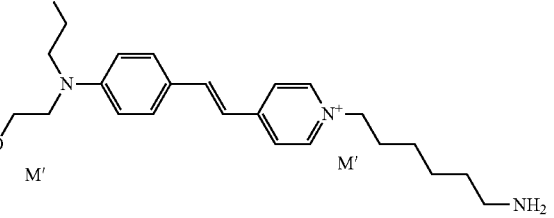
(i)

with M' and $Q^+$ as defined previously.

The Oxidizing Agents

The process for dyeing keratin fibres and the cosmetic composition according to the present invention may also optionally use, or comprise, one or more oxidizing agents.

Preferably, the oxidizing agent(s) are chosen from chemical oxidizing agents.

The term "chemical oxidizing agent" means an oxidizing agent other than atmospheric oxygen.

More particularly, the chemical oxidizing agent(s) are chosen from hydrogen peroxide, hydrogen peroxide-generating systems, urea peroxide, alkali metal bromates or ferricyanides, peroxygenated salts, for instance persulfates, perborates, peracids and precursors thereof and percarbonates of alkali metals or alkaline-earth metals, and mixtures thereof.

Preferably, the chemical oxidizing agent(s) are chosen from hydrogen peroxide and hydrogen peroxide-generating systems.

According to a preferred embodiment, the hydrogen peroxide-generating system(s) are chosen from urea peroxide, polymeric complexes that can release hydrogen peroxide, chosen from polyvinylpyrrolidone/$H_2O_2$; oxidases; perborates; and percarbonates.

Preferably, the chemical oxidizing agent is hydrogen peroxide, and more preferentially aqueous hydrogen peroxide solution.

The chemical oxidizing agent(s) are advantageously applied in the form of an aqueous solution of which the content of chemical oxidizing agents is preferably between 0.05% and 5% by weight and more preferentially between 0.1% and 2% by weight, relative to the total weight of the aqueous solution.

According to a preferred embodiment of the invention, the dyeing process does not use any oxidizing agent.

According to this preferred embodiment of the invention, the cosmetic composition comprising ingredients (a) and (b) does not comprise any oxidizing agent.

The Reducing Agents

The process for dyeing keratin fibres and the cosmetic composition according to the present invention may also optionally use, or comprise, one or more reducing agents.

The reducing agent(s) that are useful in the present invention are advantageously chosen from the compounds of formula (XVI) below, and also the addition salts thereof and mixtures thereof:

$$H(X)_q(R_{10})_t \qquad (XVI)$$

in which formula (XVI):
X represents P, S or $SO_2$,
q represents an integer equal to 0 or 1,
t represents an integer equal to 1 or 2, and
R represents a linear or branched, saturated or unsaturated $C_1$ to $C_{20}$ alkyl radical, optionally interrupted with a heteroatom, and/or optionally substituted with one or more radicals chosen from hydroxyl, halo, amine, carboxyl, (($C_1$-$C_{30}$)alkoxy)carbonyl, amido, (($C_1$-$C_{30}$)alkyl)aminocarbonyl, ($C_1$-$C_{30}$)acyl)amino, mono or dialkylamino, and mono or dihydroxylamino radicals.

Preferably, the reducing agent(s) are chosen from thioglycolic acid, thiolactic acid, glyceryl monothioglycolate, cysteamine, N-acetylcysteamine, N-propionylcysteamine, cysteine, N-acetylcysteine, thiomalic acid, pantetheine, 2,3-dimercaptosuccinic acid, N-(mercaptoalkyl)-o-hydroxyalkylamides, N-mono- or N,N-dialkylmercapto-4-butyramides, aminomercaptoalkylamides, N-(mercaptoalkyl) succinamic acid and N-(mercaptoalkyl)succinimide derivatives, alkylamino mercaptoalkylamides, the azeotropic mixture of 2-hydroxypropyl thioglyconate and of (2-hydroxy-1-methyl)ethyl thioglycolate, mercaptoalkylaminoamides, N-mercaptoalkylalkanediamides and formamidinesulfinic acid derivatives, salts thereof, and mixtures thereof.

Preferably, the reducing agent(s) are also chosen from salts such as sodium sulfite, sodium dithionite or sodium thiosulfate, and mixtures thereof.

The chemical reducing agent(s) are advantageously applied in the form of an aqueous solution of which the content of chemical reducing agents is preferably between 0.01% and 10% by weight and more preferentially between 0.1% and 5% by weight, relative to the total weight of the aqueous solution.

According to a preferred embodiment of the invention, the dyeing process does not use any reducing agent.

According to this preferred embodiment of the invention, the cosmetic composition comprising ingredients (a) and (b) does not comprise any reducing agent.

The Cosmetic Medium and the Solvents

The triarylmethane dye(s) (a) chosen from the compounds of formula (I), as defined previously, and (b) the fluorescent dye(s), as defined previously, and also, when they are present, the oxidizing agent(s) and/or the reducing agent(s), may be dissolved beforehand before being applied to the keratin fibres.

In other words, the ingredients used in the dyeing process of the present invention may be present in one or more compositions.

The composition(s) comprising the ingredients according to the present invention are cosmetic compositions, i.e. they are preferably aqueous. Besides water, they may comprise one or more organic solvents, or mixtures thereof.

Examples of organic solvents that may be mentioned include linear or branched $C_2$ to $C_4$ alkanols, such as ethanol and isopropanol; glycerol; polyols and polyol ethers, for instance 2-butoxyethanol, propylene glycol, hexylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The pH

The pH of the composition(s) used in the dyeing process of the invention and of the composition of the invention comprising ingredients (a) and (b) is preferably between 2 and 12 and more preferentially between 3 and 11. It may be adjusted to the desired value by means of acidifying or alkaline agents usually used in the dyeing of keratin fibres, or alternatively using standard buffer systems.

The pH of the composition which comprises ingredients (a) and (b) and that of the composition(s) used in the dyeing process of the invention is preferably between 6 and 11 inclusive, more preferentially between 7 and 10 and better still between 7.5 and 9.5, such as between 9 and 9.5.

Among the acidifying agents, mineral and organic acids as defined previously, mention may be made, by way of example, of mineral or organic acids, for instance hydrochloric acid, orthophosphoric acid or sulfuric acid, carboxylic acids, for instance acetic acid, tartaric acid, citric acid and lactic acid, and sulfonic acids.

The alkaline agent(s) may be chosen especially from mineral, organic or hybrid alkaline agents, and mixtures thereof.

The mineral alkaline agent(s) are preferably chosen from ammonia, alkaline carbonates or bicarbonates such as ammonium, sodium or potassium carbonate or bicarbonate, ammonium, sodium or potassium hydroxide, or mixtures thereof.

The organic alkaline agent(s) are preferably chosen from organic amines with a $pK_b$ at 25° C. of less than 12, preferably of less than 10 and more advantageously still of less than 6. It should be noted that it concerns the $pK_b$ corresponding to the function having the highest basicity. In addition, the organic amines do not comprise any alkyl or alkenyl fatty chain comprising more than ten carbon atoms.

The organic alkaline agent(s) are preferably chosen from alkanolamines, in particular mono-, di- or tri-hydroxy($C_1$-$C_6$)alkylamines, such as triethanolamine, oxyethylenated and/or oxypropylenated ethylenediamines, amino acids, polyamines of formula (XVII) below, and mixtures thereof:

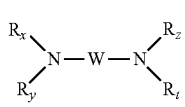

(XVII)

in which formula (XVII) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (XVII) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (XVIII) below, and also salts thereof:

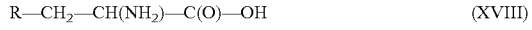

(XVIII)

in which formula (XVIII) R represents a group chosen from imidazolyl, preferably imidazolyl-4-yl; aminopropyl; aminoethyl; —$(CH_2)_2N(H)$—$C(O)$—$NH_2$; and —$(CH_2)_2$—N(H)—$C(NH)$—$NH_2$.

The compounds corresponding to formula (XVIII) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and balenine.

The organic amine may also be chosen from compounds comprising a guanidine function. As amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, n-amidinoalanine, 3-guanidinopropionic acid, 4-guanidinobutyric acid and 2-([amino (imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the alkaline agent(s) that are useful in the invention are chosen from aqueous ammonia, alkanolamines, amino acids in neutral or ionic form, in particular basic amino acids, and preferably corresponding to those of formula (XVIII).

More preferentially, the alkaline agent(s) are chosen from aqueous ammonia, ammonium bicarbonate, ammonium hydroxide, mono-, di- or tri-hydroxy($C_1$-$C_6$)alkylamines, such as triethanolamine, and mixtures thereof.

Forms of the Composition

The composition(s) comprising the triarylmethane dye(s) (a) chosen from the compounds of formula (I), as defined previously, and the fluorescent dye(s) (b) as defined previously, may be in various presentation forms, such as in the form of liquids, lotions, creams or gels or in any other form that is suitable for dyeing keratin fibres.

It may also be packaged under pressure in an aerosol container in the presence of a propellant or in a non-aerosol container and may form a foam.

Additives

When the ingredients used in the dyeing process according to the present invention are present in one or more composition(s), said compositions may also optionally comprise one or more additives, different from the ingredients of the invention and among which mention may be made of fatty substances, cationic, anionic, nonionic, amphoteric or zwitterionic surfactants, cationic, anionic, nonionic or amphoteric polymers or mixtures thereof, antidandruff agents, anti-seborrhoea agents, agents for preventing hair loss and/or for promoting hair regrowth, vitamins and provitamins including panthenol, sunscreens, mineral or organic pigments, sequestrants, plasticizers, solubilizers, acidifying agents, mineral or organic thickeners, especially polymeric thickeners, opacifiers or nacreous agents, antioxidants, hydroxy acids, fragrances, preserving agents, pigments and ceramides.

Needless to say, a person skilled in the art will take care to select this or these optional additional compound(s) such that the advantageous properties intrinsically associated with the composition(s) in accordance with the invention are not, or are not substantially, adversely affected by the envisaged addition(s).

The above additives may generally be present in an amount, for each of them, of between 0 and 20% by weight relative to the total weight of the composition comprising them.

The Dyeing Process

The process for dyeing keratin fibres according to the present invention comprises the application to said keratin fibres of the following ingredients:

(a) one or more triarylmethane dyes chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof, and (b) one or more fluorescent dyes, as defined previously, it being understood that the triarylmethane dye(s) (a) (ingredients (a)) and the fluorescent dye(s) (ingredients (b)) are applied to said keratin fibres together or sequentially.

In other words, the dyeing process according to the present invention may be performed in one or more steps.

According to a particularly preferred embodiment, the triarylmethane dye(s) (a) and the fluorescent dye(s) (b), as defined previously, are applied together (or jointly), i.e. simultaneously, to the keratin fibres. According to this embodiment, the dyeing process is performed in one step.

According to this one-step embodiment, the process comprises a step of applying to said keratin fibres a cosmetic composition according to the invention which comprises one or more triarylmethane dyes (a) chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof, and one or more fluorescent dyes (b) as defined previously.

According to another particularly preferred embodiment, the triarylmethane dye(s) (a), as defined previously, and the fluorescent dye(s) (b), as defined previously, are applied sequentially, i.e. successively. According to this other embodiment, the dyeing process is performed in at least two steps.

According to a first embodiment in at least two steps, the fluorescent dye(s) (b), as defined previously, are applied to the keratin fibres subsequently to the triarylmethane dye(s) (a), as defined previously. In other words, the fluorescent dye(s) (b), as defined previously, are applied after the triarylmethane dye(s) (a), as defined previously.

According to this first embodiment, the process for dyeing keratin fibres comprises at least the following two successive steps:

a first step of applying to said keratin fibres a cosmetic composition comprising one or more triarylmethane dyes (a) chosen from the compounds of formula (I), as defined previously, and also the optical isomers thereof, the geometrical isomers thereof, the tautomers thereof, the organic or mineral, acid or base salts thereof, the solvates thereof such as hydrates, and mixtures thereof, followed by a second step of applying to said keratin fibres a cosmetic composition which comprises one or more fluorescent dyes (b), as defined previously.

According to a preferred embodiment in at least two steps, the triarylmethane dye(s) (a), as defined previously, are applied to the keratin fibres subsequently to the fluorescent dye(s) (b), as defined previously. In other words, the triarylmethane dye(s) (a), as defined previously, are applied after the fluorescent dye(s) (b), as defined previously.

According to this preferred embodiment, the process for dyeing keratin fibres comprises at least the following two successive steps:

a first step of applying to said keratin fibres a cosmetic composition comprising one or more fluorescent dyes (b), as defined previously, followed by a second step of applying to said keratin fibres a cosmetic composition comprising one or more triarylmethane dyes (a) chosen from the compounds of formula (I), as defined previously, and also the optical isomers thereof, the geometrical isomers thereof, the tautomers thereof, the organic or mineral, acid or base salts thereof, the solvates thereof such as hydrates, and mixtures thereof.

Preferably, ingredients (a) and (b) are applied to the keratin fibres in a bath ratio that may range from 0.1 to 10 and more particularly from 0.2 to 8. For the purposes of the present invention, the term "bath ratio" means the ratio between the total weight of ingredient (a) or (b) and the total weight of keratin fibres to be treated.

When the dyeing process is performed in one step, ingredients (a) and (b) are advantageously left to stand on the keratin fibres for a time ranging from 1 to 90 minutes and more preferentially for a time ranging from 5 to 60 minutes.

When the dyeing process is performed in at least two steps, each of the ingredients (a) and (b) may be advantageously left to stand on the keratin fibres for a time ranging from 1 to 60 minutes and more preferentially for a time ranging from 5 to 45 minutes.

On conclusion of the dyeing process according to the invention, in one or at least two steps, the keratin fibres are advantageously rinsed with water. They may optionally be washed with a shampoo, followed by rinsing with water, before being dried or left to dry.

When the dyeing process is performed in at least two steps, the keratin fibres are advantageously rinsed with water between each step. In other words, the dyeing process may comprise an intermediate rinsing step between the application of the first ingredient and the application of the second ingredient. During this intermediate rinsing step, the keratin fibres may optionally be washed with a shampoo, followed by rinsing with water, before being dried or left to dry.

The dyeing process according to the present invention may be performed at room temperature (25° C.) or with heating.

When they are present, the reducing agent(s) may be applied separately or together with one of the ingredients (a) or (b). Preferably, when they are present, the reducing agent(s) are applied together with the ingredient (b).

When they are present, the oxidizing agent(s) may be applied separately or together with one of the ingredients (a) or (b). Preferably, when they are present, the oxidizing agent(s) are applied after application of ingredients (a) and (b).

According to a particular embodiment, the process for dyeing keratin fibres according to the present invention comprises the following successive steps:

a first step of applying to said keratin fibres a cosmetic composition comprising one or more triarylmethane dyes (a) chosen from the compounds of formula (I), as defined previously, and also the optical isomers thereof, the geometrical isomers thereof, the tautomers thereof, the organic or mineral, acid or base salts thereof, the solvates thereof such as hydrates, and mixtures thereof, followed by a second step of applying to said keratin fibres a cosmetic composition comprising one or more fluorescent dyes (b), as defined previously, and one or more reducing agents, as defined previously.

According to a particular embodiment of the dyeing process of the invention, no step of said process involves an oxidizing agent.

According to another advantageous embodiment of the dyeing process of the invention, no step of said process involves a reducing agent.

The dyeing process according to the present invention may be applied to wet or dry, preferably dry, keratin fibres.

The Multi-Compartment Device

The present invention also relates to a multi-compartment device comprising a first compartment containing one or more triarylmethane dyes (a) chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof, and a second compartment containing one or more fluorescent dyes (b) as defined previously.

Use

A subject of the present invention is also the use of one or more fluorescent dye(s) (b), as defined previously, combined with one or more triarylmethane dye(s) (a) chosen from the compounds of formula (I), as defined previously, and also the optical isomers thereof, the geometrical isomers thereof, the tautomers thereof, the organic or mineral acid or base salts thereof, the solvates thereof such as hydrates, and mixtures thereof, for the dyeing of light keratin fibres, especially human keratin fibres such as the hair, in chestnut-brown, dark chestnut-brown, brown, brown with a glint or even black, without using an additional dye other than (a) or (b).

According to a particular embodiment, the "keratin fibres" are human keratin fibres and more particularly the hair.

The examples that follow serve to illustrate the invention without, however, being limiting in nature.

EXAMPLES

In the examples that follow, all the amounts are given as weight percentages relative to the total weight of the composition, unless otherwise indicated.

1. First Example of Combined Application a) Preparation of the Compositions

Composition (A1) comprising a triarylmethane dye of formula (I) according to the invention, was prepared from the ingredients whose contents are mentioned in the table below.

|  | Composition A1 |
| --- | --- |
| [triarylmethane dye structure] | 0.2 |
| Monoethanolamine | pH = 4 |
| Water | qs 100 |

Compositions (B1) and (B2), comprising a fluorescent dye, were prepared from the ingredients whose contents are mentioned in the table below.

|  | Composition B1 | Composition B2 |
| --- | --- | --- |
| [fluorescent dye structure 1] | 0.2 | — |
| [fluorescent dye structure 2] | — | 0.2 |
| Monoethanolamine | pH = 4 | pH = 4 |
| Water | qs 100 | qs 100 | b) Procedure

Compositions (A1), (B1) and (B2) obtained above were mixed so as to obtain the following mixtures:
A1+B1 in a 1/1 ratio, and
A1+B2 in a 1/1 ratio.
10 ml of compositions (A1), (B1), (B2), (A1+B1) and (A1+B2) were applied to 1 g locks of hair.

After a leave-on time of 20 minutes at room temperature, the locks of hair were rinsed with water and wrung dry.

The locks were then subjected to 10 shampoo washes, made up of two cycles of five shampoo washes. After each shampoo wash cycle, the locks were dried and the colour of the locks was measured using a Minolta CM2600d spectrocolorimeter (specular components included, 10° angle, illuminant D65) in the CIEL*a*b* system.

In this system, L* represents the intensity of the colour, a* indicates the green/red colour axis and b* the blue/yellow colour axis.

The lower the value of L*, the darker or more intense the colour. The higher the value of a*, the redder the shade, and the higher the value of b*, the yellower the shade.

c) Results

The results of the colouring on the locks of hair containing 90% white hairs are given in the table below.

|  | Colour | L* | a* | b* |
|---|---|---|---|---|
| A1 | Intense blue | 40.50 | −15.66 | −15.51 |
| B1 | Red | 40.68 | 51.77 | 45.37 |
| B2 | Red | 42.29 | 48.07 | 44.34 |
| A1 + B1 | Brown | 20.29 | 5.88 | 5.05 |
| A1 + B2 | Black | 19.02 | −0.28 | −5.53 |

The results obtained above show that the simultaneous application of a triarylmethane dye of formula (I) according to the present invention and of a fluorescent dye makes it possible to obtain very intense and chromatic colours.

These results also show that the process according to the invention, using only two particular direct dyes, a triarylmethane dye of formula (I) combined with a fluorescent dye, makes it possible to obtain brown colours, which are persistent even after 10 shampoo washes.

II. Second Example of Combined Application a) Preparation of the Compositions

Composition (A2) comprising a triarylmethane dye of formula (I) according to the invention, was prepared from the ingredients whose contents are mentioned in the table below.

| | Composition A2 |
|---|---|
| [triarylmethane dye structure] | 0.2 |
| Monoethanolamine | pH = 9.5 |
| Water | qs 100 |

Compositions (B3) and (B4), comprising a fluorescent dye, were prepared from the ingredients whose contents are mentioned in the table below.

| | Composition B3 | Composition B4 |
|---|---|---|
| [fluorescent dye structure 1] | 0.2 | — |
| [fluorescent dye structure 2] | — | 0.2 |
| Monoethanolamine | pH = 9.5 | pH = 9.5 |
| Water | qs 100 | qs 100 | b) Procedure

Compositions (A2), (B3) and (B4) obtained above were mixed so as to obtain the following mixtures:

A2+B3 in a 1/1 ratio, and

A2+B4 in a 1/1 ratio.

10 ml of compositions (A2), (B3), (B4), (A2+B3) and (A2+B4) were applied to 1 g locks of hair.

After a leave-on time of 20 minutes at room temperature, the locks of hair were rinsed with water and wrung dry.

The locks were then subjected to 10 shampoo washes, made up of two cycles of five shampoo washes. After each shampoo wash cycle, the locks were dried and the colour of the locks was measured using a Minolta CM2600d spectrocolorimeter (specular components included, 10° angle, illuminant D65) in the CIEL*a*b* system.

In this system, L* represents the intensity of the colour, a* indicates the green/red colour axis and b* the blue/yellow colour axis.

The lower the value of L*, the darker or more intense the colour. The higher the value of a*, the redder the shade, and the higher the value of b*, the yellower the shade.

c) Results

The results of the colouring on the locks of hair containing 90% white hairs are given in the table below.

|  | Colour | L* | a* | b* |
|---|---|---|---|---|
| A2 | Intense blue | 37.20 | −13.47 | −16.12 |
| B3 | Red | 41.02 | 49.23 | 44.44 |
| B4 | Red | 38.42 | 46.87 | 38.15 |
| A2 + B3 | Brown with mahogany glints | 18.66 | 9.75 | 13.69 |
| A2 + B4 | Brown with mahogany glints | 19.73 | 6.43 | 10.28 |

The results obtained above show that the simultaneous application of a triarylmethane dye of formula (I) according to the present invention and of a fluorescent dye makes it possible to obtain very intense and chromatic colours.

These results also show that the process according to the invention, using only two particular direct dyes, a triarylmethane dye of formula (I) combined with a fluorescent dye, makes it possible to obtain brown colours, which are persistent even after 10 shampoo washes.

III. Comparative Example a) Preparation of the Compositions

Composition (A3) comprising a triarylmethane dye of formula (I) according to the invention, was prepared from the ingredients whose contents are mentioned in the table below.

|  | Composition A3 |
|---|---|
| [triarylmethane dye structure] | 0.2 |
| Monoethanolamine | pH = 9.5 |
| Water | qs 100 |

Composition (B5), comprising a fluorescent dye as defined in the patent application EP 1 133 975, was prepared from the ingredients whose contents are mentioned in the table below.

|  | Composition B5 |
|---|---|
| [fluorescent dye structure] | 0.2 |
| Monoethanolamine | pH = 9.5 |
| Water | qs 100 | b) Procedure

Compositions (A3) and (B5) obtained above were mixed so as to obtain the mixture (A3+B5) in a 1/1 ratio.

10 ml of compositions (A3), (B5) and (A3+B5) were applied to 1 g locks of hair.

After a leave-on time of 20 minutes at room temperature, the locks of hair were rinsed with water and wrung dry.

The locks were then subjected to one shampoo wash, and the colour of the locks was measured using a Minolta CM2600d spectrocolorimeter (specular components included, 10° angle, illuminant D65) in the CIEL*a*b* system.

In this system, L* represents the intensity of the colour, a* indicates the green/red colour axis and b* the blue/yellow colour axis.

The lower the value of L*, the darker or more intense the colour. The higher the value of a*, the redder the shade, and the higher the value of b*, the yellower the shade.

c) Results

The results of the colouring on the locks of hair containing 90% white hairs are given in the table below.

|   | Colour | L* | a* | b* |
|---|---|---|---|---|
| A3 | Intense blue | 42.07 | −8.33 | −14.86 |
| B5 | Yellow | 56.35 | 5.71 | 66.38 |
| A3 + B5 | Green | 40.68 | −19.27 | 21.98 |

The results obtained above show that the association of a triarylmethane dye of formula (I) according to the present invention and of a fluorescent dye, which is not chosen from cyanin, styryl/hemacyanin, and naphthalimide dyes, is not able to provide brown colours.

IV. Third Example of Combined Application a) Preparation of the Compositions Composition (A4) comprising a triarylmethane dye of formula (I) according to the invention, was prepared from the ingredients whose contents are mentioned in the table below.

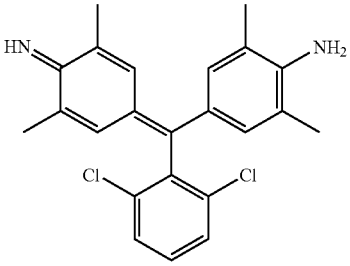 [SMILES: CC1=CC(=C(c2cc(C)c(N)c(C)c2)c2c(Cl)cccc2Cl)C=C(C)C1=N]

| | Composition A4 |
|---|---|
| | $10^{-3}$ mol % |
| Monoethanolamine | pH = 9.5 |
| Water | qs 100 |

Compositions (B6) and (M), comprising a fluorescent dye according to the present invention, were prepared from the ingredients whose contents are mentioned in the table below.

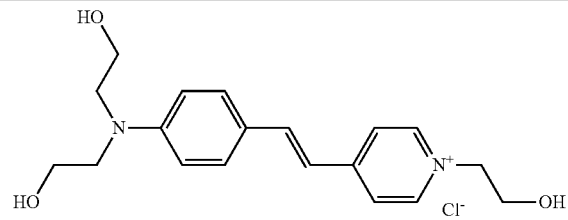 [SMILES: OCCN(CCO)c1ccc(/C=C/c2cc[n+](CCO)cc2)cc1 ; [Cl-]]

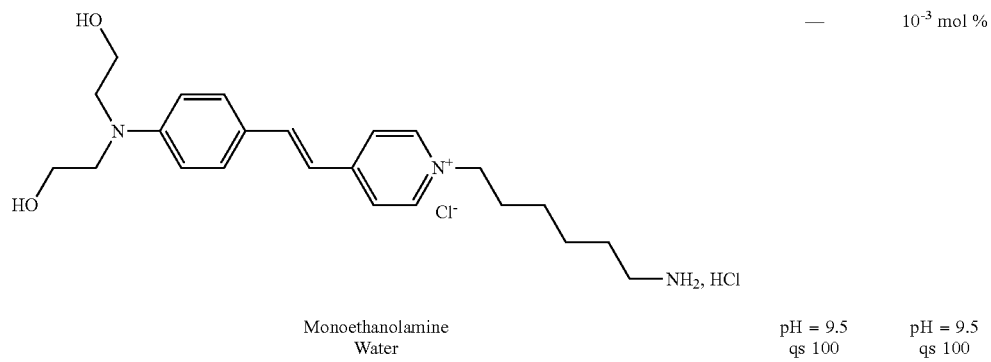

| | Composition B6 | Composition B7 |
|---|---|---|
| | $10^{-3}$ mol % | — |
| | — | $10^{-3}$ mol % |
| Monoethanolamine | pH = 9.5 | pH = 9.5 |
| Water | qs 100 | qs 100 | b) Procedure

Compositions (A4), (86) and (87) obtained above were mixed so as to obtain the following mixtures:

A4+B6 in a final concentration of $5*10^{-4}$ mol %, and
A4+B7 in a final concentration of $5*10^{-4}$ mol %.

10 ml of compositions (A4), (B6), (B7), (A4+B6) and (A4+B7) were applied to 1 g locks of hair. Compositions (A4), (B6) and (B7) were also applied in a final concentration of $5*10^{-4}$ mol %.

After a leave-on time of 20 minutes at room temperature, the locks of hair were rinsed with water and wrung dry.

The locks were then subjected to one shampoo wash, and the colour of the locks was measured using a Minolta CM2600d spectrocolorimeter (specular components included, 10° angle, illuminant D65) in the CIEL*a*b* system.

In this system, L* represents the intensity of the colour, a* indicates the green/red colour axis and b* the blue/yellow colour axis.

The lower the value of L*, the darker or more intense the colour. The higher the value of a*, the redder the shade, and the higher the value of b*, the yellower the shade.

c) Results

The results of the colouring on the locks of hair containing 90% white hairs are given in the table below.

|         | Colour              | L*    | a*     | b*     |
|---------|---------------------|-------|--------|--------|
| A4      | Intense blue        | 34.58 | −13.32 | −22.83 |
| B6      | Red                 | 39.51 | 51.04  | 42.13  |
| B7      | Orange              | 44.21 | 40.41  | 42.88  |
| A4 + B6 | Brown               | 22.03 | 15.07  | 13.77  |
| A4 + B7 | Brown with green glints | 29.21 | 7.01   | 10.76  |

The results obtained above show that the simultaneous application of a triarylmethane dye of formula (I) according to the present invention and of a fluorescent dye, chosen from cyanin, styryl/hemicyanin, and naphthalimide dyes, makes it possible to obtain very intense and chromatic colours.

These results also show that the process according to the invention, using only two particular direct dyes, a triarylmethane dye of formula (I) combined with a specific fluorescent dye, makes it possible to obtain brown colours, as well as brown with glints.

IV. Second Comparative Example of Combined Application a) Preparation of the Compositions Composition (A5) comprising a triarylmethane dye of formula (I) according to the invention, was prepared from the ingredients whose contents are mentioned in the table below.

|  | Composition A5 |
|---|---|
| [triarylmethane dye structure] | $10^{-3}$ mol % |
| Monoethanolamine | pH = 9.5 |
| Water | qs 100 |

Composition (B6), comprising a fluorescent dye according to the present invention, and composition (B8), comprising a fluorescent dye as defined in the patent application EP 1 133 975, were prepared from the ingredients whose contents are mentioned in the table below.

|  | Composition B6 | Composition B8 |
|---|---|---|
| [styryl/hemicyanin dye structure] | $10^{-3}$ mol % | — |
| [fluorescent dye structure] | — | $10^{-3}$ mol % |
| Monoethanolamine | pH = 9.5 | pH = 9.5 |
| Water | qs 100 | qs 100 | b) Procedure

Compositions (A4), (B6) and (B8) obtained above were mixed so as to obtain the following mixtures:

A5+B6 in a final concentration of $5*10^{-4}$ mol %, and

A5+B8 in a final concentration of $5*10^{-4}$ mol %.

10 ml of compositions (A5), (B6), (B8), (A5+B6) and (A5+B8) were applied to 1 g locks of hair. Compositions (A4), (B6) and (B8) were also applied in a final concentration of $5*10^4$ mol %.

After a leave-on time of 20 minutes at room temperature, the locks of hair were rinsed with water and wrung dry.

The locks were then subjected to one shampoo wash, and the colour of the locks was measured using a Minolta CM2600d spectrocolorimeter (specular components included, 100 angle, illuminant D65) in the CIEL*a*b* system.

In this system, L* represents the intensity of the colour, a* indicates the green/red colour axis and b* the blue/yellow colour axis.

The lower the value of L*, the darker or more intense the colour. The higher the value of a*, the redder the shade, and the higher the value of b*, the yellower the shade.

c) Results

The results of the colouring on the locks of hair containing 90% white hairs are given in the table below.

|  | Colour | L* | a* | b* |
|---|---|---|---|---|
| A5 | Intense blue | 41.45 | −8.63 | −13.11 |
| B6 | Red | 39.51 | 51.04 | 42.13 |
| B8 | Yellow | 61.48 | 6.86 | 71.59 |
| A5 + B6 | Brown with mahogany glints | 27.05 | 18.11 | 15.97 |
| A5 + B8 | Green | 36.03 | −14.49 | 17.4 |

The results obtained above show that the simultaneous application of a triarylmethane dye of formula (I) according to the present invention and of a fluorescent dye, chosen from cyanin, styryl/hemicyanin, and naphthalimide dyes (A5+B6), makes it possible to obtain very intense and chromatic colours.

These results also show that the process according to the invention, using only two particular direct dyes, a triarylmethane dye of formula (I) combined with a specific fluorescent dye, makes it possible to obtain brown colours.

In comparison, the association of a triarylmethane dye of formula (I) according to the present invention and of a fluorescent dye, which is not chosen from cyanin, styryl/hemicyanin, and naphthalimide dyes (A5+B8), is not able to provide brown colours and provide only green shades.

The invention claimed is:

1. A process for dyeing keratin fibres, comprising the application to said keratin fibres of the following ingredients:

(a) one or more triarylmethane dyes chosen from the compounds of formula (I) below, the optical isomers thereof, the geometrical isomers thereof, the tautomers thereof, the organic or mineral, acid or base salts thereof, the solvates thereof and mixtures thereof,

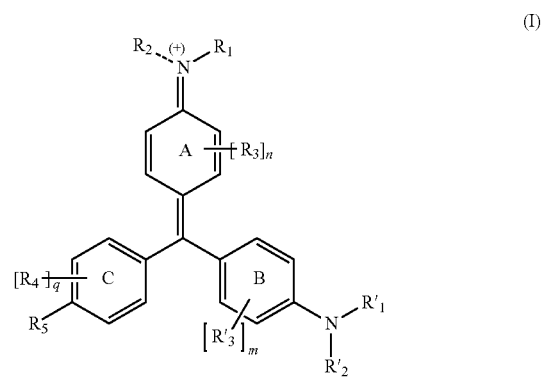

in which formula (I):

$R_1$, $R_2$, $R'_1$ and $R'_2$, which may be identical or different, represent:

a hydrogen atom, a linear or branched $C_1$ to $C_{20}$ alkyl radical;

that is optionally substituted and/or optionally interrupted with one or more heteroatoms, one or more groups comprising at least one heteroatom, or combinations thereof, or a benzyl radical optionally substituted with one or more $SO_3^-$ or $SO_3H$ groups;

$R_3$ and $R'_3$, which may be identical or different, represent, independently of each other:

a linear or branched $C_1$ to $C_6$ alkyl radical;

a sulfonate group $SO_3^-$, or a sulfonic group $SO_3H$;

n and m, which may be identical or different, represent two integers ranging from 0 to 4;

the radicals $R_4$, which may be identical or different, represent, independently of each other:

a linear or branched $C_1$ to $C_6$ alkyl radical;

a hydroxyl radical, a group $SO_3^-$, a group $SO_3H$, a halogen atom, or alternatively two adjacent radicals $R_4$ together form an unsaturated 6-membered ring, optionally substituted with one or more $SO_3^-$ or $SO_3H$ groups;

q is an integer ranging from 0 to 4;

$R_5$ represents:

a hydrogen atom, a halogen atom, an amino radical, a hydroxyl radical, an electron-withdrawing group $SO_3^-$ or $SO_3H$, or a radical —$NR_6R_7$, in which $R_6$ and $R_7$, which may be identical or different, represent, independently of each other:

a hydrogen atom, or a linear or branched $C_1$ to $C_6$ alkyl radical;

it being understood that:

the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and the compound of formula (I) optionally comprises one or more anions An⁻ and optionally one or more cations M⁺ to ensure the electrical neutrality of the molecule;

with:

An⁻ representing an anion; and

M⁺ representing a cation; and (b) one or more fluorescent dyes; said fluorescent dyes being direct dyes chosen from styryl dyes of formula (VIII) below, and also the organic or mineral acid or base salts thereof, the optical isomers, geometrical isomers and tautomers thereof, and the solvates thereof:

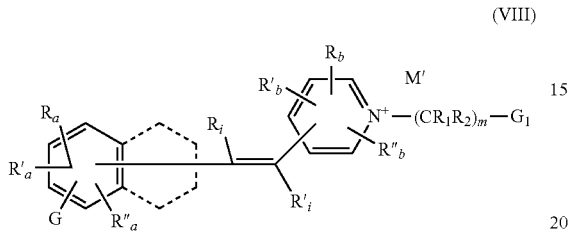
(VIII)

in which formula (VIII):

R₁ and R₂, which may be identical or different, represent a hydrogen atom or a $C_1$-$C_6$ alkyl group;

G₁ represents a hydrogen atom or a group chosen from NH₂ and OH;

$R_a$, $R'_a$, $R''_a$, $R_b$, $R'_b$ and $R''_b$ which may be identical or different, represent a) a hydrogen atom, b) a halogen atom, a group from among: c) amino, d) ($C_1$-$C_4$)alkylamino, e) ($C_1$-$C_4$)dialkylamino, f) cyano, g) carboxyl —C(O)OH or carboxylate —C(O)O⁻, Q⁺, h) hydroxyl —OH or alkoxide —O⁻Q⁺, i) (poly)halo ($C_1$-$C_6$)alkyl, j) acylamino, k) ($C_1$-$C_6$)alkoxy, l) ($C_1$-$C_6$)alkylthio, m) (poly)hydroxy($C_2$-$C_4$)alkoxy, n) ($C_1$-$C_6$)alkylcarbonyloxy, o) ($C_1$-$C_6$)alkoxycarbonyl, p) ($C_1$-$C_6$)alkylcarbonylamino, q) acylamino, r) carbamoyl, s) ($C_1$-$C_6$)alkylsulfonylamino, t) aminosulfonyl, u) —SO₃H or sulfonate —SO₃⁻, Q⁺ or v) ($C_1$-$C_6$)alkyl optionally substituted with a group chosen from ($C_1$-$C_6$)alkoxy, hydroxyl, cyano, carboxyl, amino, (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom;

or alternatively two groups $R_a$ and $R'_a$; $R_b$ and $R'_b$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, ($C_1$-$C_4$)alkylamino, ($C_1$-$C_4$)dialkylamino, nitro, cyano, carboxyl, hydroxyl or trifluoromethyl group, an acylamino, ($C_1$-$C_4$)alkoxy (poly)hydroxy($C_1$-$C_4$)alkoxy, ($C_1$-$C_4$)alkylcarbonyloxy, ($C_1$-$C_4$)alkoxycarbonyl or ($C_1$-$C_4$)alkylcarbonylamino radical, an acylamino, carbamoyl or alkoxyalkylsulfonylamino radical, an aminosulfonyl radical, or a ($C_1$-$C_6$)alkyl radical optionally substituted with: a group chosen from ($C_1$-$C_6$)alkoxy, hydroxyl, cyano, carboxyl, amino, ($C_1$-$C_4$)alkylamino and ($C_1$-$C_4$)dialkylamino, or alternatively the two alkyl radicals borne by the nitrogen atom of the amino group form a 5- to 7-membered heterocycle optionally comprising another nitrogen or non-nitrogen heteroatom;

or alternatively, two groups $R_i$ and $R_a$; and/or a group $R'_i$ and $R'_a$ together form a fused (hetero)cycloalkyl;

G represents i) a group —NR$_c$R$_d$, ii) —OR with R representing a) a hydrogen atom, b) an optionally substituted, c) an optionally substituted (hetero)aryl group, d) an optionally substituted (hetero)aryl($C_1$-$C_6$)alkyl group, e) optionally substituted (hetero)cycloalkyl, f) optionally substituted (hetero)cycloalkyl($C_1$-$C_6$)alkyl;

or alternatively when G represents —NR$_c$R$_d$, two groups R$_c$ and R'$_a$ and/or R$_d$ and R$_a$ together form a saturated heteroaryl or heterocycle, optionally substituted with one or more ($C_1$-$C_6$)alkyl groups;

R$_i$ and R'$_i$, which may be identical or different, represent a hydrogen atom or a ($C_1$-$C_4$)alkyl group;

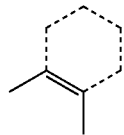

represents an aryl or heteroaryl group fused to the phenyl ring; or alternatively is absent from the phenyl ring;

m represents an integer between 1 and 18 inclusive; and

M' representing an anionic counterion, derived from a salt of an organic or mineral acid, or from an organic or mineral base that ensures the electrical neutrality of the dye it being understood that the triarylmethane dye(s) (a) and the fluorescent dye(s) (b) are applied to said keratin fibres together or sequentially.

2. The process according to claim 1, characterized in that n and m, which may be identical or different, represent two integers ranging from 0 to 2.

3. The process according to claim 1, characterized in that R₁, R₂, R'₁ and R'₂, which may be identical or different, represent, independently of each other:

a hydrogen atom, a linear or branched $C_1$ to $C_6$ alkyl radical, which is optionally substituted, and/or optionally interrupted with one or more heteroatoms chosen from oxygen and sulfur, and/or with one or more groups comprising at least one heteroatom, or a benzyl radical substituted with an SO₃⁻ group.

4. The process according to claim 1, characterized in that R₅ represents:

a hydrogen atom, an SO₃⁻ group, or a radical —NR₆R₇, with R₆ and R₇, which may be identical or different, representing, independently of each other, a hydrogen atom or a linear or branched $C_1$ to $C_6$ alkyl radical.

5. The process according to claim 1, characterized in that the triarylmethane dye(s) are cationic and are chosen from the compounds of formula (I-cat) below:

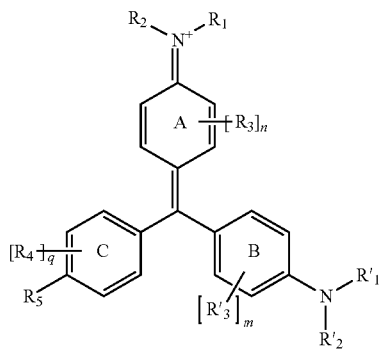

(I-cat)

in which formula (I-cat):
$R_1$, $R_2$, $R'_1$ and $R'_2$, which may be identical or different, represent:
a hydrogen atom,
a linear or branched $C_1$ to $C_{20}$ alkyl radical;
that is optionally substituted and/or
optionally interrupted with one or more heteroatoms, one or more groups comprising at least one heteroatom or combinations thereof, or
a benzyl radical optionally substituted with one or more $SO_3^-$ or $SO_3H$ groups;
$R_3$ and $R'_3$, which may be identical or different, represent, independently of each other:
a linear or branched $C_1$ to $C_6$ alkyl radical;
a sulfonate group $SO_3^-$, or
a sulfonic group $SO_3H$;
n and m, which may be identical or different, represent two integers ranging from 0 to 4;
the radicals $R_4$, which may be identical or different, represent, independently of each other:
a linear or branched $C_1$ to $C_6$ alkyl radical;
a hydroxyl radical,
a group $SO_3^-$,
a group $SO_3H$,
a halogen atom,
or alternatively two adjacent radicals $R_4$ together form an unsaturated 6-membered ring optionally substituted with one or more $SO_3^-$ or $SO_3H$ groups;
q is an integer ranging from 0 to 4;
$R_5$ represents:
a hydrogen atom,
a halogen atom,
an amino radical,
a hydroxyl radical,
an electron-withdrawing group $SO_3^-$ or $SO_3H$, or
a radical —$NR_6R_7$, in which $R_6$ and $R_7$, which may be identical or different, represent, independently of each other:
a hydrogen atom, or
a linear or branched $C_1$ to $C_6$ alkyl radical;
it being understood that:
the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and
it being understood that (I-cat) does not comprise more than one sulfonate group.

6. The process according to claim 1, characterized in that the triarylmethane dye(s) are anionic and are chosen from the compounds of formula (I-an') or (I-an") below:

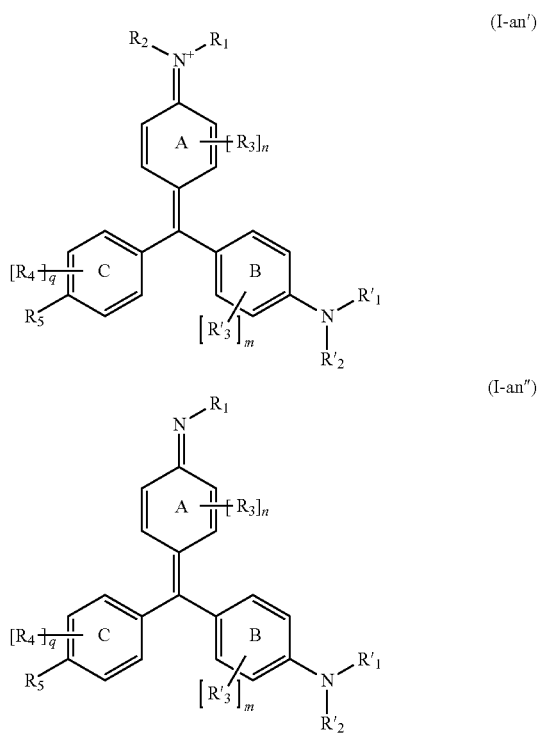

(I-an')

(I-an")

in which formula (I-an') or (I-an"):
$R_1$, $R_2$, $R'_1$ and $R'_2$, which may be identical or different, represent:
a hydrogen atom,
a linear or branched $C_1$ to $C_{20}$ alkyl radical;
that is optionally substituted and/or
optionally interrupted with one or more heteroatoms, one or more groups comprising at least one heteroatom, or combinations thereof, or
a benzyl radical optionally substituted with one or more $SO_3^-$ or $SO_3H$ groups;
$R_3$ and $R'_3$, which may be identical or different, represent, independently of each other:
a linear or branched $C_1$ to $C_6$ alkyl radical;
a sulfonate group $SO_3^-$, or
a sulfonic group $SO_3H$;
n and m, which may be identical or different, represent two integers ranging from 0 to 4;
the radicals $R_4$, which may be identical or different, represent, independently of each other:
a linear or branched $C_1$ to $C_6$ alkyl radical;
a hydroxyl radical,
a group $SO_3^-$,
a group $SO_3H$,
a halogen atom,
or alternatively two adjacent radicals $R_4$ together form an unsaturated 6-membered ring, optionally substituted with one or more $SO_3^-$ or $SO_3H$ groups;
q is an integer ranging from 0 to 4;
$R_5$ represents:
a hydrogen atom,
a halogen atom,
an amino radical,
a hydroxyl radical,
an electron-withdrawing group $SO_3^-$ or $SO_3H$, or
a radical —$NR_6R_7$, in which $R_6$ and $R_7$, which may be identical or different, represent, independently of
each other:

a hydrogen atom, or
a linear or branched $C_1$ to $C_6$ alkyl radical;
it being understood that:
the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and
it being understood that:
(I-an') comprises at least two sulfonate groups on ring A, B or C,
(I-an") comprises at least one sulfonate group on ring A, B or C, and
one or more cation(s) $M^+$ are present to compensate for the anionic charge(s) of the sulfonate group(s), wherein $M^+$ is chosen from sodium, potassium, magnesium, calcium, zinc, and ammonium ions, or a mixture of these ions.

7. The process according to claim 1, characterized in that the triarylmethane dye(s) are nonionic and are chosen from the compounds of formula (I-nion) below:

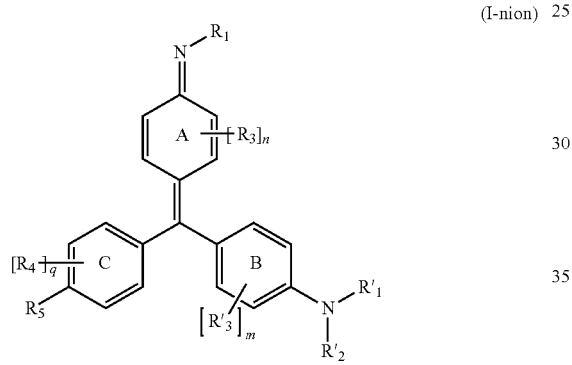

(I-nion)

in which formula (I-nion):
$R_1$, $R_2$, $R'_1$ and $R'_2$, which may be identical or different, represent:
a hydrogen atom,
a linear or branched $C_1$ to $C_{20}$ alkyl radical;
that is optionally substituted and/or
optionally interrupted with one or more heteroatoms, one or more groups comprising at least one heteroatom, or combinations thereof, or
a benzyl radical optionally substituted with one or more $SO_3^-$ or $SO_3H$ groups;
$R_3$ and $R'_3$, which may be identical or different, represent, independently of each other:
a linear or branched $C_1$ to $C_6$ alkyl radical;
a sulfonate group $SO_3^-$, or
a sulfonic group $SO_3H$;
n and m, which may be identical or different, represent two integers ranging from 0 to 4;
the radicals $R_4$, which may be identical or different, represent, independently of each other:
a linear or branched $C_1$ to $C_6$ alkyl radical;
a hydroxyl radical,
a group $SO_3^-$,
a group $SO_3H$,
a halogen atom,
or alternatively two adjacent radicals $R_4$ together form an unsaturated 6-membered ring optionally substituted with one or more $SO_3^-$ or $SO_3H$ groups;
q is an integer ranging from 0 to 4;
$R_5$ represents:
a hydrogen atom,
a halogen atom,
an amino radical,
a hydroxyl radical,
an electron-withdrawing group $SO_3^-$ or $SO_3H$, or
a radical $—NR_6R_7$, in which $R_6$ and $R_7$, which may be identical or different, represent, independently of each other:
a hydrogen atom, or
a linear or branched $C_1$ to $C_6$ alkyl radical;
it being understood that:
the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and
it being understood that (I-nion) does not comprise any sulfonate groups on ring A, B or C.

8. The process according claim 1, characterized in that the triarylmethane dye(s) (a) are chosen from the following compounds, the optical isomers thereof, the geometrical isomers thereof, the tautomers thereof, the organic or mineral, acid or base salts thereof, the solvates thereof, and mixtures thereof:

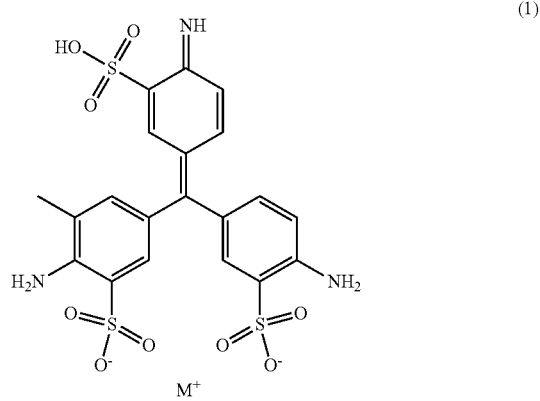

(1)

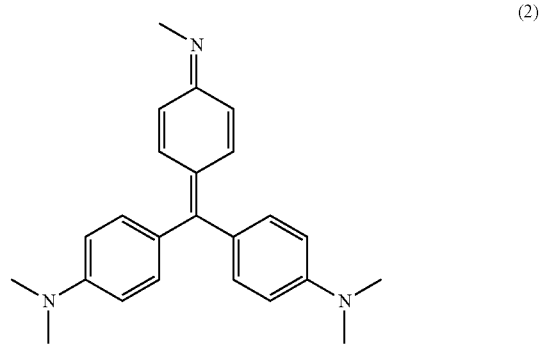

(2)

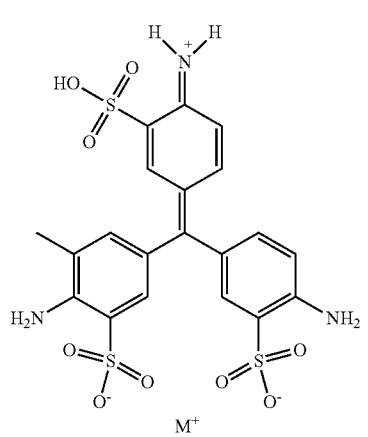
(1')
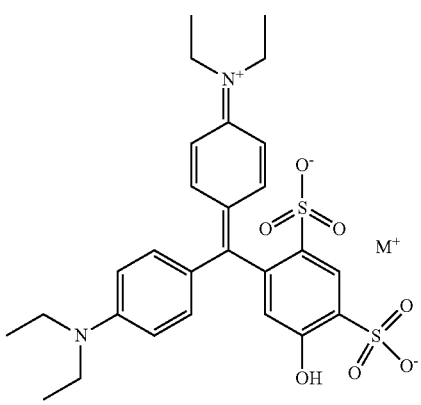
(5)
(2')
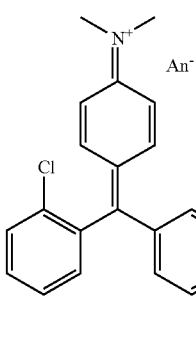
(6)
(3)
(4)
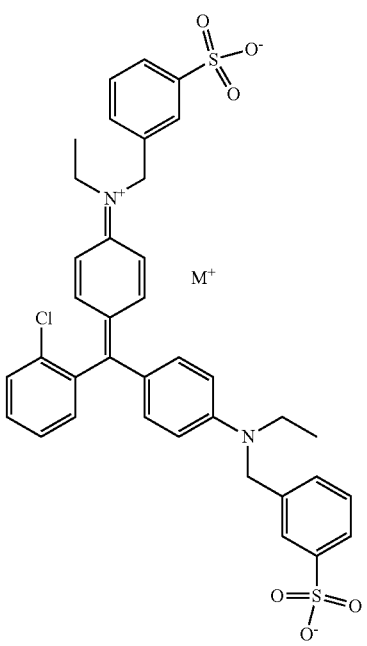
(7)

(8)
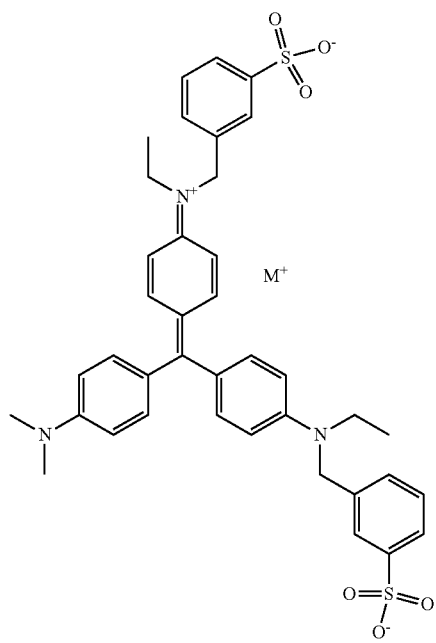
(9)
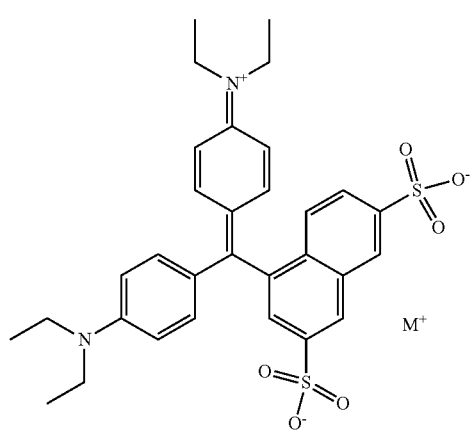
(10)
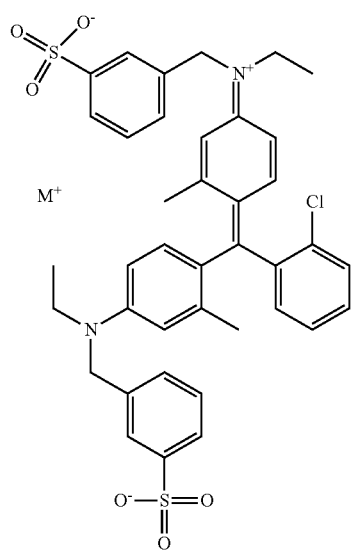
(11)
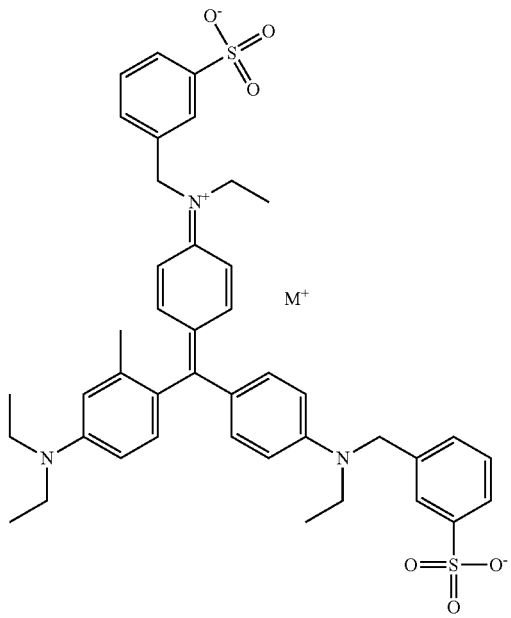
(12)
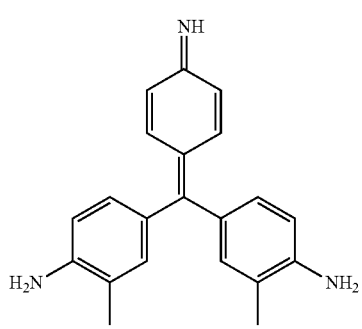
(13)
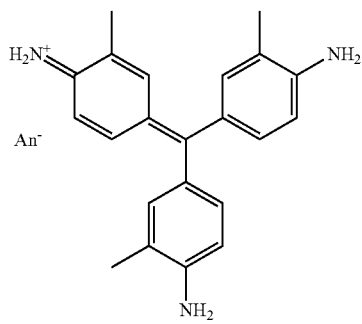
(14)
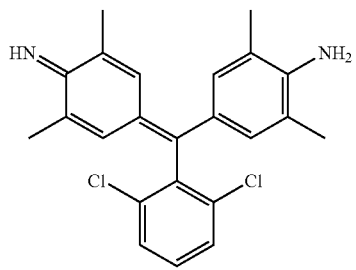 [SMILES: CC1=CC(=C(c2cc(C)c(N)c(C)c2)c2c(Cl)cccc2Cl)C=C(C)C1=N]

-continued (15)

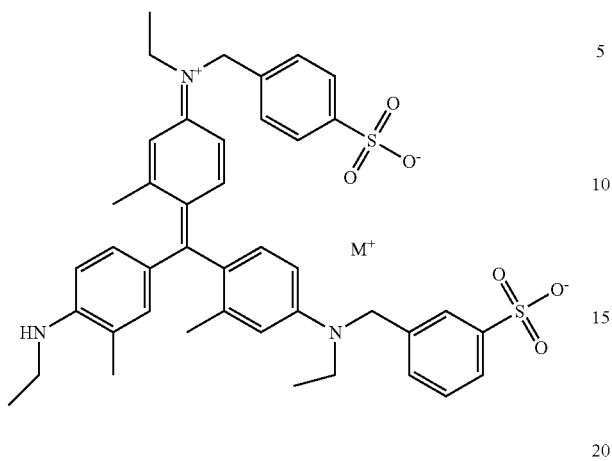

9. The process according to claim 1, characterized in that the fluorescent dye(s) (b) are chosen from the styryl dyes of formula (IX) below, and also the organic or mineral acid or base salts thereof, the optical isomers, geometrical isomers and tautomers thereof, and the solvates thereof:

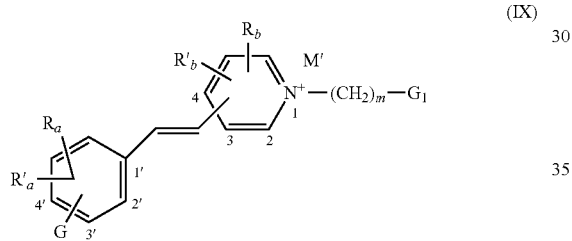

(IX)

in which formula (IX)

G represents a group —$NR_cR_d$ or ($C_1$-$C_6$)alkoxy group which is optionally substituted;

$G_1$ represents a hydrogen atom or a group chosen from $NH_2$ and OH;

$R_a$, and $R'_a$, which may be identical or different, represent a hydrogen atom, a halogen atom, or an —OH, —$O^-Q^+$, ($C_1$-$C_6$)alkoxy, nitro, or cyano group, wherein $Q^+$ represents a cationic counterion, derived from a salt of an organic or mineral acid, or from an organic or mineral base that ensures the electrical neutrality of the dye;

$R_b$, and $R'_b$, which may be identical or different, represent a hydrogen atom or a ($C_1$-$C_6$)alkyl group; and m represents an integer between 1 and 18 inclusive.

10. Process according to claim 1, characterized in that the fluorescent dye(s) (b) are chosen from the compounds of formulae (X), (XI), (XII) and (XIII) below, and also the organic or mineral acid or base salts thereof, the optical isomers, geometrical isomers and tautomers thereof, and the solvates thereof:

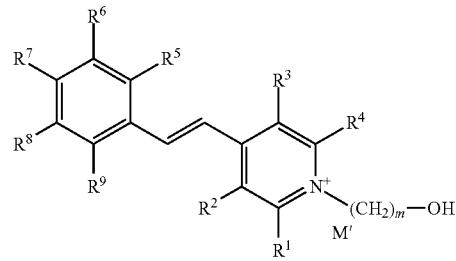

(X)

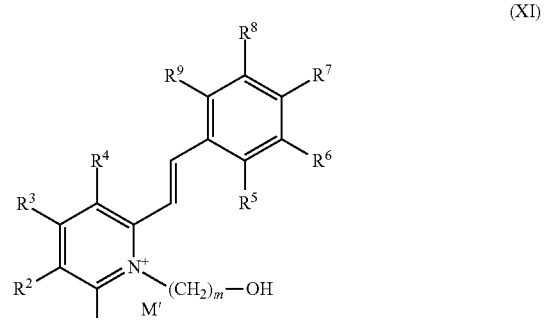

(XI)

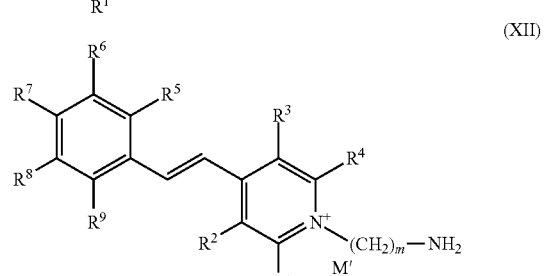

(XII)

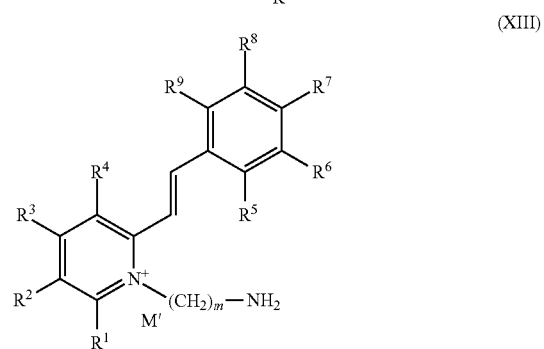

(XIII)

in which formulae (X), (XI), (XII) and (XIII):

$R^1$, $R_2$, $R_3$ and $R_4$, which may be identical or different, represent a hydrogen atom or a ($C_1$-$C_6$)alkyl group;

$R^5$, $R^6$, $R^7$, $R^8$ and $R^9$, which may be identical or different, represent i) a hydrogen atom or ii) a halogen atom, iii) a group OR in which R represents a hydrogen atom or $Q^+$, or a ($C_1$-$C_3$)alkyl group, a group from among iv) aryl, v) aryl($C_1$-$C_3$)alkyl, vi) cyano, vii) nitro, viii) ($C_1$-$C_3$)alkylthio, ix) amino $NR^{10}R^{11}$ with $R^{10}$ and $R^{11}$, which may be identical or different, representing a) a hydrogen atom, b) a ($C_2$-$C_4$)alkyl group or c) a substituted ($C_1$-$C_8$)alkyl group;

m represents an integer between 1 and 18 inclusive;

M' represents an anionic counterion derived from a salt of an organic or mineral acid, or from an organic or mineral base that ensures the electrical neutrality of the dye; and Q⁺ represents a cationic counterion, derived from a salt of an organic or mineral acid, or from an organic or mineral base that ensures the electrical neutrality of the dye;

it being understood that when the dye comprises an alkoxide group, then M' and Q⁺ may be absent to ensure the electrical neutrality of said dye.

11. The process according to claim 10, characterized in that the fluorescent dye(s) (b) of the invention are chosen from those of formulae (XIV) and (XV) below:

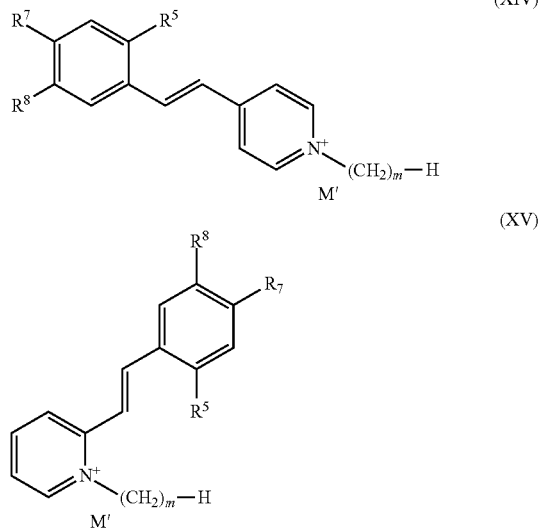

in which formulae (XIV) and (XV) $R^5$, $R^7$, $R^8$ and m are:
$R^5$ and $R^8$, which may be identical or different, represent a hydrogen atom or a $(C_1-C_4)$alkoxy group;
$R^7$ represents a $(C_1-C_4)$alkoxy group or $NR^{10}R^{11}$ with $R^{10}$ and $R^{11}$, which may be identical or different, representing a) a hydrogen atom, or b) a $(C_1-C_8)$ alkyl group optionally substituted with one or more groups chosen from i) hydroxyl, ii) R—Z—C(X)—Y— with X, Y and Z representing an oxygen or sulfur atom or N(R'), or alternatively X and/or Z represent a bond, R and R', which may be identical or different, represent a hydrogen atom or a $(C_1-C_6)$ alkyl group, iii) sulfonic $SO_3H$, iv) sulfonate $SO_3^-$, Q⁺, or v) carboxylate $C(O)O^-$, Q⁺ with Q⁺ representing a cationic counterion;
m represents an integer between 1 and 18 inclusive; and M' represents an anionic counterion, derived from a salt of an organic or mineral acid, or from an organic or mineral base that ensures the electrical neutrality of the dye;

it being understood that when the dye comprises an alkoxide group, then M' and Q⁺ may be absent to ensure the electrical neutrality of said dye.

12. The process according to claim 10, characterized in that the fluorescent dye(s) (b) are chosen from:
the fluorescent dyes of formula (X) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| H | H | H | H | H | H | H | H | H | 1 |
| H | H | H | H | H | t-Bu | OH | t-Bu | H | 5 |
| H | H | H | H | H | t-Bu | OH | t-Bu | H | 5 |
| H | H | H | H | H | H | $NH_2$ | H | H | 1 |
| H | H | H | H | H | H | $NH_2$ | H | $OCH_3$ | 1 |
| H | H | H | H | H | H | OH | Br | H | 5 |
| H | H | H | H | H | $OCH_3$ | OH | $OCH_3$ | H | 5 |
| H | H | H | H | Cl | H | OH | H | Cl | 5 |
| H | H | H | H | H | H | OH | H | H | 10 |
| H | H | H | H | H | $OCH_3$ | OH | $OCH_3$ | H | 10 |
| H | H | H | H | H | t-Bu | OH | t-Bu | H | 10 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | t-Bu | OH | t-Bu | H | 10 |
| H | H | H | H | H | H | $N(CH_2CH_3)CH_2CH_2OH$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $N(CH_2CH_3)_2$ | H | H | 1 |
| H | H | H | H | H | H | $n-C_6H_{13}$ | H | H | 1 |
| H | H | H | H | H | H | $N(CH_2CH_2OH)_2$ | H | H | 2 |
| H | H | H | H | H | H | $N(n-Bu)_2$ | H | H | 2 |
| H | H | H | H | H | $OCH_3$ | OH | H | H | 10 |
| H | H | H | H | H | H | $OC_2H_5$ | OH | H | 1 |
| H | H | H | H | H | H | OH | H | H | 1 |
| H | H | benzo | H | H | H | H | H | 1 |
| H | H | benzo | H | H | $N(CH_2CH_2OH)_2$ | H | H | 1 |
| H | H | benzo | H | H | $N(CH_2CH_2OH)_2$ | H | H | 1 | and also the organic or mineral acid or base salts thereof, the optical isomers, geometrical isomers and tautomers thereof, and the solvates thereof;
the fluorescent dyes of formula (XI) with:

| $R^1$ | $R^2$ | $R^3$ | $R^4$ | $R^5$ | $R^6$ | $R^7$ | $R^8$ | $R^9$ | m |
|---|---|---|---|---|---|---|---|---|---|
| $CH_3$ | H | H | H | OH | H | $OCH_3$ | H | H | 2 |
| $CH_3$ | H | H | H | H | H | $OCH_3$ | $OCH_2$-Ph | H | 2 |
| $CH_3$ | H | H | H | H | H | H | H | $OCH_3$ | 2 |
| $CH_3$ | H | H | H | F | H | H | H | H | 2 |
| $CH_3$ | H | H | H | H | H | H | OPh | H | 2 |
| $CH_3$ | H | H | H | H | H | $N(CH_2CH_2OAc)_2$ | H | H | 2 |
| $CH_3$ | H | H | H | $OCH_3$ | H | $OCH_3$ | $OCH_3$ | H | 2 |
| $CH_3$ | H | H | H | H | H | H | $CH_3$ | H | 2 |
| $CH_3$ | H | H | H | H | H | OH | H | H | 2 |
| $CH_3$ | H | H | H | H | $OCH_3$ | $OCH_3$ | $OCH_3$ | H | 2 |
| $CH_3$ | H | H | H | H | $OCH_3$ | OH | OH | H | 2 |
| $CH_3$ | H | H | H | H | H | $OCH_3$ | $OCH_3$ | $OCH_3$ | 2 |
| $CH_3$ | H | H | H | H | H | H | $OCH_3$ | OH | 2 |
| $CH_3$ | H | H | H | H | H | $N(n-butyl)_2$ | H | H | 2 |

-continued

| R¹ | R² | R³ | R⁴ | R⁵ | R⁶ | R⁷ | R⁸ | R⁹ | m |
|---|---|---|---|---|---|---|---|---|---|
| CH₃ | H | H | H | H | OCH₃ | OCH₃ | H | H | 2 |
| CH₃ | H | H | H | H | H | H | H | H | 2 |
| CH₃ | H | H | H | H | H | i-propyl | H | H | 2 |
| H | H | H | H | H | H | OH | H | H | 6 |
| H | H | H | H | H | OCH₃ | OCH₃ | OCH₃ | H | 6 |
| H | H | H | H | OH | H | OCH₃ | H | H | 2 |
| H | H | H | H | OCH₃ | H | H | OCH₃ | OCH₃ | 2 |
| H | H | H | H | H | H | H | H | Br | 2 |
| H | H | H | H | H | H | OH | H | H | 2 |
| H | H | H | H | OCH₃ | OCH₃ | OCH₃ | H | H | 6 |
| H | H | H | H | OH | OCH₃ | H | H | H | 6 |
| H | H | H | H | H | OCH₃ | OCH₃ | H | H | 6 |
| H | H | H | H | H | OCH₃ | OCH₃ | H | H | 2 |
| H | H | H | H | H | H | C(O)—OH | H | H | 6 |
| H | H | H | H | H | H | C(O)—OH | H | H | 2 |
| H | H | H | H | H | H | i-propyl | H | H | 2 |
| H | H | H | H | H | H | N(CH₃)CH₂CH₂CN | H | H | 2 |
| H | H | H | H | H | H | OCH₃ | OCH₂Ph | H | 2 |
| H | H | H | H | H | H | H | OPh | H | 2 |
| H | H | H | H | H | H | N(CH₂CH₂C(O)CH₃)₂ | H | H | 2 |
| H | H | H | H | OH | H | OCH₃ | H | H | 6 |
| H | H | H | H | H | OCH₃ | OCH₃ | OCH₃ | H | 2 |
| H | H | H | H | OCH₃ | H | OCH₃ | OCH₃ | H | 6 |
| H | H | H | H | H | H | H | CH₃ | H | 2 |
| H | H | H | H | H | H | N(CH₃)CH₂CH₂OH | H | H | 2 | and also the organic or mineral acid or base salts thereof, the geometrical isomers and tautomers thereof, and the solvates thereof;

the fluorescent dyes of formulae (X') and (XI'):

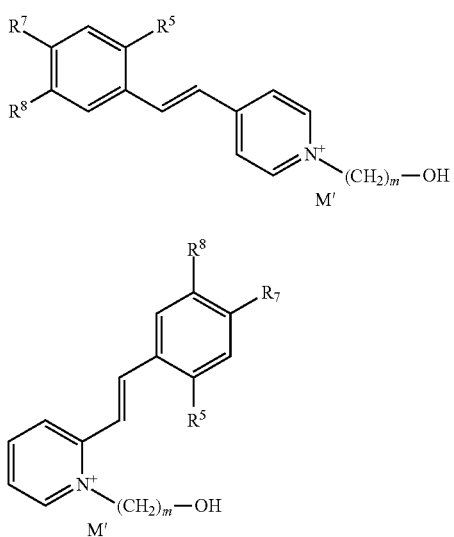

(X')

(XI')

wherein M' represents an anionic counterion, derived from a salt of an organic or mineral acid, or from an organic or mineral base that ensures the electrical neutrality of the dye; and

| R⁵ | R⁷ | R⁸ | m |
|---|---|---|---|
| H | N(CH₂CH₂OH)₂ | H | 2 |
| H | N(CH₂CH₂OH)₂ | H | 3 |
| H | N(CH₂CH₂OH)₂ | H | 4 |
| H | N(CH₂CH₂OH)₂ | H | 5 |
| H | N(CH₂CH₂OH)₂ | H | 6 |

-continued

| R⁵ | R⁷ | R⁸ | m |
|---|---|---|---|
| H | N(CH₂CH₂OH)₂ | H | 8 |
| H | N(CH₂CH₂OH)₂ | H | 10 |
| H | N(CH₂CH₂OH)₂ | H | 12 |
| H | N(CH₂CH₂OH)₂ | H | 14 |
| H | N(CH₂CH₂OH)₂ | H | 16 |
| H | CH₃CH₂N(CH₂CH₂OH) | H | 2 |
| H | CH₃CH₂N(CH₂CH₂OH) | H | 4 |

| R⁵ | R⁷ | R⁸ | m |
|---|---|---|---|
| OCH₃ | OCH₃ | OCH₃ | 2 |
| OCH₃ | OCH₃ | OCH₃ | 3 |
| OCH₃ | OCH₃ | OCH₃ | 3 |
| OCH₃ | OCH₃ | OCH₃ | 4 |
| OCH₃ | OCH₃ | OCH₃ | 5 |
| OCH₃ | OCH₃ | OCH₃ | 8 |
| OCH₃ | OCH₃ | OCH₃ | 10 |
| OCH₃ | OCH₃ | OCH₃ | 12 |
| OCH₃ | OCH₃ | OCH₃ | 14 |
| OCH₃ | OCH₃ | OCH₃ | 16 | and and also the organic or mineral acid or base salts thereof, the geometrical isomers and tautomers thereof, and the solvates thereof;

the fluorescent dyes of formula (XII) with:

| R¹ | R² | R³ | R⁴ | R⁵ | R⁶ | R⁷ | R⁸ | R⁹ | m |
|---|---|---|---|---|---|---|---|---|---|
| H | H | H | H | H | H | OCH₃ | OCH₃ | OCH | 2 |
| H | H | H | H | OH | OCH₃ | H | H | H | 2 |
| H | H | H | H | H | H | H | H | H | 2 |
| H | H | H | H | H | OCH₃ | OCH₃ | H | H | 2 |
| H | H | H | H | OH | H | OH | H | H | 6 |
| H | H | H | H | OCH₃ | H | OCH₃ | OCH₃ | H | 6 |
| H | H | H | H | H | H | OH | H | H | 6 |
| H | H | H | H | OCH₃ | H | H | H | F | 2 |
| H | H | H | H | H | H | C(O)—OH | H | H | 2 |

-continued

| R¹ | R² | R³ | R⁴ | R⁵ | R⁶ | R⁷ | R⁸ | R⁹ | m |
|---|---|---|---|---|---|---|---|---|---|
| H | H | H | H | H | H | Isopropyl | H | H | 2 |
| H | H | H | H | H | H | $N(CH_2CH_2C(O)CH_3)_2$ | H | H | 2 |
| H | H | H | H | OH | $OCH_3$ | H | H | H | 2 |
| H | H | H | H | H | H | OH | H | H | 2 |
| H | H | H | H | H | $OCH_3$ | OH | OH | H | 2 |
| H | H | H | H | H | $CH_3$ | $OCH_2Ph$ | $CH_3$ | H | 2 |
| H | H | H | H | H | $OCH_3$ | $OCH_3$ | $OCH_3$ | H | 2 |
| H | H | H | H | H | $OCH_3$ | $OCH_3$ | $OCH_3$ | H | 6 |
| H | H | H | H | H | H | $N(CH_3)_2$ | H | H | 6 |
| H | H | H | H | H | H | $OCH_3$ | $OCH_3$ | $OCH_3$ | 6 |
| H | H | H | H | H | H | Phenyl | H | H | 6 |
| H | H | H | H | H | $OCH_3$ | $OCH_3$ | H | H | 6 |
| H | H | H | H | H | H | C(O)—OH | H | H | 6 |
| H | H | H | H | H | H | $N(n\text{-Butyl})_2$ | H | H | 2 |
| H | H | H | H | H | H | $OCH_3$ | $OCH_3$ | H | 3 |
| H | H | H | H | H | H | $OCH_3$ | $OCH_3$ | H | 2 |
| H | H | H | H | H | H | $OCH_3$ | $OCH_3$ | H | 5 |
| H | H | H | H | H | H | $OCH_3$ | H | H | 3 |
| H | H | H | H | H | H | $N(CH_3)_2$ | H | H | 3 |
| H | H | H | H | H | H | H | H | H | 3 | and also the organic or mineral acid or base salts thereof, the optical isomers, geometrical isomers and tautomers thereof, and the solvates thereof;

the fluorescent dyes of formula (XIII) with:

| R¹ | R² | R³ | R⁴ | R⁵ | R⁶ | R⁷ | R⁸ | R⁹ | m |
|---|---|---|---|---|---|---|---|---|---|
| $CH_3$ | H | H | H | OH | H | $OCH_3$ | H | H | 2 |
| $CH_3$ | H | H | H | H | H | $OCH_3$ | $OCH_2$-Ph | H | 2 |
| $CH_3$ | H | H | H | H | H | H | H | $OCH_3$ | 2 |
| $CH_3$ | H | H | H | F | H | H | H | H | 2 |
| $CH_3$ | H | H | H | H | H | H | OPh | H | 2 |
| $CH_3$ | H | H | H | H | H | $N(CH_2CH_2OAc)_2$ | H | H | 2 |
| $CH_3$ | H | H | H | $OCH_3$ | H | $OCH_3$ | $OCH_3$ | H | 2 |
| $CH_3$ | H | H | H | H | H | H | $CH_3$ | H | 2 |
| $CH_3$ | H | H | H | H | H | OH | H | H | 2 |
| $CH_3$ | H | H | H | H | $OCH_3$ | $OCH_3$ | $OCH_3$ | H | 2 |
| $CH_3$ | H | H | H | H | $OCH_3$ | OH | OH | H | 2 |
| $CH_3$ | H | H | H | H | H | $OCH_3$ | $OCH_3$ | $OCH_3$ | 2 |
| $CH_3$ | H | H | H | H | H | H | $OCH_3$ | OH | 2 |
| $CH_3$ | H | H | H | H | H | $N(n\text{-butyl})_2$ | H | H | 2 |
| $CH_3$ | H | H | H | H | $OCH_3$ | $OCH_3$ | H | H | 2 |
| $CH_3$ | H | H | H | H | H | H | H | H | 2 |
| $CH_3$ | H | H | H | H | H | i-propyl | H | H | 2 |
| H | H | H | H | H | H | OH | H | H | 6 |
| H | H | H | H | H | $OCH_3$ | $OCH_3$ | $OCH_3$ | H | 6 |
| H | H | H | H | OH | H | $OCH_3$ | H | H | 2 |
| H | H | H | H | $OCH_3$ | H | H | $OCH_3$ | $OCH_3$ | 2 |
| H | H | H | H | H | H | H | H | Br | 2 |
| H | H | H | H | H | H | OH | H | H | 2 |
| H | H | H | H | H | H | $N(CH_3)_2$ | H | H | 6 |
| H | H | H | H | $OCH_3$ | $OCH_3$ | $OCH_3$ | H | H | 6 |
| H | H | H | H | OH | $OCH_3$ | H | H | H | 6 |
| H | H | H | H | H | $OCH_3$ | $OCH_3$ | H | H | 6 |
| H | H | H | H | H | $OCH_3$ | $OCH_3$ | H | H | 2 |
| H | H | H | H | H | H | C(O)—OH | H | H | 6 |
| H | H | H | H | H | H | C(O)—OH | H | H | 2 |
| H | H | H | H | H | H | i-propyl | H | H | 2 |
| H | H | H | H | H | H | $N(CH_3)CH_2CH_2CN$ | H | H | 2 |
| H | H | H | H | H | H | $OCH_3$ | $OCH_2Ph$ | H | 2 |
| H | H | H | H | H | H | H | OPh | H | 2 |
| H | H | H | H | OH | H | $N(CH_2CH_2C(O)CH_3)_2$ | H | H | 2 |
| H | H | H | H | OH | H | $OCH_3$ | H | H | 6 |
| H | H | H | H | H | $OCH_3$ | $OCH_3$ | $OCH_3$ | H | 2 |
| H | H | H | H | $OCH_3$ | H | $OCH_3$ | $OCH_3$ | H | 6 |
| H | H | H | H | H | H | H | $CH_3$ | H | 2 |
| H | H | H | H | H | H | $N(CH_3)CH_2CH_2OH$ | H | H | 2 |
| $CH_3$ | H | H | H | H | H | $N(CH_3)_2$ | H | H | 2 | and also the organic or mineral acid or base salts thereof, the geometrical isomers and tautomers thereof, and the solvates thereof; and the fluorescent dyes of formulae (XII') and (XIII') below:

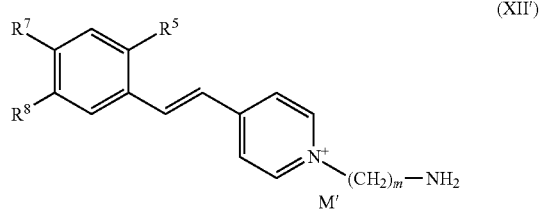

(XII')

-continued

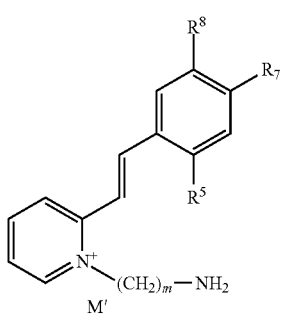

(XIII')

with:

| R⁵ | R⁷ | R⁸ | m |
|---|---|---|---|
| H | N(CH₂CH₂OH)₂ | H | 2 |
| H | N(CH₂CH₂OH)₂ | H | 3 |
| H | N(CH₂CH₂OH)₂ | H | 4 |
| H | N(CH₂CH₂OH)₂ | H | 5 |
| H | N(CH₂CH₂OH)₂ | H | 6 |
| H | N(CH₂CH₂OH)₂ | H | 8 |
| H | N(CH₂CH₂OH)₂ | H | 10 |
| H | N(CH₂CH₂OH)₂ | H | 12 |
| H | N(CH₂CH₂OH)₂ | H | 14 |
| H | N(CH₂CH₂OH)₂ | H | 16 | and

| R⁵ | R⁷ | R⁸ | m |
|---|---|---|---|
| OCH₃ | OCH₃ | OCH₃ | 2 |
| OCH₃ | OCH₃ | OCH₃ | 3 |
| OCH₃ | OCH₃ | OCH₃ | 3 |
| OCH₃ | OCH₃ | OCH₃ | 4 |
| OCH₃ | OCH₃ | OCH₃ | 5 |
| OCH₃ | OCH₃ | OCH₃ | 8 |
| OCH₃ | OCH₃ | OCH₃ | 10 |
| OCH₃ | OCH₃ | OCH₃ | 12 |
| OCH₃ | OCH₃ | OCH₃ | 14 |
| OCH₃ | OCH₃ | OCH₃ | 16 | and also the organic or mineral acid or base salts thereof, the geometrical isomers and tautomers thereof, and the solvates thereof;

wherein

M' represents an anionic counterion, derived from a salt of an organic or mineral acid, or from an organic or mineral base that ensures the electrical neutrality of the dye; and $Q^+$ represents a cationic counterion, it being understood that when the dye comprises an alkoxide group, then M' and $Q^+$ may be absent to ensure the electrical neutrality of said dye.

13. The process according to claim 1, characterized in that it also comprises the application to said keratin fibres of one or more reducing agents.

14. The process according to claim 1, characterized in that it does not use any reducing agent.

15. The process according to claim 1, characterized in that the triarylmethane dye(s) (a), and the fluorescent dye(s) (b), are applied together to the keratin fibre.

16. The process according to claim 1, characterized in that it comprises at least the following two successive steps:
a first step of applying to said keratin fibres a cosmetic composition comprising one or more fluorescent dyes (b), followed by,
a second step of applying to said fibres a cosmetic composition comprising one or more triarylmethane dyes (a) chosen from the compounds of formula (I), and also the optical isomers thereof, the geometrical isomers thereof, the tautomers thereof, the organic or mineral, acid or base salts thereof, the solvates thereof, and mixtures thereof.

17. The process according to claim 1, characterized in that it comprises at least the following two successive steps:
a first step of applying to said keratin fibres a cosmetic composition comprising one or more triarylmethane dyes (a) chosen from the compounds of formula (I), and also the optical isomers thereof, the geometrical isomers thereof, the tautomers thereof, the organic or mineral, acid or base salts thereof, the solvates thereof, and mixtures thereof, followed by
a second step of applying to said fibres a cosmetic composition comprising one or more fluorescent dyes (b).

18. The process according to claim 17, characterized in that it comprises at least two successive steps in which the pH of the cosmetic composition(s) is between 6 and 11 inclusive.

19. A cosmetic composition comprising one or more triarylmethane dyes (a) chosen from the compounds of formula (I), and also the optical isomers thereof, the geometrical isomers thereof, the tautomers thereof, the organic or mineral acid or base salts thereof, the solvates thereof, and mixtures thereof, and one or more fluorescent dyes (b), said composition optionally having a pH of between 6 and 11 inclusive, wherein:
the compound of formula (I) is:

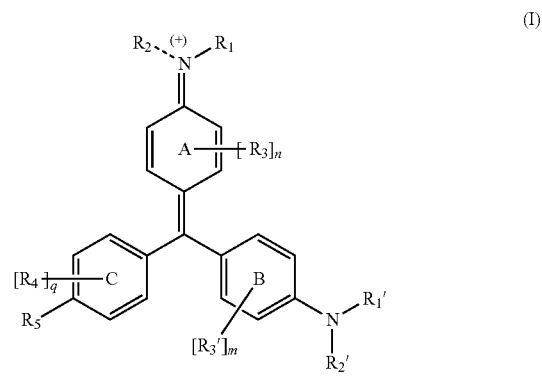

(I)

in which formula (I):
R$_1$, R$_2$, R'$_1$ and R'$_2$, which may be identical or different, represent:
a hydrogen atom,
a linear or branched C$_1$ to C$_{20}$ alkyl radical: that is optionally substituted and/or optionally interrupted with one or more heteroatoms, one or more groups comprising at least one heteroatom, or combinations thereof, or
a benzyl radical optionally substituted with one or more SO$_3^-$ or SO$_3$H groups R$_3$ and R'$_3$, which may be identical or different, represent, independently of each other:
a linear or branched C$_1$ to C$_6$ alkyl radical;
a sulfonate group SO$_3^-$, or
a sulfonic group SO$_3$H:

n and m, which may be identical or different, represent two integers ranging from 0 to 4;

the radicals R$_4$, which may be identical or different, represent, independently of each other:
a linear or branched C$_1$ to C$_6$ alkyl radical:
a hydroxyl radical,
a group SO$_3^-$,
a group SO$_3$H,
a halogen atom,
or alternatively two adjacent radicals R$_4$ together form an unsaturated 6-membered ring, optionally substituted with one or more SO$_3^-$ or SO$_3$H groups:

q is an integer ranging from 0 to 4:

R$_5$ represents:
a hydrogen atom,
a halogen atom,
an amino radical,
a hydroxyl radical,
an electron-withdrawing group SO$_3^-$ or SO$_3$H, or
a radical —NR$_6$R$_7$, in which R$_6$ and R$_7$, which may be identical or different, represent, independently of each other:
a hydrogen atom, or
a linear or branched C$_1$ to C$_6$ alkyl radical:

it being understood that:
the radical R$_2$ is present or absent, symbolized by the dashed bond, when R$_2$ is present, then the nitrogen atom that bears it is in cationic ammonium form, when R$_2$ is absent, then the nitrogen atom that bears it is not charged, (+) is not present, and the compound of formula (I) optionally comprises one or more anions An$^-$ and optionally one or more cations M$^+$ to ensure the electrical neutrality of the molecule with:
An$^-$ representing an anion; and
M$^+$ representing a cation; and one or more fluorescent dyes (b) are direct dyes chosen from the styryl dyes of formula (VIII) below, and also the organic or mineral acid or base salts thereof, the optical isomers, geometrical isomers and tautomers thereof, and the solvates thereof:

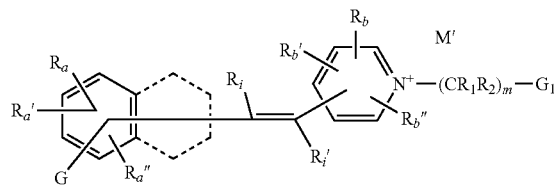

(VIII)

in which formula (VIII):
R$_1$ and R$_2$, which may be identical or different, represent a hydrogen atom or a C$_1$-C$_6$ alkyl group;
G$_1$ represents a hydrogen atom or a group chosen from NH$_2$ and OH;
R$_a$, R'$_a$, R"$_a$, R$_b$, R'$_b$ and R"$_b$ which may be identical or different, represent a) a hydrogen atom, b) a halogen atom, a group from among: c) amino, d) (C$_1$-C$_4$)alkylamino, e) (C$_1$-C$_4$)dialkylamino, f) cyano, g) carboxyl —C(O)OH or carboxylate —C(O)O$^-$, Q$^+$, h) hydroxyl —OH or alkoxide —O$^-$Q$^+$, i) (poly)halo (C$_1$-C$_6$)alkyl, i) acylamino, k) (C$_1$-C$_6$)alkoxy, l) (C$_1$-C$_6$)alkylthio, m) (poly)hydroxy(C$_2$-C$_4$)alkoxy, n) (C$_1$-C$_6$)alkylcarbonyloxy, o) (C$_1$-C$_6$)alkoxycarbonyl, p) (C$_1$-C$_6$)alkylcarbonylamino, q) acylamino, r) carbamoyl, s) (C$_1$-C$_6$)alkylsulfonylamino, t) aminosulfonyl, u) —SO$_3$H or sulfonate —SO$_3^-$, Q$^+$ or v) (C$_1$-C$_6$)alkyl optionally substituted with a group chosen from (C$_1$-C$_6$)alkoxy, hydroxyl, cyano, carboxyl, amino, (di)(C$_1$-C$_4$)alkylamino, or alternatively the two alkyl radicals borne by the nitrogen atom of the amino group form a 5- to 7-membered heterocycle optionally comprising another nitrogen or non-nitrogen heteroatom;

or alternatively two groups R$_a$ and R'$_a$; R$_b$ and R'$_b$ borne by two adjacent carbon atoms together form a benzo or indeno ring, a fused heterocycloalkyl or fused heteroaryl group; the benzo, indeno, heterocycloalkyl or heteroaryl ring being optionally substituted with a halogen atom, an amino, (C$_1$-C$_4$)alkylamino, (C$_1$-C$_4$)dialkylamino, nitro, cyano, carboxyl, hydroxyl or trifluoromethyl group, an acylamino, (C$_1$-C$_4$)alkoxy (poly)hydroxy(C$_1$-C$_4$)alkoxy, (C$_1$-C$_4$)alkylcarbonyloxy, (C$_1$-C$_4$)alkoxycarbonyl or (C$_1$-C$_4$)alkylcarbonylamino radical, an acylamino, carbamoyl or alkoxyalkylsulfonylamino radical, an aminosulfonyl radical, or a (C$_1$-C$_6$)alkyl radical optionally substituted with: a group chosen from (C$_1$-C$_6$)alkoxy, hydroxyl, cyano, carboxyl, amino, (C$_1$-C$_4$)alkylamino and (C$_1$-C$_4$)dialkylamino, or alternatively the two alkyl radicals borne by the nitrogen atom of the amino group form a 5- to 7-membered heterocycle optionally comprising another nitrogen or non-nitrogen heteroatom;

or alternatively, two groups R$_i$ and R$_a$; and/or a group R'$_i$ and R'$_a$ together form a fused (hetero)cycloalkyl;
G represents i) a group —NR$_c$R$_d$, ii) —OR with R representing a) a hydrogen atom, b) an optionally substituted, c) an optionally substituted (hetero)aryl group, d) an optionally substituted (hetero)aryl($C_1$-$C_6$)alkyl group, e) an optionally substituted (hetero)cycloalkyl, or f) an optionally substituted (hetero)cycloakyl($C_1$-$C_6$)alkyl;

or alternatively when G represents —$NR_cR_d$, two groups $R_c$ and $R'_a$ and/or $R_d$ and $R_a$ together form a saturated heteroaryl or heterocycle, optionally substituted with one or more ($C_1$-$C_6$)alkyl groups;

$R_i$ and $R'_i$, which may be identical or different, represent a hydrogen atom or a ($C_1$-$C_4$)alkyl group;

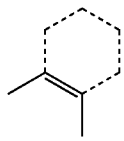

represents an aryl or heteroaryl group fused to the phenyl ring; or alternatively is absent from the phenyl ring;

m represents an integer between 1 and 18 inclusive; and

M' represents an anionic counterion, derived from a salt of an organic or mineral acid, or from an organic or mineral base that ensures the electrical neutrality of the dye.

20. A multi-compartment device comprising a first compartment containing one or more triarylmethane dyes (a) chosen from the compounds of formula (I), and also the optical isomers thereof, the geometrical isomers thereof, the tautomers thereof, the organic or mineral acid or base salts thereof, the solvates thereof, and mixtures thereof, and a second compartment containing one or more fluorescent dyes (b), wherein:

the compound of formula (I) is:

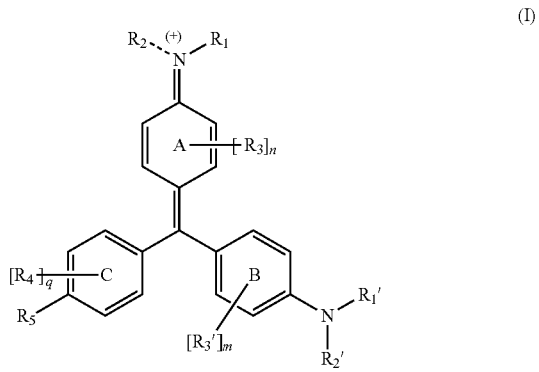

(I)

in which formula (I):

$R_1$, $R_2$, $R'_1$ and $R'_2$, which may be identical or different, represent:
a hydrogen atom,
a linear or branched $C_1$ to $C_{20}$ alkyl radical:
that is optionally substituted and/or
optionally interrupted with one or more heteroatoms, one or more groups comprising at least one heteroatom, or combinations thereof, or
a benzyl radical optionally substituted with one or more $SO_3^-$ or $SO_3H$ groups $R_3$ and $R'_3$, which may be identical or different, represent, independently of each other:
a linear or branched $C_1$ to $C_6$ alkyl radical;
a sulfonate group $SO_3^-$, or
a sulfonic group $SO_3H$;
n and m, which may be identical or different, represent two integers ranging from 0 to 4;
the radicals $R_4$, which may be identical or different, represent, independently of each other:
a linear or branched $C_1$ to $C_6$ alkyl radical:
a hydroxyl radical,
a group $SO_3^-$,
a group $SO_3H$,
a halogen atom,
or alternatively two adjacent radicals $R_4$ together form an unsaturated 6-membered ring optionally substituted with one or more $SO_3^-$ or $SO_3H$ groups:
q is an integer ranging from 0 to 4:
$R_5$ represents:
a hydrogen atom,
a halogen atom,
an amino radical,
a hydroxyl radical,
an electron-withdrawing group $SO_3^-$ or $SO_3H$, or
a radical —$NR_6R_7$, in which $R_6$ and $R_7$, which may be identical or different, represent, independently of each other:
a hydrogen atom, or
a linear or branched $C_1$ to $C_6$ alkyl radical:
it being understood that:
the radical $R_2$ is present or absent, symbolized by the dashed bond, when $R_2$ is present, then the nitrogen atom that bears it is in cationic ammonium form, when $R_2$ is absent, then the nitrogen atom that bears it is not charged, (+) is not present, and the compound of formula (I) optionally comprises one or more anions $An^-$ and optionally one or more cations $M^+$ to ensure the electrical neutrality of the molecule;
with:
$An^-$ representing an anion; and
$M^+$ representing a cation; and
one or more fluorescent dyes (b) are direct dyes chosen from the styryl dyes of formula (VIII) below, and also the organic or mineral acid or base salts thereof, the optical isomers, geometrical isomers and tautomers thereof, and the solvates thereof:

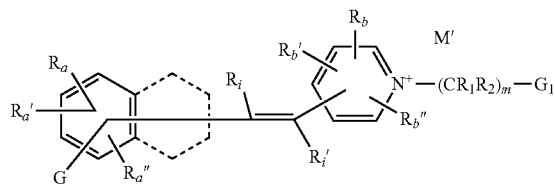

(VIII)

in which formula (VIII):
- $R_1$ and $R_2$, which may be identical or different, represent a hydrogen atom or a $C_1$-$C_6$ alkyl group;
- $G_1$ represents a hydrogen atom or a group chosen from $NH_2$ and OH;
- $R_a$, $R'_a$, $R''_a$, $R_b$, $R'_b$ and $R''_b$ which may be identical or different, represent a) a hydrogen atom, b) a halogen atom, a group from among: c) amino, d) ($C_1$-$C_4$) alkylamino, e) ($C_1$-$C_4$)dialkylamino, f) cyano, g) carboxyl —C(O)OH or carboxylate —C(O)O$^-$, Q$^+$, h) hydroxyl —OH or alkoxide —O$^-$Q$^+$, i) (poly)halo ($C_1$-$C_6$)alkyl, j) acylamino, k) ($C_1$-$C_6$)alkoxy, l) ($C_1$-$C_6$)alkylthio, m) (poly)hydroxy($C_2$-$C_4$)alkoxy, n) ($C_1$-$C_6$)alkylcarbonyloxy, o) ($C_1$-$C_6$)alkoxycarbonyl, p) ($C_1$-$C_6$)alkylcarbonylamino, q) acylamino, r) carbamoyl, s) ($C_1$-$C_6$)alkylsulfonylamino, t) aminosulfonyl, u) —SO$_3$H or sulfonate —SO$_3^-$, Q$^+$ or v) ($C_1$-$C_6$)alkyl optionally substituted with a group chosen from ($C_1$-$C_6$)alkoxy, hydroxyl, cyano, carboxyl, amino, (di)($C_1$-$C_4$)alkylamino, or alternatively the two alkyl radicals borne by the nitrogen atom of the amino group form a 5- to 7-membered heterocycle optionally comprising another nitrogen or non-nitrogen heteroatom;
- or alternatively two groups $R_a$ and $R'_a$; $R_b$ and $R'_b$ borne by two adjacent carbon atoms together form a benzo or indeno ring, a fused heterocycloalkyl or fused heteroaryl group;
- the benzo, indeno, heterocycloalkyl or heteroaryl ring being optionally substituted with a halogen atom, an amino, ($C_1$-$C_4$)alkylamino, ($C_1$-$C_4$)dialkylamino, nitro, cyano, carboxyl, hydroxyl or trifluoromethyl group, an acylamino, ($C_1$-$C_4$)alkoxy (poly)hydroxy($C_1$-$C_4$) alkoxy, ($C_1$-$C_4$)alkylcarbonyloxy, ($C_1$-$C_4$)alkoxycarbonyl or ($C_1$-$C_4$)alkylcarbonylamino radical, an acylamino, carbamoyl or alkoxyalkylsulfonylamino radical, an aminosulfonyl radical, or a ($C_1$-$C_6$)alkyl radical optionally substituted with: a group chosen from ($C_1$-$C_6$)alkoxy, hydroxyl, cyano, carboxyl, amino, ($C_1$-$C_4$)alkylamino and ($C_1$-$C_4$)dialkylamino, or alternatively the two alkyl radicals borne by the nitrogen atom of the amino group form a 5- to 7-membered heterocycle optionally comprising another nitrogen or non-nitrogen heteroatom;
- or alternatively, two groups $R_i$ and $R_a$; and/or a group $R'_1$ and $R'_a$ together form a fused (hetero)cycloalkyl;
- G represents i) a group —NR$_c$R$_d$, ii) —OR with R representing a) a hydrogen atom, b) an optionally substituted, c) an optionally substituted (hetero)aryl group, d) an optionally substituted (hetero)aryl($C_1$-$C_6$)alkyl group, e) optionally substituted (hetero) cycloalkyl, or f) optionally substituted (hetero)cycloalkyl($C_1$-$C_6$)alkyl;
- or alternatively when G represents —NR$_c$R$_d$, two groups $R_c$ and $R'_a$ and/or $R_d$ and $R_a$ together form a saturated heteroaryl or heterocycle, optionally substituted with one or more ($C_1$-$C_6$)alkyl groups;
- $R_i$ and $R'_i$, which may be identical or different, represent a hydrogen atom or a ($C_1$-$C_4$)alkyl group;

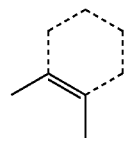

represents an aryl or heteroaryl group fused to the phenyl ring; or alternatively is absent from the phenyl ring;
- m represents an integer between 1 and 18 inclusive; and
- M' representing an anionic counterion, derived from a salt of an organic or mineral acid, or from an organic or mineral base that ensures the electrical neutrality of the dye.

21. The process of claim 1, wherein the keratin fibres are human hair in chestnut-brown, dark chestnut-brown, brown, brown with a glint, or black color, and wherein the process does not use an additional dye other than (a) or (b).

* * * * *